(12) United States Patent
Barve et al.

(10) Patent No.: US 12,381,008 B1
(45) Date of Patent: Aug. 5, 2025

(54) SYSTEM AND METHODS FOR OBSERVING MEDICAL CONDITIONS

(71) Applicant: Anumana, Inc., Cambridge, MA (US)

(72) Inventors: Rakesh Barve, Bengaluru (IN); Tyler Wagner, Boston, MA (US)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/802,393

(22) Filed: Aug. 13, 2024

(51) Int. Cl.
*G16H 50/20* (2018.01)
*G06N 3/04* (2023.01)
*G16H 10/60* (2018.01)

(52) U.S. Cl.
CPC ............ *G16H 50/20* (2018.01); *G06N 3/04* (2013.01); *G16H 10/60* (2018.01)

(58) Field of Classification Search
CPC .................. G16H 50/20; G16H 10/60; G16H 10/00–80/00; G06N 3/04
See application file for complete search history.

(56) References Cited

U.S. PATENT DOCUMENTS

| | | | | |
|---|---|---|---|---|
| 10,770,180 | B1* | 9/2020 | Kemp | G16H 10/60 |
| 12,102,485 | B2* | 10/2024 | Vaid | A61B 8/065 |
| 2016/0063212 | A1* | 3/2016 | Monier | G16H 10/60 705/3 |
| 2016/0135706 | A1* | 5/2016 | Sullivan | A61B 5/0006 600/509 |
| 2016/0154934 | A1 | 6/2016 | Rowlandson et al. | |
| 2016/0188823 | A1 | 6/2016 | Rowlandson et al. | |
| 2016/0210435 | A1* | 7/2016 | Neumann | G09B 23/288 |
| 2016/0213261 | A1* | 7/2016 | Fleischer | A61B 5/0205 |
| 2017/0071478 | A1* | 3/2017 | Chen | A61B 5/339 |
| 2018/0242863 | A1* | 8/2018 | Lui | A61B 5/7275 |
| 2018/0365381 | A1* | 12/2018 | Tang | G16H 50/20 |

(Continued)

FOREIGN PATENT DOCUMENTS

| | | | |
|---|---|---|---|
| CN | 116226724 A | * | 6/2023 |
| CN | 118098614 A | * | 5/2024 |

(Continued)

OTHER PUBLICATIONS

Somani et al., "Development of a machine learning model using electrocardiogram signals to improve acute pulmonary embolism screening," European Heart Journal—Digital Health (2022) 3, 56-66; https://doi.org/10.1093/ehjdh/ztab101. (Year: 2022).*

(Continued)

*Primary Examiner* — Jonathon A. Szumny
(74) *Attorney, Agent, or Firm* — Caldwell Intellectual Property Law

(57) ABSTRACT

System for observing medical conditions and methods used therein include a processor and a memory connected to the processor, wherein the memory contains instructions configuring the processor to receive, from a data repository, a plurality of reference electronic health records and a plurality of reference cardiac data elements, generate medical training data, train at least an observation machine learning model using the generated medical training data, receive a query pertaining to a subject, wherein the query includes at least a query cardiac data element and at least a query electronic health record, and output at least an observation outcome as a function of the query using the at least an observation machine learning model.

18 Claims, 20 Drawing Sheets

(56) References Cited

U.S. PATENT DOCUMENTS

| | | | |
|---|---|---|---|
| 2019/0034591 A1* | 1/2019 | Mossin | G06N 3/08 |
| 2020/0327985 A1* | 10/2020 | Du | G16H 10/60 |
| 2020/0365270 A1* | 11/2020 | Kazemi Oskooei | G06N 3/08 |
| 2021/0022660 A1* | 1/2021 | Quinn | A61B 5/4842 |
| 2021/0027025 A1* | 1/2021 | Olabiyi | G10L 15/063 |
| 2021/0150693 A1* | 5/2021 | Fornwalt | G06N 3/045 |
| 2021/0183484 A1* | 6/2021 | Shaib | G06F 40/295 |
| 2021/0304855 A1* | 9/2021 | Ansari | G16H 50/20 |
| 2021/0353203 A1* | 11/2021 | Burman | G16H 50/30 |
| 2022/0044809 A1* | 2/2022 | Bihorac | G16H 10/60 |
| 2022/0051805 A1* | 2/2022 | Yerebakan | G16H 50/70 |
| 2022/0095911 A1* | 3/2022 | DeAyala | A61B 3/0025 |
| 2022/0180202 A1* | 6/2022 | Yin | G06F 16/355 |
| 2022/0183571 A1 | 6/2022 | Johnson et al. | |
| 2022/0189636 A1* | 6/2022 | Wagner | G06N 3/08 |
| 2022/0287648 A1* | 9/2022 | Cannesson | A61B 5/7267 |
| 2022/0351858 A1* | 11/2022 | Khan | G16H 70/40 |
| 2022/0378379 A1* | 12/2022 | Zimmerman | A61B 5/7275 |
| 2022/0384045 A1* | 12/2022 | Zimmerman | A61B 5/7275 |
| 2023/0028783 A1* | 1/2023 | Zimmerman | A61B 5/333 |
| 2023/0135769 A1* | 5/2023 | Bhattacharya | G06N 3/088 345/156 |
| 2023/0161978 A1* | 5/2023 | Sehanobish | G06T 7/0012 704/9 |
| 2023/0297895 A1* | 9/2023 | Lim | G06N 3/0442 |
| 2023/0346288 A1* | 11/2023 | Hughes | A61B 5/346 |
| 2023/0377751 A1* | 11/2023 | Somani | G16H 50/20 |
| 2024/0062052 A1* | 2/2024 | Kumar | G16H 50/70 |
| 2024/0145050 A1* | 5/2024 | Thompson, IV et al. | G06F 16/353 |
| 2024/0206821 A1* | 6/2024 | Upadhyay | A61B 5/318 |
| 2024/0221936 A1* | 7/2024 | Nemani | G16H 30/40 |
| 2024/0232590 A1* | 7/2024 | Sengupta | G06N 3/044 |
| 2024/0303506 A1* | 9/2024 | Wang | G06N 3/0895 |
| 2024/0303544 A1* | 9/2024 | Baranzini | G06N 5/022 |
| 2024/0341852 A1* | 10/2024 | Villongco | A61B 34/10 |
| 2024/0363247 A1* | 10/2024 | Attia | G16H 50/30 |
| 2025/0061989 A1* | 2/2025 | Heilbroner | G16H 10/60 |

FOREIGN PATENT DOCUMENTS

| | | | | |
|---|---|---|---|---|
| WO | WO-2023277814 A2 * | 1/2023 | | G01C 21/3492 |
| WO | WO-2024014821 A1 * | 1/2024 | | |

OTHER PUBLICATIONS

McKeen et al., "ECG-FM: An Open Electrocardiogram Foundation Model," arXiv:2408.05178v1 [cs. LG] Aug. 9, 2024. (Year: 2024).*

Bajaj et al., "Heart Disease Prediction using Ensemble ML," Proceedings of the International Conference on Sustainable Computing and Data Communication Systems (ICSCDS-2023); IEEE Xplore Part No. CFP23AZ5-ART; ISBN: 978-1-6654-9199-0. (Year: 2023).*

L. Jing et al; rECHOmmend: An ECG-Based Machine Learning Approach for Identifying Patients at Increased Risk of Undiagnosed Structural Heart Disease Detectable by Echocardiography; Circulation. 2022;146:36-47.

* cited by examiner

SYSTEM AND METHODS FOR OBSERVING MEDICAL CONDITIONS

FIELD OF THE INVENTION

The present invention generally relates to the field of medical informatics and machine learning. In particular, the present invention is directed to system and methods for observing medical conditions.

BACKGROUND

Early detection and prediction of medically relevant attributes plays a crucial role in the timely diagnosis and treatment of many challenging medical conditions such as pulmonary hypertension. However, such detection and prediction often rely on invasive diagnostic tools, and medical professionals are often faced with a large quantity of unlabeled clinical data that potentially obscure the detection of these medically relevant attributes.

SUMMARY OF THE DISCLOSURE

In an aspect, a system for observing medical conditions is described. System includes a processor and a memory communicatively connected to the processor, wherein the memory contains instructions configuring the processor to receive, from a data repository, a plurality of reference electronic health records (EHRs) and a plurality of reference cardiac data elements and generate medical training data including a plurality of reference features correlated with a plurality of reference factors, wherein generating the medical training data includes extracting the plurality of reference features from the plurality of reference cardiac data elements, isolating the plurality of reference factors from the plurality of reference EHRs, and correlating the plurality of reference features and the plurality of reference factors to generate the medical training data. Processor is further configured to train at least an observation machine learning model using generated medical training data, receive a query pertaining to a subject, wherein the query includes at least a query cardiac data element and at least a query EHR, and output at least an observation outcome as a function of the query using the at least an observation machine learning model.

In another aspect, a method for observing medical conditions is described. Method is performed by processor and includes receiving from data repository plurality of reference EHRs and plurality of reference cardiac data elements and generating medical training data including plurality of reference features correlated with plurality of reference factors, wherein generating the medical training data includes extracting the plurality of reference features from plurality of the reference cardiac data elements, isolating the plurality of reference factors from the plurality of reference EHRs, and correlating the plurality of reference features and the plurality of reference factors to generate the medical training data. Method further includes training at least an observation machine learning model using generated medical training data, receiving query pertaining to subject, wherein the query includes at least a query cardiac data element and at least a query EHR, and outputting at least an observation outcome as a function of the query using the at least an observation machine learning model.

These and other aspects and features of nonlimiting embodiments of the present invention will become apparent to those skilled in the art upon review of the following description of specific nonlimiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for observing medical conditions. In one or more embodiments, system may include a processor and a memory communicatively connected to the processor, wherein the memory contains instructions configuring the processor to receive, from a data repository, a plurality of reference electronic health records (EHRs) and a plurality of reference cardiac data elements. In one or more embodiments, processor may be further configured to generate medical training data including a plurality of reference features extracted from plurality of reference cardiac data elements correlated with a plurality of reference factors isolated from plurality of reference EHRs. In one or more embodiments, processor may be further configured to train at least an observation machine learning model, such as a transformer-based machine learning model or a contrastive machine learning model, using generated medical training data. In one or more embodiments, processor may be further configured to receive a query pertaining to a subject, wherein the query includes at least a query cardiac data element and at least a query EHR, and output at least an observation outcome as a function of the query using at least an observation machine learning model.

Aspects of the present disclosure may be used to provide clinical decision support. Exemplary embodiments illustrating aspects of the present disclosure are described below in the context of several specific examples.

Figure 1:
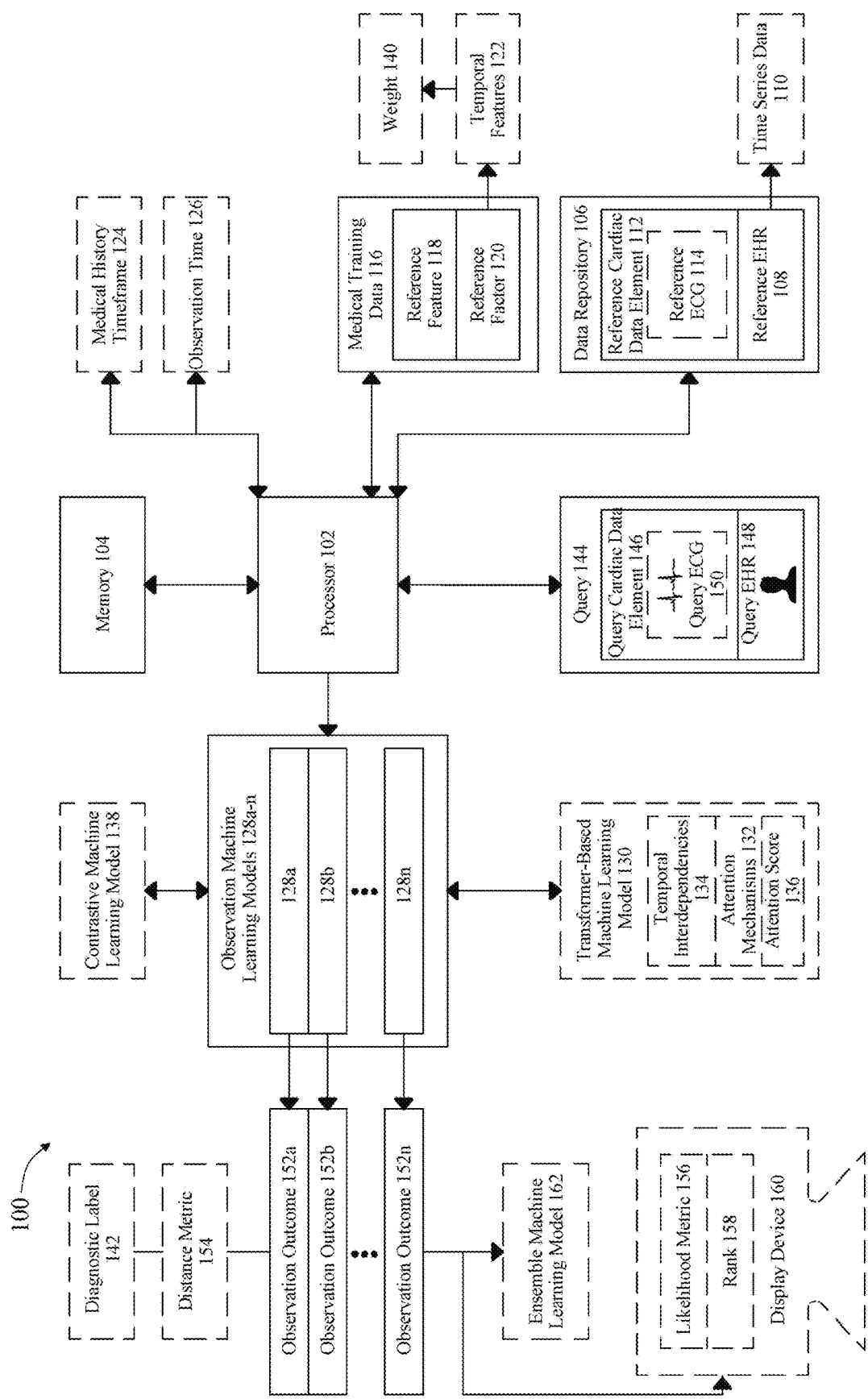
FIG. 1 is an exemplary embodiment of a system for observing medical conditions.

Referring now to FIG. 1, an exemplary embodiment of system 100 for prediction of medical conditions is illustrated. System 100 includes a processor 102. In one or more embodiments, processor 102 may include a computing device. Computing device could include any analog or digital control circuit, including an operational amplifier circuit, a combinational logic circuit, a sequential logic circuit, an application-specific integrated circuit (ASIC), a field programmable gate arrays (FPGA), or the like. Computing device may include a processor communicatively connected to a memory, as described above. Computing device may include any computing device as described in this disclosure, including without limitation a microcontroller, microprocessor, digital signal processor, and/or system on a chip as described in this disclosure. Computing device may include, be included in, and/or communicate with a mobile device such as a mobile telephone, smartphone, or tablet. Computing device may include a single computing device operating independently, or may include two or more computing device operating in concert, in parallel, sequentially, or the like; two or more computing devices may be included together in a single computing device or in two or more computing devices. Computing device may interface or communicate with one or more additional devices as described below in further detail via a network interface device. Network interface device may be utilized for connecting computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device may include but is not limited to, for example, a first computing device or cluster of computing devices in a first location and a second computing device or cluster of computing devices in a second location. Computing device may include one or more computing devices dedicated to data storage, security, distribution of traffic for load balancing, and the like. Computing device may distribute one or more computing tasks as described below across a plurality of computing devices of computing device, which may operate in parallel, in series, redundantly, or in any other manner used for distribution of tasks or memory between computing devices. Computing device may be implemented, as a nonlimiting example, using a "shared nothing" architecture.

With continued reference to FIG. 1, computing device may be designed and/or configured to perform any method, method step, or sequence of method steps in any embodiment described in this disclosure, in any order and with any degree of repetition. For instance, computing device may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. A person of ordinary skill in the art, upon reviewing the entirety of this disclosure, will be aware of various ways in which steps, sequences of steps, processing tasks, and/or data may be subdivided, shared, or otherwise dealt with using iteration, recursion, and/or parallel processing. More details regarding computing devices will be described below.

With continued reference to FIG. 1, system 100 includes a memory 104 communicatively connected to processor 102, wherein the memory 104 contains instructions configuring the processor 102 to perform any processing steps described herein. For the purposes of this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, using a bus or other facility for intercommunication between elements of a computing device. Communicative connecting may also include indirect connections via, for example and without limitation, wireless connection, radio communication, low-power wide-area network, optical communication, magnetic, capacitive, or optical coupling, and the like. In some instances, the terminology "communicatively coupled" may be used in place of communicatively connected in this disclosure.

With continued reference to FIG. 1, computing device may perform determinations, classification, and/or analysis steps, methods, processes, or the like as described in this disclosure using machine learning processes. For the purposes of this disclosure, a "machine learning process" is a process that automatedly uses a body of data known as "training data" and/or a "training set" to generate an algorithm that will be performed by a processor module to produce outputs given data provided as inputs; this is in contrast to a nonmachine learning software program where the commands to be executed are determined in advance by a user and written in a programming language. A machine learning process may utilize supervised, unsupervised, lazy-learning processes and/or neural networks. More details regarding computing devices and machine learning processes will be provided below.

With continued reference to FIG. 1, in one or more embodiments, system 100 may include or be communicatively connected to a database. For the purposes of this disclosure, a "database" is an organized collection of data or a type of data store based on the use of a database management system (DBMS), the software that interacts with end users, applications, and the database itself to capture and analyze the data. Database may be implemented, without limitation, as a relational database, a key-value retrieval database such as a NoSQL database, or any other format or structure for use as database that a person of ordinary skill in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described in this disclosure. Data entries in database may be flagged with or linked to one or more additional elements of information, which may be reflected in data entry cells and/or in linked tables such as tables related by one or more indices in database or another relational database. A person of ordinary skill in the art, upon reviewing the entirety of this disclosure, will be aware of various ways in which data entries in database may store, retrieve, organize, and/or reflect data and/or records as used herein, as well as categories and/or populations of data consistently with this disclosure.

With continued reference to FIG. 1, system 100 may include or be communicatively connected to one or more electronic health records (EHR) of one or more patients. For the purposes of this disclosure, an electronic health record (EHR) is a comprehensive collection of records relating to the health history, diagnosis, or condition of patient, relating to treatment provided or proposed to be provided to the patient, or relating to additional factors that may impact the health of the patient. Elements within an EHR, once combined, provide a detailed picture of a patient's overall health. In one or more embodiments, data may be deposited to and retrieved from one or more EHRs in order to in order to perform one or more functions of system 100. In one or more embodiments, EHR may include demographic data of patient; for example, and without limitation, EHR may include basic information about patient such as name, age, gender, ethnicity, socioeconomic status, and/or the like. In one or more embodiments, each EHR may also include patient's medical history; for example, and without limitation, EHR may include a detailed record of patient's past health conditions, medical procedures, hospitalizations, and illnesses such as surgeries, treatments, medications, allergies, and/or the like. In one or more embodiments, each EHR may include lifestyle information of patient; for example, and without limitation, EHR may include details about the patient's diet, exercise habits, smoking and alcohol consumption, and other behaviors that could impact patient's health. In one or more embodiments, EHR may include patient's family history; for example, and without limitation, EHR may include a record of hereditary diseases. In one or more embodiments, EHR may include one or more digital files or documents that contain one or more elements described above. In one or more embodiments, a database may include a plurality of EHRs. In one or more embodiments, EHRs may be deposited to and/or retrieved from a database or a repository of similar nature as a database.

With continued reference to FIG. 1, for the purposes of this disclosure, a "patient" is a human or any individual organism, on whom or on which a procedure, study, or otherwise experiment, is conducted. As nonlimiting examples, patient may include a human subject with symptoms of atrial fibrillation or pulmonary hypertension, an individual undergoing cardiac screening, a participant in a clinical trial, an individual with congenital heart disease, a heart transplant candidate, an individual receiving follow-up care after cardiac surgery, a healthy volunteer, an individual with heart failure, or the like. Additionally or alternatively, patient may include a pet or an animal model (i.e., an animal used to model certain medical conditions such as a laboratory rat).

With continued reference to FIG. 1, system 100 includes or is communicatively connected to a data repository 106. For the purposes of this disclosure, a "data repository" is a structured collection of data to which another set of data is compared in order to obtain one or more results and/or initiate one or more steps. Data repository 106 includes a plurality of EHRs, consistent with details described above. Additionally and/or alternatively, data repository 106 may include, for example and without limitation, clinical data, research findings, case studies, diagnostic criteria, treatment outcomes, patient records, and/or the like. Additionally and/or alternatively, data repository 106 may include or be linked to a centralized or distributed source of medical data such as a hospital information system (HIS), regional health information organization (RHIO), health information exchange (HIE), cloud-based EHR platform, research database and biobank, public health database, clinical registry, among others. In one or more embodiments, data repository 106 may include one or more databases or the like and may be implemented in any manner suitable for implementation of databases.

With continued reference to FIG. 1, processor 102 is configured to receive, from data repository 106, a plurality of reference electronic health records (EHRs). For the purposes of this disclosure, a "reference electronic health record (EHR)" is an electronic health record (EHR), as described above, that serves as a benchmark to which another electronic health record (EHR) may be compared in order to make a determination and/or to initiate one or more subsequent steps. In one or more embodiments, at least a reference EHR 108 may include time series data 110. For the purposes of this disclosure, "time series data" are data measured as a function of time and/or recorded over consistent intervals of time. In one or more embodiments, time series data 110 may include information related to patient's health and recorded over weeks, months, years, or decades. In some cases, time series data 110 may include only data or information after the occurrence of certain event or events, such as trauma, diagnosis, therapy, use of prescription or substance, among others. As nonlimiting examples, time series data 110 may include parameters such as weight, body fat, bone density, blood pressure, cholesterol levels, tobacco/alcohol consumption, substance usage, prescription dosage, or the like. Time series data 110 may contain valuable information regarding a patient's journey with respect to a medical condition. Alternatively and/or additionally, time series data 110 may be used to reveal insights regarding the future trajectories of a medical condition.

With continued reference to FIG. 1, processor 102 is configured to receive, from data repository 106, a plurality of reference cardiac data elements 112. Similar to details described above, for the purposes of this disclosure, a "reference cardiac data element" is a cardiac data element serves as a benchmark to which another data element is compared in order to make a determination and/or to initiate one or more subsequent steps. For the purposes of this disclosure, a "cardiac data element" is a data element pertaining to the structural and/or functional features of a patient's heart. In one or more embodiments, at least a reference cardiac data element 112 may include an image or a graphical representation of data similar thereto. In one or more embodiments, at least a reference cardiac data element 112 may include at least a reference electrocardiogram (ECG) 114. For the purposes of this disclosure, an "electrocardiogram (ECG)" is a recording of electrical activity of patient's heart over a period of time. In one or more embodiments, ECG may include one or more recordings captured by a plurality (e.g., 12) of electrodes placed on patient's skin. In one or more embodiments, ECG data may include information regarding a P wave, T wave, QRS complex, PR interval, ST segment, and/or the like. In one or more embodiments, ECG data may be used to identify specific cardiac events or phases of a cardiac cycle, e.g., isovolumic relaxation, ventricular filling, isovolumic contraction, and rapid ventricular ejection.

With continued reference to FIG. 1, processor 102 is configured to generate medical training data 116 including a plurality of reference features 118 correlated with a plurality of reference factors 120. Generating medical training data 116 includes extracting plurality of reference features 118 from plurality of reference cardiac data elements 112. For the purposes of this disclosure, a "reference feature" is a feature used as a benchmark to which another feature may be compared in order to make a determination and/or to initiate one or more subsequent steps. In one or more embodiments. reference feature may be a numerical, descriptive, or categorical characteristic pertaining to one or more aspects of reference cardiac data element 112 that are potentially relevant to one or more observative and/or predictive functions of system 100. As a nonlimiting example, reference feature 118 may include one or more numerical indicators that represent a size, a shape, a symmetry, a curvature, an amplitude, a frequency, a temporal span, and/or the like of at least part of reference cardiac data element 112. In one or more embodiments, at least a reference feature 118 of plurality of reference features 118 includes at least an ECG feature extracted from at least a reference ECG 114, consistent with details described in U.S. patent application Ser. No. 18/771,914, filed on Jul. 12, 2024, entitled "APPARATUS AND METHODS FOR IDENTIFYING ABNORMAL BIOMEDICAL FEATURES WITHIN IMAGES OF BIOMEDICAL DATA", the entirety of which is incorporated herein by reference.

With continued reference to FIG. 1, generating medical training data 116 includes isolating the plurality of reference factors 120 from the plurality of reference EHRs and correlating the plurality of reference features 118 and the plurality of reference factors 120. For the purposes of this disclosure, a "reference factor" is a factor used as a benchmark to which another factor may be compared in order to make a determination and/or to initiate one or more subsequent steps. In one or more embodiments, reference factor 120 may be a numerical, descriptive, or categorical characteristic pertaining to one or more aspects of one or more reference EHRs 108, as described above, that are potentially relevant to one or more observative and/or predictive functions of system 100. In one or more embodiments, each reference factor 120 of plurality of reference factors 120 may represent a different aspect of reference EHR 108, such as without limitation, durations of symptoms or hospitalization, prescribed medications and dosages thereof, diagnosed medical conditions and severity thereof, risk factors, and/or the like.

With continued reference to FIG. 1, in one or more embodiments, plurality of reference factors 120 may include a plurality of temporal features 122. For the purposes of this disclosure, a "temporal feature" is a feature indicating the date of creation or recordation of a data element within one or more reference EHRs 108. As a nonlimiting example, temporal feature 122 may include a date in which a medication was prescribed, a date in which a physician note was written, a date in which laboratory results were received, and/or the like. In one or more embodiments, each digital file or document within reference EHR 108 may contain a correlated temporal feature 122. In one or more embodiments, data repository 106 may be configured to record a time in which each digital file or document was received and placed into reference EHR 108. In one or more embodiments, data repository 106 may be configured to record a time in which each digital file or document was edited, altered, or otherwise updated. In one or more embodiments, each digital file or document may contain a date and/or time when the digital file document was recorded. In one or more embodiments, metadata may indicate the date and/or time when a digital file or document was recorded. For the purposes of this disclosure, "metadata" are secondary data providing background information about one or more aspects of certain primary data that make it easier to track and/or work with the primary data. In one or more embodiment, each reference factor 120 may be associated with a unique temporal feature 122. In one or more embodiments, multiple reference factors 120, such as reference factors 120 extracted from the same document, may share the same or similar temporal features 122.

With continued reference to FIG. 1, in one or more embodiments, generating medical training data 116 may further include identifying a medical history timeframe 124 associated with at least a reference EHR 108 of plurality of reference EHRs 108. For the purposes of this disclosure, a "medical history timeframe" is a time span within reference EHR 108 in which a patient's past medical information is recorded. In one or more embodiments, medical history timeframe 124 may denote the recorded medical history of a patient. In some cases, medical history timeframe 124 may denote the amount of medical information recorded in units of years. As a nonlimiting example, for a hypothetical patient named John Doe within reference EHR 108, his earliest digital file or document may be recorded in 2017, whereas his latest digital file or document may be recorded in 2023; accordingly, medical history timeframe 124 for John Doe may include a time span of six years. In some cases, medical history timeframe 124 may indicate the entire time span during which medical information was recorded. In some cases, medical history timeframe 124 may indicate only one or more specific time spans in which a patient sought medical treatment. As a nonlimiting example, reference EHR 108 may contain a plurality of digital files or documents arranged in a sequential order, wherein medical history timeframe 124 may be determined by identifying a first date (e.g., the earliest date) on a first digital file/document, identifying a second date (e.g., the most recent date) on a second digital file/document, and calculating the difference between the first date and the second date.

With continued reference to FIG. 1, in one or more embodiments, generating medical training data 116 may further include segmenting at least a reference EHR 108 of the plurality of reference EHRs 108 as a function of medical history timeframe 124 and an observation time 126 of at least a month. For the purposes of this disclosure, an "observation time" is a pre-determined time frame within reference EHR 108 that is deemed to be of use, importance, or relevance. "Observation time" and "observation period" may be used interchangeably throughout this disclosure. Observation time 126 is potentially useful for identification of symptoms or factors that lead to a diagnosis. In one or more embodiments, only a particular time frame of reference EHR 108 may be of importance, wherein observation time 126 may define such time frame. As nonlimiting examples, if a diagnosis was made in 2021, and observation time 126 includes a six-year time frame, processor 102 may be configured to segment reference EHR 108 to isolate the portion thereof that spans from 2015 until 2021. In one or more embodiments, observation time 126 may exclude a period immediately prior to a diagnosis (i.e., a lead time, as described in detail below) in order to cover instances in which a patient already has one or more diseases that are not yet diagnosed. As nonlimiting examples, observation time 126 may include time frames beginning at least 1, 2, 3, 4, 5, 6, 7, 8, 9, 10, 11, or 12 month(s) and/or year(s) prior to a diagnosis. In one or more embodiments, observation time 126 may indicate that only information prior to diagnosis is useful, important, or relevant. Accordingly, processor 102 may segment/truncate reference EHR 108 to remove and discard any information recorded after diagnosis.

With continued reference to FIG. 1, in one or more embodiments, one or more machine learning models may be used to perform certain function or functions of system 100, as described below. Processor 102 may use a machine learning module to implement one or more algorithms as described herein or generate one or more machine learning models, such as observation machine learning model, as described below. However, machine learning module is exemplary and may not be necessary to generate one or more machine learning models and perform any machine learning described herein. In one or more embodiments, one or more machine learning models may be generated using training data. Training data may include inputs and corresponding predetermined outputs so that machine learning model may use correlations between the provided exemplary inputs and outputs to develop an algorithm and/or relationship that then allows the machine learning model to determine its own outputs for inputs. Training data may contain correlations that a machine learning process may use to model relationships between two or more categories of data elements. Exemplary inputs and outputs may be retrieved from a database, selected from one or more EHRs, or be provided by a user. In one or more embodiments, machine learning module may obtain training data by querying a communicatively connected database that includes past inputs and outputs. Training data may include inputs from various types of databases, resources, and/or user inputs and outputs correlated to each of those inputs, so that machine learning model may determine an output. Correlations may indicate causative and/or predictive links between data, which may be modeled as relationships, such as mathematical relationships, by machine learning models, as described in further detail below. In one or more embodiments, training data may be formatted and/or organized by categories of data elements by, for example, associating data elements with one or more descriptors corresponding to categories of data elements. As a nonlimiting example, training data may include data entered in standardized forms by persons or processes, such that entry of a given data element in a given field in a form may be mapped to one or more descriptors of categories. Elements in training data may be linked to descriptors of categories by tags, tokens, or other data elements. In one or more embodiments, training data may include previous outputs such that one or more machine learning models may iteratively produce outputs.

With continued reference to FIG. 1, processor 102 is configured to train at least an observation machine learning model 128*a-n* using medical training data 116. Specifically, in one or more embodiments, training at least an observation machine learning model 128*a-n* may include receiving medical training data 116 as inputs and a plurality of exemplary medical conditions as outputs and training the at least an observation machine learning model 128*a-n* by correlating the medical training data 116 with the plurality of exemplary medical conditions. Implementation of this machine learning model may be consistent with any type of machine learning model or algorithm described in this disclosure. In one or more embodiments, medical training data 116 may include data specifically synthesized for training purposes using one or more generative models. As a nonlimiting example, medical training data 116 may be generated or synthesized using deidentified patient data from EHRs. Deidentified patient data may be generated, as a nonlimiting example, using a generative machine learning model trained and configured to obfuscate data containing sensitive information, such as name, age, contact information, or the like, while preserving its utility for training purposes. Such deidentification procedure may be used to comply with privacy regulations and ethical standards. As another nonlimiting example, medical training data 116 may be extracted from medical literature, consistent with details disclosed in U.S. patent application Ser. No. 18/648,059, filed on Apr. 26, 2024, entitled "APPARATUS AND METHODS FOR GENERATING DIAGNOSTIC HYPOTHESES BASED ON BIOMEDICAL SIGNAL DATA", the entirety of which is incorporated herein by reference. In one or more embodiments, one or more historic queries may be incorporated into medical training data 116 upon validation. In one or more embodiments, medical training data may be retrieved from one or more databases, EHRs, and/or other repositories of similar nature, or be supplied as one or more user inputs. In one or more embodiments, at least a portion of medical training data may be added, deleted, replaced, or otherwise updated as a function of one or more inputs from one or more users.

With continued reference to FIG. 1, in one or more embodiments, at least an observation machine learning model 128*a-n* may include a transformer-based machine learning model 130. For the purposes of this disclosure, a "transformer-based machine learning model" is a machine learning model that includes a transformer architecture. While other types of machine learning models may process elements in an input independently and/or sequentially, a transformer-based machine learning model may capture dependencies and relationships between inputs using attention mechanisms 132, as described below in this disclosure. In one or more embodiments, the sequence in which inputs are received may be used by transformer-based machine learning model 130 to determine an output. In one or more embodiments, transformer-based machine learning model 130 may be used to handle sequential data, such as textual data, by capturing relationships between words or tokens in an input sequence. As a nonlimiting example, transformer-based machine learning model 130 may be configured to capture the importance of a first medication given prior to a second medication being given as indicated within reference EHR 108. In one or more embodiments, transformer-based machine learning models 130 may be used to capture trends within sequences of input data, find anomalies therein, and the like. In one or more embodiments, transformer-based machine learning model 130 may be trained to associate various input tokens with output tokens based on a context provided by other input tokens; such contextual understanding may allow the transformer-based machine learning model 130 to assign a higher importance to various input tokens based on their relevance.

With continued reference to FIG. 1, in some cases, transformer-based machine learning model 130 may be configured to capture temporal interdependencies 134 within plurality of reference factors 120 using attention mechanisms 132. For the purposes of this disclosure, a "temporal interdependency" is a time-based relationship between two data elements. As a nonlimiting example, temporal interdependency 134 may include a relationship between two sequential data elements, such as a diagnosis and a medication that follows the diagnosis. In one or more embodiments, temporal interdependency 134 may be determined by one or more temporal features 122 associated with reference factor 120, consistent with details described above. In one or more embodiments, processor 102 and/or transformer-based machine learning model 130 may be configured to capture temporal interdependencies 134 to make one or more determinations. In one or more embodiments, transformer-based machine learning model 130 may identify temporal interdependencies 134 and generate outputs and/or probabilities as a function of the temporal interdependencies 134, as described below. In one or more embodiments, a plurality of temporal interdependencies 134 may contain associated parameter values, wherein each temporal interdependency 134 may affect an output of transformer-based machine learning model 130. For the purposes of this disclosure, a "parameter value" is an internal variable generated by a machine learning model using training data in order to perform one or more of functions of the machine learning model. In one or more embodiments, transformer-based machine learning model 130 may generate outputs based on parameter values associated with temporal interdependencies 134. In one or more embodiments, temporal interdependencies 134 may be determined by associated temporal features 122 of reference factor 120. In one or more embodiments, transformer-based machine learning model 130 may identify temporal interdependencies 134 and generate outputs and/or probabilities as a function of the temporal interdependencies 134. In one or more embodiments, temporal interdependencies 134 may contain associated parameter values so that each temporal interdependency 134 may affect an output of transformer-based machine learning model 130. In one or more embodiments, transformer-based machine learning model 130 may be configured to identify reference factors 120, determine temporal features 122 as a function of the reference factors 120, and capture temporal interdependencies 134 as a function of the reference factors 120 and the temporal features 122. In one or more embodiments, transformer-based machine learning model 130 may generate outputs based on parameter values associated with temporal interdependencies 134.

With continued reference to FIG. 1, for the purposes of this disclosure, an "attention mechanism" is a part of a neural network architecture that enables a system to dynamically quantify relevant features of input data. Attention mechanism 132 may include any attention mechanism 132 as described in this disclosure. In one or more embodiments, attention mechanism 132 may help transformer-based machine learning model 130 understand the importance of an element with respect to its placement within a sequence. In one or more embodiments, in the context of medicine, attention mechanism 132 may be used to identify relationships between elements within reference EHR 108. In one or more embodiments, attention mechanisms 132 may focus on distinct relationships within reference EHR 108, such as without limitation, medications taken, treatment given, diagnosis made, and/or the like. In one or more embodiments, attention mechanism 132 may weigh the importance of each temporal feature 122 in a sequence of temporal features 122 relative to one another, wherein the attention mechanism 132 may be configured to capture long-range dependencies. In one or more embodiments, transformer-based machine learning model 130 may utilize attention mechanism 132 to weigh the importance of words and/or temporal interdependencies 134 in a sequence in order to make determinations or predictions.

With continued reference to FIG. 1, in some cases, capturing temporal interdependencies 134 within plurality of reference factors 120 may include generating an attention score 136 as a function of at least a reference factor 120 of the plurality of reference factors 120. Accordingly, training at least an observation machine learning model 128a-n may include updating transformer-based machine learning model 130 as a function of attention score 136. For the purposes of this disclosure, an "attention score" is a value associated with the strength of the relationship between an element and other elements within a sequence. The element described herein may be a word, a group of words, or a token of similar nature. Attention score 136 may include any attention score as described in this disclosure. In one or more embodiments, attention score 136 may be used to determine the relevance and/or importance of each data element within an input relative to others. In one or more embodiments, attention score 136 may be used to determine how much focus each input should receive when generating a particular output. In one or more embodiments, attention score 136 may be generated using a scoring function, such as a dot product or a learned function. In one or more embodiments, attention score 136 may be normalized across input tokens to obtain an attention weight. In one or more embodiments, attention score 136 may allow for transformer-based machine learning model 130 to selectively attend to relevant information within inputs in order to generate more accurate outputs. In one or more embodiments, attention score 136 may allow for transformer-based machine learning model 130 to determine the importance or relevance of each input token. As a nonlimiting example, inputs tokens assigned with higher attention scores 136 may be more relevant in the determination of outputs. In one or more embodiments, during training, transformer-based machine learning model 130 may be configured to adjust one or more of its parameters using task specific objectives, such as prediction of a case of pulmonary hypertension. In one or more embodiments, attention mechanism 132 may be trained to weigh input tokens based on their relevance or attention scores 136, as described below. Additional embodiments of transformer-based machine learning model 130 will be provided below in this disclosure. A person of ordinary skill in the art, upon reviewing the entirety of this disclosure, will be able to recognize suitable means to implement transformer-based machine learning model 130 and its related aspects for system 100.

With continued reference to FIG. 1, in one or more embodiments, at least an observation machine learning model 128*a-n* may include a contrastive machine learning model 138. For the purposes of this disclosure, a "contrastive machine learning model" is a machine learning model configured to extract meaningful representations from unlabeled data by mapping similar instances close together in a latent space while pushing apart dissimilar instances. In some cases, correlating plurality of reference features 118 and plurality of reference factors 120 may include pairing plurality of reference EHRs with plurality of reference cardiac data elements 112 using contrastive machine learning model 138. Details described herein regarding contrastive machine learning models may be consistent with any details disclosed in disclosed in U.S. patent application Ser. No. 18/230,043, filed on Dec. 21, 2023, entitled "APPARATUS AND A METHOD FOR GENERATING A DIAGNOSTIC LABEL", the entirety of which is incorporated herein by reference. As a nonlimiting example, contrastive machine learning model 138 may include a Contrastive VIsual Representation Learning from Text (ConVIRT) framework configured to learn visual representations by exploiting naturally occurring pairing of images and textual data. Additional details of contrastive machine learning model 138 will be provided below in this disclosure. A person of ordinary skill in the art, upon reviewing the entirety of this disclosure, will be able to recognize suitable means to implement contrastive machine learning model 138 and its related aspects for system 100.

With continued reference to FIG. 1, in one or more embodiments, training at least an observation machine learning model 128*a-n* may include training the at least an observation machine learning model 128*a-n* as a function of time series data 110, as described above, by assigning a weight 140 to each temporal feature 122 of the plurality of temporal features 122. For the purposes of this disclosure, a "weight" is an indication that indicates the importance of an input relative to its associated output. As nonlimiting examples, weight 140 may be assigned to various reference factors 120 such as medications, treatments, lab results, and the like. In one or more embodiments, weight 140 may be assigned based on a relationship between reference factor 120 and its corresponding temporal feature 122. In one or more embodiments, observation machine learning model 128*a-n* may be trained to determine weight 140 for each temporal feature 122, wherein the observation machine learning model 128*a-n* may use such weight 140 as part of its input when determining its outputs. In one or more embodiments, observation machine learning model 128*a-n* may determine relationships between reference factors 120 based on their temporal features 122. In one or more embodiments, observation machine learning model 128*a-n* may determine a relationship between reference factors 120 within a sequence.

With continued reference to FIG. 1, in one or more embodiments, training observation machine learning model 128*a-n* may include generating a plurality of diagnostic labels 142 as a function of a plurality of correlations between plurality of reference features 118 and plurality of reference factors 120. For the purposes of this disclosure, a "diagnostic label" is a label used for identification of a data element a diagnostic process. For the purposes of this disclosure, "labeling" is a process of identifying raw data and adding one or more meaningful and informative labels to provide a context for one or more following steps. For the purposes of this disclosure, a "label" is an indication describing one or more characteristics of a subject matter as well as how the subject matter is categorized into one or more categories with respect to a population or sub-population containing the subject. As nonlimiting examples, subject matter described herein may include one or more reference features 118 and/or one or more reference factors 120. In one or more embodiments, diagnostic label 142 may include a binary diagnostic label, e.g., "likely" vs. "unlikely" or "positive" vs. "negative". In one or more embodiments, diagnostic label 142 may be further specified, such as "highly likely", "highly unlikely", "abnormally high", or "abnormally low". In one or more embodiments, diagnostic label 142 may be associated with a percentile ranking, e.g., "top 10% of the population". In one or more embodiments, diagnostic label 142 may be applied with respect to at least a specific cohort upon application of one or more inclusion/exclusion criteria, such as "top 25% of the female population". In some cases, generating plurality of diagnostic labels 142 as a function of plurality of correlations may include analyzing the statistical distribution of plurality of reference features 118 and/or reference factors 120, as described below.

With continued reference to FIG. 1, in one or more embodiments, processor 102 may perform one or more functions of system 100, such as isolation of plurality of reference factors 120, by using optical character recognition (OCR) to read digital files and extract information therefrom. In one or more embodiments, OCR may include automatic conversion of images (e.g., typed, handwritten, or printed text) into machine-encoded text. In one or more embodiments, recognition of at least a keyword from an image component may include one or more processes, including without limitation OCR, optical word recognition, intelligent character recognition, intelligent word recognition, and the like. In one or more embodiments, OCR may recognize written text one glyph or character at a time, for example, for languages that use a space as a word divider. In one or more embodiments, intelligent character recognition (ICR) may recognize written text one glyph or character at a time, for instance by employing machine learning processes. In one or more embodiments, intelligent word recognition (IWR) may recognize written text, one word at a time, for instance by employing machine learning processes.

With continued reference to FIG. 1, in one or more embodiments, OCR may employ preprocessing of image components. Preprocessing process may include without limitation de-skew, de-speckle, binarization, line removal, layout analysis or "zoning", line and word detection, script recognition, character isolation or "segmentation", and normalization. In one or more embodiments, a de-skew process may include applying a transform (e.g., homography or affine transform) to an image component to align text. In one or more embodiments, a de-speckle process may include removing positive and negative spots and/or smoothing edges. In one or more embodiments, a binarization process may include converting an image from color or greyscale to black-and-white (i.e., a binary image). Binarization may be performed as a simple way of separating text (or any other desired image component) from the background of image component. In one or more embodiments, binarization may be required for example if an employed OCR algorithm only works on binary images. In one or more embodiments, line removal process may include removal of non-glyph or non-character imagery (e.g., boxes and lines). In one or more embodiments, a layout analysis or "zoning" process may identify columns, paragraphs, captions, and the like as distinct blocks. In one or more embodiments, a line and word detection process may establish a baseline for word and character shapes and separate words, if necessary. In one or more embodiments, a script recognition process may, for example in multilingual documents, identify a script, allowing an appropriate OCR algorithm to be selected. In one or more embodiments, a character isolation or "segmentation" process may separate signal characters, for example, character-based OCR algorithms. In one or more embodiments, a normalization process may normalize the aspect ratio and/or scale of image component.

With continued reference to FIG. 1, in one or more embodiments, an OCR process may include an OCR algorithm. Exemplary OCR algorithms include matrix-matching processes and/or feature extraction processes. Matrix matching may involve comparing an image to a stored glyph on a pixel-by-pixel basis. In one or more embodiments, matrix matching may also be known as "pattern matching", "pattern recognition", and/or "image correlation". Matrix matching may rely on an input glyph being correctly isolated from the rest of image component. Matrix matching may also rely on a stored glyph being in a similar font and at the same scale as input glyph.

With continued reference to FIG. 1, in one or more embodiments, an OCR process may include a feature extraction process. In one or more embodiments, feature extraction may decompose a glyph into features. Exemplary nonlimiting features may include corners, edges, lines, closed loops, line direction, line intersections, and the like. In one or more embodiments, feature extraction may reduce the dimensionality of representation and may make the recognition process computationally more efficient. In one or more embodiments, extracted features can be compared with an abstract vector-like representation of a character, which might be reduced to one or more glyph prototypes. General techniques of feature detection in computer vision are applicable to this type of OCR. In one or more embodiments, machine learning process like nearest neighbor classifiers (e.g., k-nearest neighbors algorithm) can be used to compare image features with stored glyph features and choose a nearest match. OCR may employ any machine learning process described in this disclosure. Exemplary nonlimiting OCR software includes Cuneiform and Tesseract. Cuneiform is a multi-language, open-source OCR system originally developed by Cognitive Technologies of Moscow, Russia. Tesseract is a free OCR software originally developed by Hewlett-Packard of Palo Alto, California, United States.

With continued reference to FIG. 1, in one or more embodiments, OCR may employ a two-pass approach to character recognition. Second pass may include adaptive recognition and use letter shapes recognized with high confidence on a first pass to better recognize remaining letters on a second pass. In one or more embodiments, two-pass approach may be advantageous for unusual fonts or low-quality image components where visual verbal content may be distorted. Another exemplary OCR software tool includes OCRopus. The development of OCRopus is led by the German Research Center for Artificial Intelligence in Kaiserslautern, Germany. In one or more embodiments, OCR software may employ neural networks, for example, deep neural networks, as described in this disclosure below.

With continued reference to FIG. 1, in one or more embodiments, OCR may include post-processing. For example, OCR accuracy can be increased, in some cases, if output is constrained by a lexicon. A lexicon may include a list or set of words that are allowed to occur in a document. In one or more embodiments, a lexicon may include, for instance, all the words in the English language, or a more technical lexicon for a specific field. In some cases, an output stream may be a plain text stream or file of characters. In one or more embodiments, an OCR may preserve an original layout of visual verbal content. In one or more embodiments, near-neighbor analysis can make use of co-occurrence frequencies to correct errors by noting that certain words are often seen together. For example, "Washington, D.C." is generally far more common in English than "Washington DOC". In one or more embodiments, an OCR process may make use of a priori knowledge of grammar for a language being recognized. For example, OCR process may apply grammatical rules to help determine if a word is likely to be a verb or a noun. Distance conceptualization may be employed for recognition and classification. For example, a Levenshtein distance algorithm may be used in OCR post-processing to further optimize results. A person of ordinary skill in the art will recognize how to apply the aforementioned technologies to extract information from a digital file upon reviewing the entirety of this disclosure.

With continued reference to FIG. 1, in one or more embodiments, a computer vision module configured to perform one or more computer vision tasks such as, without limitation, object recognition, feature detection, edge/corner detection thresholding, or machine learning process may be used to recognize specific features or attributes. For the purposes of this disclosure, a "computer vision module" is a computational component designed to perform one or more computer vision, image processing, and/or modeling tasks. In one or more embodiments, computer vision module may receive one or more digital files containing one or more reference features 118 or reference factors 120 from a data repository and generate one or more diagnostic labels 142 therefrom. In one or more embodiments, to generate a plurality of diagnostic labels 142, computer vision module may be configured to compare one or more reference features 118 or reference factors 120 against the statistical data of the one or more reference features 118 or reference factors 120 and attach one or more diagnostic labels 142 as a function of the comparison, as described above.

With continued reference to FIG. 1, in one or more embodiments, computer vision module may include an image processing module, wherein images may be pre-processed using the image processing module. For the purposes of this disclosure, an "image processing module" is a component designed to process digital images such as images described herein. For example, and without limitation, image processing module may be configured to compile a plurality of images of a multi-layer scan to create an integrated image. In one or more embodiments, image processing module may include a plurality of software algorithms that can analyze, manipulate, or otherwise enhance an image, such as, without limitation, a plurality of image processing techniques as described below. In one or more embodiments, computer vision module may also include hardware components such as, without limitation, one or more graphics processing units (GPUs) that can accelerate the processing of a large number of images. In one or more embodiments, computer vision module may be implemented with one or more image processing libraries such as, without limitation, OpenCV, PIL/Pillow, ImageMagick, and the like. In a nonlimiting example, in order to generate one or more labels and/or recognize one or more reference attributes, one or more image processing tasks, such as noise reduction, contrast enhancement, intensity normalization, image segmentation, and/or the like, may be performed by computer vision module on a plurality of images to isolate certain features or components from the rest. In one or more embodiments, one or more machine learning models may be used to perform segmentations, for example, and without limitation, a U-net (i.e., a convolution neural network containing a contracting path as an encoder and an expansive path as a decoder, wherein the encoder and the decoder forms a U-shaped structure). A person of ordinary skill in the art, upon reviewing the entirety of this disclosure, will be aware of various image processing, computer vision, and modeling tasks that may be performed by processor 102.

With continued reference to FIG. 1, in one or more embodiments, one or more functions of system 100 may involve a use of image classifiers to classify images within any data described in this disclosure. For the purposes of this disclosure, an "image classifier" is a machine learning model that sort inputs of image information into categories or bins of data, outputting the categories or bins of data and/or labels associated therewith. Image Classifier may include a mathematical model, a neural net, or a program generated by a machine learning algorithm known as a "classification algorithm", as described in further detail below. Image classifier may be configured to output at least a datum that labels or otherwise identifies a set of images that are clustered together, found to be close under a distance metric as described below, or the like. Computing device and/or another device may generate image classifier using a classification algorithm. For the purposes of this disclosure, a classification algorithm is a process whereby computing device derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, Fisher's linear discriminant, quadratic classifiers, decision trees, boosted trees, random forest classifiers, learning vector quantization, and/or neural network-based classifiers. In one or more embodiments, processor 102 may use image classifier to identify a key image in any data described in this disclosure. For the purposes of this disclosure, a "key image" is an element of visual data used to identify and/or match elements to each other. In one or more embodiments, key image may include part of a medical image such as an ECG, a CT scan, an MRI scan, or the like, with features that unambiguously identify the type of the medical image. Image classifier may be trained with binarized visual data that have already been classified to determine key images in any other data described in this disclosure. For the purposes of this disclosure, "binarized visual data" are visual data that are described in a binary format. For example, binarized visual data of a photo may include ones and zeroes, wherein the specific sequence of ones and zeros may be used to represent the photo. Binarized visual data may be used for image recognition wherein a specific sequence of ones and zeroes may indicate a product present in the image. An image classifier may be consistent with any classifier as discussed herein. An image classifier may receive input data (e.g., a query) described in this disclosure and output a key image with the data. In one or more embodiments, image classifier may be used to compare visual data in one data set, such as one or more images submitted with a query, with visual data in another data set, such as one or more images within data repository 106, as described above.

With continued reference to FIG. 1, processor 102 may be configured to perform feature extraction on one or more images within data repository 106, as described above. For the purposes of this disclosure, "feature extraction" is a process of transforming an initial data set into informative measures and values. For example, feature extraction may include a process of determining one or more geometric features of an anatomic structure. In one or more embodiments, feature extraction may be used to determine one or more spatial relationships within a drawing that may be used to uniquely identify one or more features. In one or more embodiments, processor 102 may be configured to extract one or more regions of interest, wherein the regions of interest may be used to extract one or more features using one or more feature extraction techniques.

With continued reference to FIG. 1, processor 102 may be configured to perform one or more of its functions, such as extraction of reference features 118, as described above, using a feature learning algorithm. For the purposes of this disclosure, a "feature learning algorithm" is a machine learning algorithm that identifies associations between elements of data in a data set, where particular outputs and/or inputs are not specified. Data set may include without limitation a training data set. For instance, and without limitation, a feature learning algorithm may detect co-occurrences of elements of data, as defined above, with each other. Computing device may perform feature learning algorithm by dividing elements or sets of data into various sub-combinations of such data to create new elements of data and evaluate which elements of data tend to co-occur with which other elements. In one or more embodiments, feature learning algorithm may perform clustering of data.

With continued reference to FIG. 1, feature learning and/or clustering algorithm may be implemented, as a non-limiting example, using a k-means clustering algorithm. For the purposes of this disclosure, a "k-means clustering algorithm" is a type of cluster analysis that partitions n observations or unclassified cluster data entries into k clusters in which each observation or unclassified cluster data entry belongs to the cluster with the nearest mean. For the purposes of this disclosure, "cluster analysis" is a process that includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering, whereby each observation or unclassified cluster data entry belongs to a cluster or not. Cluster analysis may include soft clustering or fuzzy clustering, whereby each observation or unclassified cluster data entry belongs to each cluster to a certain degree such as for example a likelihood of belonging to a cluster; for instance, and without limitation, a fuzzy clustering algorithm may be used to identify clustering of elements of a first type or category with elements of a second type or category, and vice versa, as described below. Cluster analysis may include strict partitioning clustering, whereby each observation or unclassified cluster data entry belongs to exactly one cluster. Cluster analysis may include strict partitioning clustering with outliers, whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering, whereby observations or unclassified cluster data entries that belong to a child cluster also belong to a parent cluster.

With continued reference to FIG. 1, computing device may generate a k-means clustering algorithm by receiving unclassified data and outputting a definite number of classified data entry clusters, wherein the data entry clusters each contain cluster data entries. K-means algorithm may select a specific number of groups or clusters to output, identified by a variable "k". Generating k-means clustering algorithm includes assigning inputs containing unclassified data to a "k-group" or "k-cluster" based on feature similarity. Centroids of k-groups or k-clusters may be utilized to generate classified data entry cluster. K-means clustering algorithm may select and/or be provided "k" variable by calculating k-means clustering algorithm for a range of k values and comparing results. K-means clustering algorithm may compare results across different values of k as the mean distance between cluster data entries and cluster centroid. K-means clustering algorithm may calculate mean distance to a centroid as a function of k value, and the location of where the rate of decrease starts to sharply shift, which may be utilized to select a k value. Centroids of k-groups or k-cluster include a collection of feature values which are utilized to classify data entry clusters containing cluster data entries. K-means clustering algorithm may act to identify clusters of closely related data, which may be provided with user cohort labels; this may, for instance, generate an initial set of user cohort labels from an initial set of data, and may also, upon subsequent iterations, identify new clusters to be provided new labels, to which additional data may be classified, or to which previously used data may be reclassified.

With continued reference to FIG. 1, generating a k-means clustering algorithm may include generating initial estimates for k centroids which may be randomly generated or randomly selected from unclassified data input. K centroids may be utilized to define one or more clusters. K-means clustering algorithm may assign unclassified data to one or more k-centroids based on the squared Euclidean distance by first performing a data assigned step of unclassified data. K-means clustering algorithm may assign unclassified data to its nearest centroid based on the collection of centroids $c_i$ of centroids in set C. Unclassified data may be assigned to a cluster based on $\text{argmin}_{c_i \ni C} \text{dist}(c_i, x)^2$, where argmin includes argument of the minimum, $c_i$ includes a collection of centroids in a set C, and dist includes standard Euclidean distance. K-means clustering module may then recompute centroids by taking a mean of all cluster data entries assigned to a centroid's cluster. This may be calculated based on $c_i = 1/|S_i| \Sigma x_i \ni S_i^{xi}$. K-means clustering algorithm may continue to repeat these calculations until a stopping criterion has been satisfied such as when cluster data entries do not change clusters, the sum of the distances have been minimized, and/or some maximum number of iterations has been reached.

With continued reference to FIG. 1, k-means clustering algorithm may be configured to calculate a degree of similarity index value. For the purposes of this disclosure, a "degree of similarity index value" is a distance measured between each data entry cluster generated by k-means clustering algorithm and a selected element. Degree of similarity index value may indicate how close a particular combination of elements is to being classified by k-means algorithm to a particular cluster. K-means clustering algorithm may evaluate the distances of the combination of elements to the k-number of clusters output by k-means clustering algorithm. Short distances between an element of data and a cluster may indicate a higher degree of similarity between the element of data and a particular cluster. Longer distances between an element and a cluster may indicate a lower degree of similarity between the element to be compared and/or clustered and a particular cluster.

With continued reference to FIG. 1, k-means clustering algorithm selects a classified data entry cluster as a function of the degree of similarity index value. In one or more embodiments, k-means clustering algorithm may select a classified data entry cluster with the smallest degree of similarity index value indicating a high degree of similarity between an element and the data entry cluster. Alternatively or additionally, k-means clustering algorithm may select a plurality of clusters having low degree of similarity index values to elements to be compared and/or clustered thereto, indicative of greater degrees of similarity. Degree of similarity index values may be compared to a threshold number indicating a minimal degree of relatedness suitable for inclusion of a set of element data in a cluster, where degree of similarity indices a-n falling under the threshold number may be included as indicative of high degrees of relatedness. The above-described illustration of feature learning using k-means clustering is included for illustrative purposes only and should not be construed as limiting potential implementation of feature learning algorithms; a person of ordinary skills in the art, upon reviewing the entirety of this disclosure, will be aware of various additional or alternative feature learning approaches, such as particle swarm optimization (PSO) and generative adversarial network (GAN) that may be used consistently with this disclosure.

With continued reference to FIG. 1, in one or more embodiments, processor 102 may use an image recognition algorithm to determine patterns within an image. In one or more embodiments, image recognition algorithm may include an edge-detection algorithm, which may detect one or more shapes defined by edges. For the purposes of this disclosure, an "edge detection algorithm" is or includes a mathematical method that identifies points in a digital image at which the image brightness changes sharply and/or has discontinuities. In one or more embodiments, such points may be organized into straight and/or curved line segments, which may be referred to as "edges". Edge detection may be performed using any suitable edge detection algorithm, including without limitation Canny edge detection, Sobel operator edge detection, Prewitt operator edge detection, Laplacian operator edge detection, and/or differential edge detection. Edge detection may include phase congruency-based edge detection, which finds all locations of an image where all sinusoids in the frequency domain, for instance when generated using a Fourier decomposition, may have matching phases which may indicate a location of an edge.

With continued reference to FIG. 1, in one or more embodiments, generation of medical training data 116, as described above, may be implemented by training a large language model (LLM) using a large set of medical literature; in some cases, training LLM using large set of medical literature may include first pre-training the LLM on a general set of medical literatures; and fine-tuning the LLM on a special set of medical literature, wherein both the general set of medical literature and the special set of medical literature are subsets of the large set of medical literature. For the purposes of this disclosure, a "large language model" is a deep learning data structure that can recognize, summarize, translate, predict and/or generate text and other content based on knowledge gained from massive datasets. LLMs may be trained on large sets of data. Training sets may be drawn from diverse sets of data such as, as nonlimiting examples, scientific journal articles, medical report documents, EHRs, entity documents, business documents, inventory documentation, emails, user communications, advertising documents, newspaper articles, and the like. In some embodiments, training sets of an LLM may include information from one or more public or private databases. As a nonlimiting example, training sets may include databases associated with an entity. In some embodiments, training sets may include portions of documents associated with the electronic records correlated to examples of outputs. In one or more embodiments, LLM may include one or more architectures based on capability requirements of the LLM. Exemplary architectures may include, without limitation, Generative Pretrained Transformer (GPT), Bidirectional Encoder Representations from Transformers (BERT), Text-To-Text Transfer Transformer (T5), and the like. Architecture choice may depend on a needed capability such generative, contextual, or other specific capabilities.

With continued reference to FIG. 1, in one or more embodiments, LLM may be generally trained. For the purposes of this disclosure, a "generally trained" LLM is a LLM that is trained on a general training set including a variety of subject matters, data sets, and fields. In one or more embodiments, LLM may be initially generally trained. Additionally or alternatively, LLM may be specifically trained. For the purposes of this disclosure, a "specifically trained" LLM is a LLM that is trained on a specific training set, wherein the specific training set includes data including specific correlations for the LLM to learn. As a nonlimiting example, LLM may be generally trained on a general training set, then specifically trained on a specific training set. In one or more embodiments, generally training LLM may be performed using unsupervised machine learning process. In one or more embodiments, specific training of LLM may be performed using supervised machine learning process. As a nonlimiting example, specific training set may include information from a database. As a nonlimiting example, specific training set may include text related to the users such as user specific data for electronic records correlated to examples of outputs. In one or more embodiments, training one or more machine learning models may include setting the parameters of the one or more models (weights and biases) either randomly or using a pretrained model. Generally training one or more machine learning models on a large corpus of text data can provide a starting point for fine-tuning on a specific task. A model such as LLM may learn by adjusting its parameters during the training process to minimize a defined loss function, which measures the difference between predicted outputs and ground truth. Once model has been generally trained, the model may then be specifically trained to fine-tune the pretrained model on task-specific data to adapt it to the target task. Fine-tuning may involve training model with task-specific training data, adjusting the model's weights to optimize performance for the particular task. In some cases, this may include optimizing model's performance by fine-tuning hyperparameters such as learning rate, batch size, and regularization. Hyperparameter tuning may help in achieving the best performance and convergence during training. In one or more embodiments, fine-tuning pretrained model such as LLM may include fine-tuning the pretrained model using Low-Rank Adaptation (LoRA). For the purposes of this disclosure, "Low-Rank Adaptation" is a training technique for large language models that modifies a subset of parameters in the model. Low-Rank Adaptation may be configured to make the training process more computationally efficient by avoiding a need to train an entire model from scratch. In an exemplary embodiment, a subset of parameters that are updated may include parameters that are associated with a specific task or domain.

With continued reference to FIG. 1, in one or more embodiments, LLM may include and/or be produced using Generative Pretrained Transformer (GPT), GPT-2, GPT-3, GPT-4, and the like. GPT, GPT-2, GPT-3, GPT-3.5, and GPT-4 are products of Open AI Inc., of San Francisco, CA. LLM may include a text prediction-based algorithm configured to receive an article and apply a probability distribution to the words already typed in a sentence to work out the most likely word to come next in augmented articles. For example, if some words that have already been typed are "electronic health", then it may be highly likely that the word "record" will come next. LLM may output such predictions by ranking words by likelihood or a prompt parameter. For the example given above, LLM may score "record" as the most likely, "records" as the next most likely, "profile" or "profiles" next, and the like. LLM may include an encoder component and a decoder component.

With continued reference to FIG. 1, LLM may include a transformer architecture. In some embodiments, encoder component of LLM may include transformer architecture. A "transformer architecture," for the purposes of this disclosure is a neural network architecture that uses self-attention and positional encoding. Transformer architecture may be designed to process sequential input data, such as natural language, with applications towards tasks such as translation and text summarization. Transformer architecture may process the entire input all at once. For the purposes of this disclosure, "positional encoding" is a data processing technique that encodes the location or position of an entity in a sequence. In some embodiments, each position in the sequence may be assigned a unique representation. In some embodiments, positional encoding may include mapping each position in the sequence to a position vector. In some embodiments, trigonometric functions, such as sine and cosine, may be used to determine the values in the position vector. In some embodiments, position vectors for a plurality of positions in a sequence may be assembled into a position matrix, wherein each row of position matrix may represent a position in the sequence.

With continued reference to FIG. 1, LLM and/or transformer architecture may include an attention mechanism. For the purposes of this disclosure, an "attention mechanism" is a part of a neural architecture that enables a system to dynamically quantify relevant features of the input data. In the case of natural language processing, input data may be a sequence of textual elements. It may be applied directly to the raw input or to its higher-level representation.

With continued reference to FIG. 1, attention mechanism may represent an improvement over a limitation of an encoder-decoder model. An encoder-decoder model encodes an input sequence to one fixed length vector from which the output is decoded at each time step. This issue may be seen as a problem when decoding long sequences because it may make it difficult for the neural network to cope with long sentences, such as those that are longer than the sentences in the training corpus. Applying attention mechanism, LLM may predict next word by searching for a set of positions in a source sentence where the most relevant information is concentrated. LLM may then predict next word based on context vectors associated with these source positions and all the previously generated target words, such as textual data of a dictionary correlated to a prompt in a training data set. For the purposes of this disclosure, "context vectors" are fixed-length vector representations useful for document retrieval and word sense disambiguation.

With continued reference to FIG. 1, attention mechanism may include, without limitation, generalized attention, self-attention, multi-head attention, additive attention, global attention, and the like. In generalized attention, when a sequence of words or an image is fed to LLM, it may verify each element of input sequence and compare it against the output sequence. Each iteration may involve the mechanism's encoder capturing input sequence and comparing it with each element of the decoder's sequence. From the comparison scores, attention mechanism may then select the words or parts of image that it needs to pay attention to. In self-attention, LLM may pick up particular parts at different positions in input sequence and over time compute an initial composition of output sequence. In multi-head attention, LLM may include a transformer model of an attention mechanism. Attention mechanisms, as described above, may provide context for any position in input sequence. For example, if the input data is a natural-language sentence, the transformer does not have to process one word at a time. In multi-head attention, computations by LLM may be repeated over several iterations, and each computation may form parallel layers known as attention heads. Each separate head may independently pass input sequence and corresponding output sequence element through separate head. A final attention score may be produced by combining attention scores at each head so that every nuance of input sequence is taken into consideration. In additive attention (Bahdanau attention mechanism), LLM may make use of attention alignment scores based on a number of factors. Alignment scores may be calculated at different points in neural network, and/or at different stages represented by discrete neural networks. Source or input sequence words are correlated with target or output sequence words but not to an exact degree. This correlation may take into account all hidden states and the final alignment score is the summation of a matrix of alignment scores. In global attention (Luong mechanism), in situations where neural machine translations are required, LLM may either attend to all source words or predict the target sentence, thereby attending to a smaller subset of words.

With continued reference to FIG. 1, multi-headed attention in encoder may apply a specific attention mechanism called self-attention. Self-attention allows models such as LLM or components thereof to associate each word in input, to other words. As a nonlimiting example, LLM may learn to associate the word "you", with "how" and "are". It's also possible that LLM learns that words structured in this pattern are typically a question and to respond appropriately. In one or more embodiments, to achieve self-attention, input may be fed into three distinct and fully connected neural network layers to create query, key, and value vectors. Query, key, and value vectors may be fed through a linear layer; then, the query and key vectors may be multiplied using dot product matrix multiplication in order to produce a score matrix. Score matrix may determine the amount of focus for a word that should be put on other words (thus, each word may be a score that corresponds to other words in the time-step). The values in score matrix may be scaled down. As a nonlimiting example, score matrix may be divided by the square root of the dimension of the query and key vectors. In one or more embodiments, a softmax of the scaled scores in score matrix may be taken. The output of this softmax function may be called attention weights. Attention weights may be multiplied by your value vector to obtain an output vector, wherein the output vector may then be fed through a final linear layer.

With continued reference to FIG. 1, in order to use self-attention in a multi-headed attention computation, query, key, and value may be split into N vectors before applying self-attention. Each self-attention process may be called a "head". Each head may produce an output vector and each output vector from each head may be concatenated into a single vector. This single vector may then be fed through final linear layer discussed above. In theory, each head can learn something different from input, therefore giving the encoder model more representation power.

With continued reference to FIG. 1, encoder of transformer may include a residual connection. Residual connection may include adding the output from multi-headed attention to the positional input embedding. In one or more embodiments, an output from residual connection may go through a layer normalization. In one or more embodiments, a normalized residual output may be projected through a pointwise feed-forward network for further processing. Pointwise feed-forward network may include a couple of linear layers with a ReLU activation in between. Output may then be added to an input of the pointwise feed-forward network and further normalized.

With continued reference to FIG. 1, transformer architecture may include a decoder. Decoder may a multi-headed attention layer, a pointwise feed-forward layer, one or more residual connections, and layer normalization (particularly after each sub-layer), as discussed in more detail above. In one or more embodiments, decoder may include two multi-headed attention layers. In one or more embodiments, decoder may be autoregressive. For the purposes of this disclosure, "autoregressive" means that the decoder takes in a list of previous outputs as inputs along with encoder outputs containing attention information from the input.

With continued reference to FIG. 1, in one or more embodiments, input to decoder may go through an embedding layer and positional encoding layer to obtain positional embeddings. Decoder may include a first multi-headed attention layer, wherein the first multi-headed attention layer may receive positional embeddings.

With continued reference to FIG. 1, first multi-headed attention layer may be configured to not condition to future tokens. As a nonlimiting example, when computing attention scores on the word "am", decoder should not have access to the word "fine" in "I am fine", because that word is a future word that was generated after. The word "am" should only have access to itself and the words before it. In one or more embodiments, this may be accomplished by implementing a look-ahead mask. Look ahead mask is a matrix of the same dimensions as a scaled attention score matrix that is filled with "0s" and negative infinities. For example, the top right triangle portion of look-ahead mask may be filled with negative infinities. Look-ahead mask may be added to scaled attention score matrix to obtain a masked score matrix. Masked score matrix may include scaled attention scores in the lower-left triangle of the matrix and negative infinities in the upper-right triangle of the matrix. Then, when a softmax of this matrix is taken, negative infinities will be zeroed out; this leaves zero attention scores for "future tokens."

With continued reference to FIG. 1, second multi-headed attention layer may use encoder outputs as queries and keys and outputs from the first multi-headed attention layer as values. This process matches encoder's input to the decoder's input, allowing the decoder to decide which encoder input is relevant to put a focus on. An output from second multi-headed attention layer may be fed through a pointwise feedforward layer for further processing.

With continued reference to FIG. 1, an output of the pointwise feedforward layer may be fed through a final linear layer. This final linear layer may act as a classifier. This classifier may be as big as the number of classes that you have. For example, if you have 10,000 classes for 10,000 words, output of that classifier will be of size 10,000. Output of this classifier may be fed into a softmax layer which may serve to produce probability scores between zero and one. An index may be taken of the highest probability score in order to determine a predicted word.

With continued reference to FIG. 1, decoder may take this output and add it to decoder inputs. Decoder may continue decoding until a token is predicted. Decoder may stop decoding once it predicts an end token.

With continued reference to FIG. 1, in one or more embodiments, decoder may be stacked N layers high, with each layer taking in inputs from encoder and layers before it. Stacking layers may allow LLM to learn to extract and focus on different combinations of attention from its attention heads.

With continued reference to FIG. 1, LLM may receive an input. Input may include a string of one or more characters. Inputs may additionally include unstructured data. For example, input may include one or more words, a sentence, a paragraph, a thought, a query, and the like. For the purposes of this disclosure, a "query" is a string of characters that poses a question. In one or more embodiments, input may be received from a user device. User device may be any computing device that is used by a user. As nonlimiting examples, user device may include desktops, laptops, smartphones, tablets, and the like. In one or more embodiments, input may include any set of data associated with training and/or using LLM. As a nonlimiting example, input may be a prompt such as "what abnormalities are present in the attached ECG signal?"

With continued reference to FIG. 1, LLM may generate at least one annotation as output. At least one annotation may be any annotation as described herein. In one or more embodiments, LLM may include multiple sets of transformer architecture as described above. Output may include a textual output. For the purposes of this disclosure, "textual output" is an output including a string of one or more characters. Textual output may include, for example, a plurality of annotations for unstructured data. In one or more embodiments, textual output may include a phrase or sentence identifying the status of a user query. In one or more embodiments, textual output may include a sentence or plurality of sentences describing a response to user query. As a nonlimiting example, this may include restrictions, timing, advice, dangers, benefits, and the like.

With continued reference to FIG. 1, processor 102 is configured to receive a query 144 pertaining to a subject, wherein the query 144 includes at least a query cardiac data element 146 and at least a query EHR 148. For the purposes of this disclosure, a "query cardiac data element" is a cardiac data element used as a query to match other data or information and/or to selectively retrieve data or information for use in further method steps as disclosed below in this disclosure. Query cardiac data element 146 may include any type of cardiac data element described in this disclosure that may be included as part of query 144. In one or more embodiments, at least a query cardiac data element 146 may include a query ECG 150, consistent with details described above. Similarly, for the purposes of this disclosure, a "query electronic health record (EHR)" is an electronic health record (EHR) used as a query to match other data or information and/or to selectively retrieve data or information for use in further method steps as disclosed below in this disclosure. Query EHR 148 may include any type of EHR described in this disclosure that may be used as part of query 144. Consistent with details described above regarding reference cardiac data element 112, reference EHR 108, reference feature 118, and reference factor 120, in some cases, query cardiac data element 146 may include one or more query features, and query EHR may include one or more query factors. As nonlimiting examples, query features and query factors may be extracted from query 144 using observation machine learning model 128*a-n*. For the purposes of this disclosure, a "subject" is a patient associated with query 144. In one or more embodiments, query 144 may be submitted by a medical professional using a user interface, as described below in this disclosure. In some cases, elements of query 144 may be assembled from a plurality of sources. As a nonlimiting example, query EHR 148 may be retrieved from data repository 106, a database, or another data store of similar nature, whereas query ECG may be received from signal capturing device, consistent with details described above in this disclosure.

With continued reference to FIG. 1, in one or more embodiments, system 100 may be communicatively connected to a signal capturing device configured to capture at least a query cardiac data element 146. For the purposes of this disclosure, a "signal capturing device" is a device configured to detect one or more signals. For the purposes of this disclosure, a "signal" is any intelligible representation of data. A signal may, for example and without limitation, transmit from one device to another. A signal may include an optical signal, a hydraulic signal, a pneumatic signal, a mechanical signal, an electric signal, a digital signal, an analog signal, and the like. In some cases, a signal may be used to communicate with a computing device, for example by way of one or more ports. In some cases, a signal may be transmitted and/or received by a computing device for example by way of an input/output port. An analog signal may be digitized, for example by way of an analog to digital converter. In some cases, an analog signal may be processed, for example by way of any analog signal processing steps described in this disclosure, prior to digitization. In some cases, a digital signal may be used to communicate between two or more devices, including without limitation computing devices. In some cases, a digital signal may be communicated by way of one or more communication protocols, including without limitation internet protocol (IP), controller area network (CAN) protocols, serial communication protocols (e.g., universal asynchronous receiver-transmitter [UART]), parallel communication protocols (e.g., IEEE 128 [printer port]), and the like.

With continued reference to FIG. 1, signal capturing device may include one or more detectors. For the purposes of this disclosure, a detector is a device configured to capture at least a signal including one or more features contained therein, as described above. In one or more embodiments, detector may be an electrical detector that detects one or more changes in electrical signal. Detector may include an ammeter, a voltmeter, and/or one or more variations thereof. As a nonlimiting example, a detector may include a plurality of electrodes configured to track a time-dependent action potential of a heart as heart muscles go through cycles of depolarizations and repolarizations; the result of such detection is an electrocardiogram (ECG), as described in detail above.

With continued reference to FIG. 1, processor 102 is configured to output at least an observation outcome 152a-n as a function of query 144 and at least an observation machine learning model 128a-n. For the purposes of this disclosure, an "observation outcome" is an identification, determination, or prediction made by system 100, based on query 144, regarding one or more aspects related to the well-being of subject. In one or more embodiments, observation outcome 152a-n may include one or more medical conditions or symptoms associated with subject that are not yet diagnosed or identified. In one or more embodiments, observation outcome 152a-n may include one or more predictive metrics that describe the likelihood of subject developing one or more medical conditions or symptoms in the future, such as 6 months, 12 months, or 18 months ahead. In one or more embodiments, observation outcome 152a-n may include one or more recommended courses of actions for subject to decrease the risk of developing certain medical conditions or symptoms, such as changes in exercise routines, dietary habits, dosages of medications or dietary supplements, among others.

With continued reference to FIG. 1, as a nonlimiting example, outputting at least an observation outcome 152a-n may include outputting at least a likelihood of subject developing a case of chronic obstructive pulmonary disease (COPD). For the purposes of this disclosure, "chronic obstructive pulmonary disease (COPD)" is a type of lung disease that results in a restricted airflow and causes difficulties in breathing. A common complication of COPD is pulmonary hypertension (PH). For the purposes of this disclosure, "pulmonary hypertension (PH)" is a type of high blood pressure that affects pulmonary arteries and the right side of the heart. Details regarding pulmonary hypertension and/or its implications may be consistent with any detail disclosed in U.S. patent application Ser. No. 17/500,287, filed on Jan. 30, 2024, and entitled "NONINVASIVE METHODS FOR DETECTION OF PULMONARY HYPERTENSION", the entirety of each of which is incorporated herein by reference. As a nonlimiting example, a pulmonary artery pressure that exceeds 35 mmHg, 50 mmHg, or 70 mmHg may be classified as mild, moderate, and severe cases of pulmonary hypertension respectively.

With continued reference to FIG. 1, in one or more embodiments, outputting at least an observation outcome 152a-n may include calculating at least a distance metric 154 between the at least a query cardiac data element 146, such as at least a query ECG 150, and each reference cardiac data element 112 of plurality of reference cardiac data elements 112, and identifying at least a matching reference EHR 108 as a function of the at least a distance metric 154. Accordingly, processor 102 may be configured to output at least an observation outcome 152a-n as a function of at least a matching reference EHR 108. For the purposes of this disclosure, a "distance metric" is a type of metric used in machine learning to calculate similarity between data. Common types of distance metrics may include Euclidean Distance, Manhattan Distance, Minkowski Distance, and Hamming Distance. As a nonlimiting example, a small distance metric 154 between query ECG 150 (and one or more query features therein) and a reference ECG 114 (and one or more reference features 118 therein) associated with a healthy patient may indicate that the heart of subject is in good health and has no medical concerns at the moment, whereas a large distance metric 154 between query ECG 150 and a reference ECG 114 may indicate that at least a heart function pertaining to subject may be abnormal and should be examined further. In some cases, calculating at least a distance metric 154 may include selecting one or more cutoffs, such as without limitation an absolute numerical value or a percentage, that may be used to categorize the at least a distance metric 154 into one or more categories. As a nonlimiting example, a query feature within query ECG 150 may be classified as an outlier if its associated distance metric 154 exceeds two standard deviations compared to the statistical average of reference features 118. A person of ordinary skill in the art, upon reviewing the entirety of this disclosure, will be able to identify suitable means to implement distance metric 154 for system 100.

With continued reference to FIG. 1, in some cases, outputting at least an observation outcome 152a-n may include selecting at least a diagnostic label 142 by matching query 144 against plurality of diagnostic labels 142 and outputting the at least an observation outcome 152a-n as a function of at least a matched diagnostic label 142, consistent with details described above.

With continued reference to FIG. 1, in one or more embodiments, a large group of patients with at least a similar reference feature 118 and/or reference factor 120 may be combined into a cohort, wherein one or more statistical parameters within the cohort may be combined and tallied to form a statistical model. For the purposes of this disclosure, a "statistical parameter" is a characteristic or metric that describes how one data element or group of data elements compares to another data element or group of data elements. As nonlimiting examples, data elements described herein may include one or more reference features 118, one or more reference factors, and/or one or more elements transformed therefrom or similar thereto. In some cases, a match between a first set of statistical parameters associated with a first patient and a second set of statistical parameters associated with a second patient may be determined as a function of one or more pre-determined criteria selected by one or more medical professionals. As a nonlimiting example, first set of statistical parameters and second set of statistical parameters may be considered a match when the two sets of statistical parameters are within one standard deviation from each other. As a nonlimiting example, matching first set of statistical parameters with second set of statistical parameters may involve a fuzzy set comparison, as described below.

With continued reference to FIG. 1, statistical model may be described by one or more numerical indicators such as without limitation an average or mean, a median, a standard deviation, a variance, a range, or the like. In one or more embodiments, statistical model may be updated when its associated cohort or cohorts are filtered into one or more sub-cohorts as a function of one or more newly applied inclusion/exclusion criteria. As a nonlimiting example, one or more statistical parameters associated with an ECG and/or an EHR pertaining to subject may be compared to and/or located within statistical model to help a medical professional decide whether one or more query features or query factors should be marked as abnormal. For the purposes of this disclosure, an "abnormal" feature or factor is a feature of ECG or a factor of EHR possessed by or associated with a minority of population and/or described by a numerical value that is different from a statistical average of the population, according to one or more cutoffs and/or pre-determined criteria. As a nonlimiting example, an abnormal feature may be specified as a feature possessed by or associated with less than 50% of the population and/or described by a numerical value that is at least two standard deviations away from statistical average.

With continued reference to FIG. 1, in one or more embodiments, outputting at least an observation outcome 152a-n may include determining at least a likelihood metric 156 using at least an observation machine learning model 128a-n, assigning the at least a likelihood metric 156 to at least an observation outcome 152a-n, and ranking the at least an observation outcome 152a-n as a function of the at least a likelihood metric 156. For the purposes of this disclosure, a "likelihood metric" is a metric that indicates the likelihood of a determination or prediction being correct. As nonlimiting examples, an identified or predicted medical condition that is the most likely to be correct may be listed at the top of a rank 158, whereas an identified or predicted medical condition that is the least likely to be correct may be listed at the bottom of the rank 158. As another nonlimiting example, rank 158 may be updated by applying one or more inclusion/exclusion criteria to rule out one or more entries that have already been ruled out manually. As another nonlimiting example, rank 158 may be shuffled by submitting one or more inputs or commands that reflect certain priorities or preferences of subject. In some cases, outputting at least an observation outcome 152a-n may include displaying, using a display device 160, the at least an observation outcome 152a-n as a function of rank 158.

With continued reference to FIG. 1, in one or more embodiments, likelihood metric 156 may include a softmax score ranging from 0 to 1. For the purposes of this disclosure, a "softmax score" is a number representing a probability of an output occurring. As a nonlimiting example, observation machine learning model 128a-n may generate multiple outputs, wherein a softmax score may indicate the probability regarding the occurrence of each output. In such instance, softmax score may refer to a probability observation outcome 152a-n, as described above. In one or more embodiments, observation machine learning model 128a-n may output the probability that subject will be diagnosed with a medical disease and a probability in which the subject will not be diagnosed with the medical disease. The probabilities may contain values that sum up to 1. As a nonlimiting example, softmax score may indicate the probability that the patient will be diagnosed with a medical disease from 0 to 1; a softmax score close to zero may indicate a lower confidence, whereas a softmax score close to 1 may indicate a higher confidence. As another nonlimiting example, observation machine learning model 128a-n may output that the probability that subject being diagnosed with a medical condition is 0.8, whereas the probability that subject will not be diagnosed with such medical condition is 0.2. In some cases, the probabilities may be calculated using a softmax function. In some cases, outputs of observation machine learning model 128a-n may include raw scores, sometimes referred to as 'logits', wherein softmax function may receive the raw scores and generate softmax scores ranging from 0 to 1. In one or more embodiments, observation machine learning model 128a-n may output numerical representations wherein softmax function may be used to convert numerical representations into probabilities.

With continued reference to FIG. 1, in one or more embodiments, system 100 may include a display device 160 communicatively connected to processor 102, wherein the display device 160 is configured to display at least an observation outcome 152a-n, as described above. For the purposes of this disclosure, a "display device" is a device configured to show visual information. In some cases, display device 160 may include a liquid crystal display (LCD), a cathode ray tube (CRT), a plasma display, a light emitting diode (LED) display, and any combinations thereof. Display device 160 may include, but is not limited to, a smartphone, tablet, laptop, monitor, tablet, and the like. Display device 160 may include a separate device that includes a transparent screen configured to display computer-generated images and/or information. In one or more embodiments, display device 160 may be configured to visually present data through a user interface or a graphical user interface (GUI) to at least a user, wherein the user may interact with the data through the user interface or GUI, as described below. In one or more embodiments, a user may view GUI through display device 160. In one or more embodiments, display device 160 may be located on a remote device, as described below. Additional details will be provided below in this disclosure through nonlimiting examples.

With continued reference to FIG. 1, display device 160 may include a remote device. For the purposes of this disclosure, a "remote device" is a computer device separate and distinct from system 100. For example, and without limitation, remote device may include a smartphone, a tablet, a laptop, a desktop computer, or the like. In one or more embodiments, remote device may be communicatively connected to system 100 such as, for example, through network communication, through Bluetooth communication, and/or the like. In one or more embodiments, processor 102 may receive query 144 and/or initiate one or more of subsequent steps through remote device. In one or more embodiments, one or more inputs from one or more users may be submitted through a user interface, such as a GUI, using remote device, as described below.

With continued reference to FIG. 1, for the purposes of this disclosure, a "user interface" is a means by which a user and a computer system interact, for example, using input devices and software. User interface may include a graphical user interface (GUI), command line interface (CLI), menu-driven user interface, touch user interface, voice user interface (VUI), form-based user interface, any combination thereof, or the like. In one or more embodiments, a user may interact with user interface using computing device distinct from and communicatively connected to processor 102 (i.e., a remote device), such as a smartphone, tablet, or the like operated by the user. User interface may include one or more graphical locator and/or cursor facilities allowing user to interact with graphical models and/or combinations thereof, for instance using a touchscreen, touchpad, mouse, keyboard, and/or other manual data entry device. For the purposes of this disclosure, a "graphical user interface (GUI)" is a type of user interface that allows end users to interact with electronic devices through visual representations. In one or more embodiments, GUI may include icons, menus, other visual indicators or representations (graphics), audio indicators such as primary notation, display information, and related user controls. Menu may contain a list of choices and may allow users to select one from them. A menu bar may be displayed horizontally across the screen as a pull-down menu. Menu may include a context menu that appears only when user performs a specific action. Files, programs, web pages, and the like may be represented using a small picture within GUI. In one or more embodiments, GUI may include a graphical visualization of a user profile and/or the like. In one or more embodiments, processor 102 may be configured to modify and/or update GUI as a function of at least an input or the like by populating a user interface data structure and visually presenting data through modification of the GUI.

With continued reference to FIG. 1, in one or more embodiments, GUI may contain one or more interactive elements. For the purposes of this disclosure, an "interactive element" is an element within GUI that allows for communication with processor 102 by one or more users. For example, and without limitation, interactive elements may include a plurality of tabs wherein selection of a particular tab, such as for example, by using a fingertip, may indicate to a system to perform a particular function and display the result through GUI. In one or more embodiments, interactive element may include tabs within GUI, wherein the selection of a particular tab may result in a particular function. In one or more embodiments, interactive elements may include words, phrases, illustrations, and the like to indicate a particular process that one or more users would like system to perform. A person of ordinary skill in the art, upon reviewing the entirety of this disclosure, will be aware of various ways in which user interfaces, GUIs, and/or elements thereof may be implemented and/or used as described in this disclosure.

With continued reference to FIG. 1, in one or more embodiments, display device 160 and/or remote device may be configured to display at least an event handler graphic corresponding to at least an event handler. For the purposes of this disclosure, an "event handler graphic" is a graphical element with which user may interact using display device 160 and/or remote device to enter data. Data may be entered, for instance and without limitation, for query 144 or the like as described above. Event handler graphic may include, without limitation, a button, a link, a checkbox, a text entry box and/or window, a drop-down list, a slider, or any other event handler graphic deemed suitable by a person of ordinary skill in the art upon reviewing the entirety of this disclosure. For the purposes of this disclosure, an "event handler" is a module, data structure, function, and/or routine that performs an action on display device 160 and/or remote device in response to one or more user inputs. For instance, and without limitation, event handler may record data corresponding to user selections of previously populated fields such as drop-down lists and/or text auto-complete and/or default entries, data corresponding to user selections of checkboxes, radio buttons, or the like, potentially along with automatically entered data triggered by such selections, user entry of textual data using a keyboard, touchscreen, speech-to-text program, or the like. Event handler may generate prompts for further information, may compare data to validation rules such as requirements that the data in question be entered within certain numerical ranges, and/or may modify data and/or generate warnings to user in response to such requirements. Event handler may convert data into expected and/or desired formats, for instance such as date formats, currency entry formats, name formats, or the like. Event handler may transmit data from a remote device to computing device.

With continued reference to FIG. 1, in one or more embodiments, event handler may include a cross-session state variable. For the purposes of this disclosure, a "cross-session state variable" is a variable recording data entered on remote device during a previous session. Such data may include, for instance, previously entered text, previous selections of one or more elements as described above, or the like. For instance, cross-session state variable data may represent a search that user entered in a past session. Cross-session state variable may be saved using any suitable combination of client-side data storage on remote device and server-side data storage on computing device; for instance, data may be saved wholly or in part as a "cookie" which may include data or an identification of remote device to prompt provision of cross-session state variable by the computing device, which may store the data on the computing device. Alternatively, or additionally, computing device may use login credentials, device identifier, and/or device fingerprint data to retrieve cross-session state variable, which the computing device may transmit to remote device. Cross-session state variable may include at least a prior session datum. A prior session datum may include any element of data that may be stored in cross-session state variable. Event handler graphic may be further configured to display at least a prior session datum, for instance and without limitation, by auto-populating user query data from previous sessions.

With continued reference to FIG. 1, in one or more embodiments, processor 102 and/or computing device may configure display device 160 and/or remote device to generate a graphical view. For the purposes of this disclosure, a "graphical view" is a data structure that results in display of one or more graphical elements on a screen. Graphical view may include at least a display element. For the purposes of this disclosure, a "display element" is an image that a program and/or data structure may cause to be displayed. Display elements may include, without limitation, windows, pop-up boxes, web browser pages, display layers, and/or any other display element deemed relevant by a person of ordinary skill in the art upon reviewing the entirety of this disclosure. Graphical view may include at least a selectable event graphic corresponding to one or more selectable event handlers. For the purposes of this disclosure, a "selectable event graphic" is a graphical element that, upon selection, will trigger an action to be performed. Selection may be performed using a cursor or other locator as manipulated using a locator device such as a mouse, touchscreen, track pad, joystick, or the like. As a nonlimiting example, a selectable event graphic may include a redirection link, defined as a hyperlink, button, image, portion of an image, and/or other graphic containing or referring to a uniform resource locator (URL) and/or other resource locator to another graphical view including without limitation buttons, and/or to a process that performs navigation to such URL and/or other resource locator upon selection of selectable event graphic. Redirection may be performed using any event handler, including without limitation event handlers detecting the click of a mouse or other locator, access of redirection link using a touchscreen, the selection of any key, mouseover events, or the like.

With continued reference to FIG. 1, in one or more embodiments, processor 102 may be further configured to train an ensemble machine learning model 162 as a function of at least an observation machine learning model 128*a-n*, as described above. Specifically, training ensemble machine learning model 162 may include receiving the at least an observation outcome 152*a-n* from each of at least an observation machine learning model 128*a-n* and training the ensemble machine learning model as a function of the at least an observation outcome 152*a-n*. Ensemble machine learning model 162 may be configured to receive at least an observation outcome 152*a*-*n* from the at least an observation machine learning model 128*a*-*n* as an input and output a weighted observation outcome 152*a*-*n*. Accordingly, processor may be configured to generating weighted observation outcome 152*a*-*n* using the ensemble machine learning model 162. Additional details regarding exemplary embodiments of ensemble machine learning model 162 will be provided below in this disclosure.

Figure 2A:
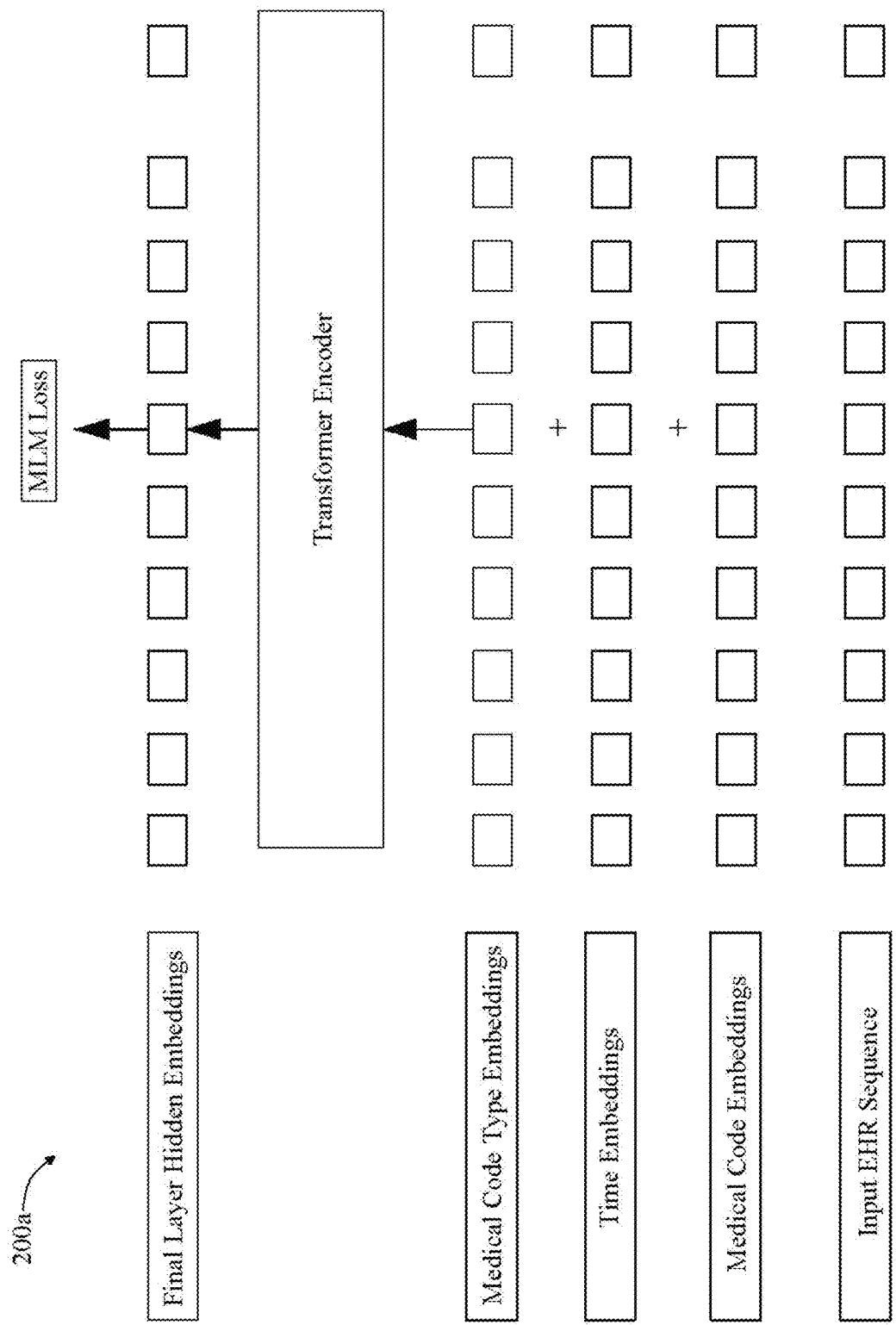
FIG. 2A is an exemplary embodiment of a transformer architecture.

Referring now to FIG. 2A, an exemplary embodiment 200*a* of a transformer architecture is illustrated. Transformer architecture may include a Bidirectional Encoder Representations from Transformers (BERT). As a nonlimiting example, a vocabulary of size 28593 may be constructed from International Classification of Diseases (ICD, such as ICE-9 and ICD-10) diagnoses codes, ICD procedure codes, and medication prescriptions. The input to transformer architecture includes a sequence of medical codes. Each code may be processed by adding its corresponding medical code embedding, time embedding, and medical code type embedding. Time embeddings are constructed in a weekly manner based on medical code's timestamp, which means that all codes generated in the same week have the same time embedding. Model weights may be initialized randomly, and BERT pre-training strategy (i.e., Masked Language Modeling (MLM)) may be followed to learn the representations of an EHR sequence.

Figure 2B:
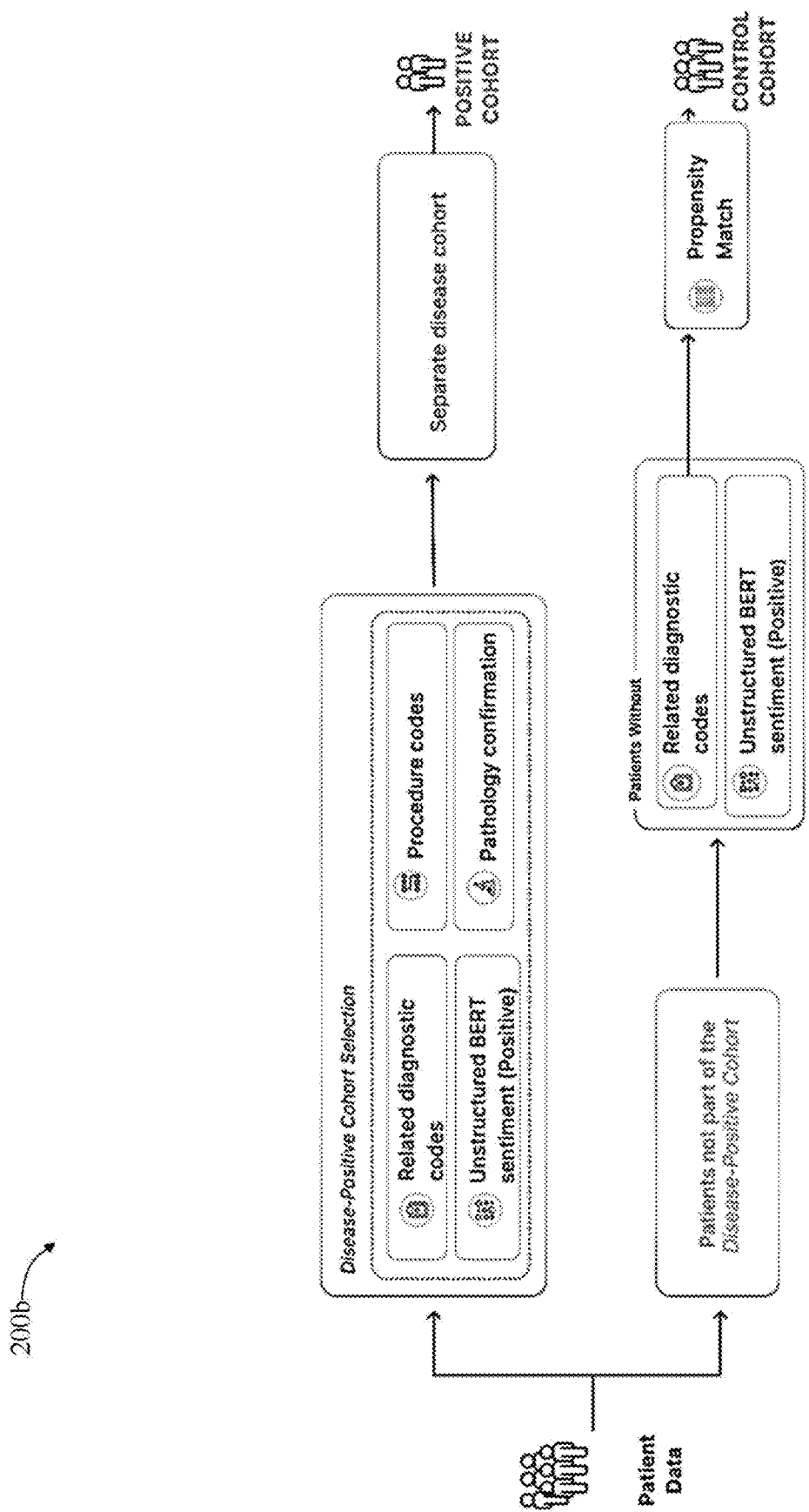
FIG. 2B is an exemplary embodiment of a workflow for identification of disease cohorts.

Referring now to FIG. 2B, an exemplary embodiment of a workflow 200*b* for identification of two disease cohorts is described. ICD-9, ICD-10, Systematized Nomenclature of Medicine, and Hospital Adaptation of the International Classification of Diseases codes may be used to identify such disease cohorts, and the same codes may be used to exclude any cases from the control cohort. "Disease cohort" and "case cohort" may be used interchangeably throughout this disclosure. In one or more embodiments, medical history timeframe 124 may specify that only procedures that are performed within a year of the earliest and latest diagnosis dates may be considered. In one or more embodiments, patient notes may be processed using machine learning models to check whether patients were diagnosed with a certain disease or associated with a certain medical condition. This may include a three-step process which includes identifying synonyms for a disease, getting relevant sentences from the patient notes that mentioned the disease of interest or the synonyms related thereto, and using a machine learning model to check whether these sentences indicate that the patient had the disease of interest. Various databases, such as MESH terms, DOID, MONDO Ontology, and Wikidata, may be used to identify known synonyms of BE and EAC in the literature. In addition to these tools, manual reading of clinical notes and domain knowledge may be used to come up with terms that identify a certain disease or medical condition. In one or more embodiments, workflow 200*b* may include an identification of sentences from patient notes that mention a certain disease or its synonyms. In one or more embodiments, a natural language model such as LLM, classification model, or BERT may be trained to determine whether a sentence indicates that a patient had a particular disease. Sentences identified from the patient notes may then be processed through a machine learning model to check whether the patient was diagnosed with such disease.

With continued reference to FIG. 2B, the process of identifying disease-positive patients may require that these patients have, in their pathology notes and/or EHR, certain terms related to a particular disease. For example, a combination of two or words in a well-defined order, such as "pulmonary" immediately preceding "hypertension", may be necessary to confirm a diagnosis of EAC. This may be performed to preserve the fidelity of information.

With continued reference to FIG. 2B, workflow 200*b* may include identification of a control cohort and propensity matching to cases. As a nonlimiting example, control cohort may be created by randomly sampling patients who did not meet any of the criteria that set forth for identification of disease cohort from Clinical Data Analytics Platform (CDAP), a data store containing EHRs associated with 6 million patients. Hence, patients in the control cohort may not have either any structured or any unstructured evidence for the medical condition of interest. These sampled patients may then be propensity-matched to cases on (i) the year of diagnosis (of the case cohort), (ii) the number of structured disease diagnoses during the observation time 126 (as described above), and/or (iii) the proportion of hospitalization in the observation time 126 to the disease cohort (because hospitalization leads to a larger number of medical records per encounter). In one or more embodiments, the cohorts may not be matched to known risk factors of a particular disease in question to enable an identification of risk factors agnostic to current knowledge.

With continued reference to FIG. 2B, in both the case and control cohorts, patients younger than 18 years and those older than 85 years may be excluded. In addition, only patients who meet the data completeness criteria (defined as having two or more encounters within observation time 126) may be retained. This may be done to ensure that the model has the opportunity to learn from a minimum number of encounters, which optimizes model performance.

With continued reference to FIG. 2B, the case identification algorithm described above may be tested against two population-based, manually identified, and annotated cohorts of patients with two different yet related medical conditions, such as COPD and PH, as described above. Cohort may be created using resources from the Rochester Epidemiology Project, which is a population-based medical record linkage system, recently expanded to 11 counties in SE Minnesota.

With continued reference to FIG. 2B, in one or more embodiments, a machine m=learning model, such as observation machine learning model 128*a*-*n*, may be trained using nontemporal features, i.e., features that do not change with time. In one or more embodiments, nontemporal features may include but are not limited to, age at lead time, sex, race/ethnicity, family history pertaining to a particular condition, smoking status defined as current, past, or never, and the like. In one or more embodiments, observation machine learning model 128*a*-*n* may be trained using temporal features 122, i.e., features associated with time, as described above. In one or more embodiments, temporal features 122 may include but are not limited to medications, comorbidities (based on structured analysis), and the like. In one or more embodiments, temporal features 122 may include laboratory tests. Laboratory tests may include tests such as but not limited to hemoglobin, aspartate aminotransferase, alanine aminotransferase, alkaline phosphatase, total bilirubin, albumin, creatinine, sodium, potassium, total cholesterol, low-density lipoprotein cholesterol, high-density lipoprotein cholesterol, triglycerides, chloride, calcium, glucose, blood urea nitrogen, lipase, amylase, gamma glutamyl transferase, prostate-specific antigen, and hemoglobin A1c. These tests may be chosen based on the frequency of occurrence and clinical expertise. In one or more embodiments, temporal features 122 may include symptoms. In one or more embodiments, symptoms may include symptoms identified by augmented curation on patient notes such as but not limited to abdominal pain, dysphagia, dyspepsia, vomiting, diarrhea, heartburn, water brash, chest pain, odynophagia, nausea, snoring, esophageal reflux, dyspnea, arthritis, backache, weight loss, cough, hoarseness, and/or hematemesis. In one or more embodiments, temporal features 122 may further include body mass index (BMI) of a patient over time.

Figure 2C:
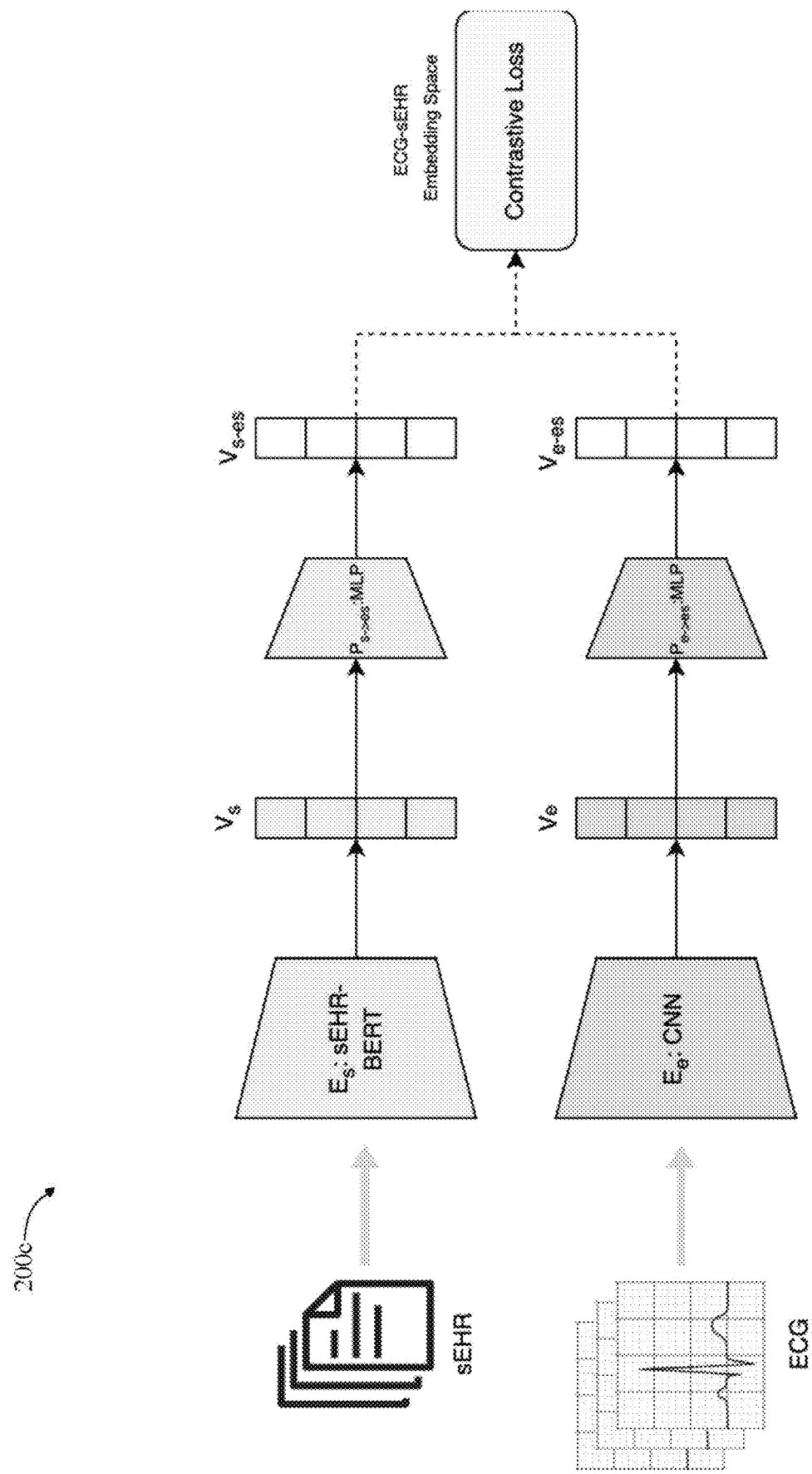
FIG. 2C is an exemplary embodiment of a contrastive machine learning model.

Referring now to FIG. 2C, an exemplary embodiment 200c of a contrastive machine learning model 138 is illustrated. To create ECG-structured EHR (ECG-sEHR) pairs, ($X_e$, $X_s$), processor 102 may select an ECG of a given patient, $X_e$, and consider all ICD diagnoses codes, ICD procedure codes, and medication prescriptions associated with that patient within a period of one year prior, and one year subsequent, to the acquisition timestamp of that ECG. The medical codes restricted to this time range are arranged sequentially to form an initial structured EHR input sequence to a structured EHR-BERT model. Processor may use a maximum sequence length of 200 medical codes as input to a structured EHR-BERT encoder. Initial structured EHR input sequence may be filled with zeros if the structured EHR sequence length may be less than 200. On the other hand, structured EHR input sequence may be trimmed by considering the nearest 200 medical codes to ECG acquisition timestamp if the structured EHR sequence length is greater than 200, to get the final $X_s$.

With continued reference to FIG. 2C, in ECG-structured EHR model, processor 102 may pair ECGs with structured EHRs and apply multimodal contrastive learning in joint ECG-structured EHR embedding space, $\Omega_{es}$. For the purposes of this disclosure, $X_s^i$ is the structured EHR sequence of the i-th sample; $X_e^i$ is the ECG waveform of the i-th sample; $E_e$ and $E_s$ are modality-specific encoders for ECG and sEHR, respectively; $v_e$ or $v_s$ is a representation obtained by passing $x_e^i$ or $x_s^i$ into its respective, modality-specific encoder, $E_e$ or $E_s$; and $P_{m \to s}$ is the projection network mapping from representation of modality e or s to representation in their shared space, es. Accordingly $$v_e^i = E_e(x_e^i)$$
$$v_s^i = E_s(x_s^i)$$
$$v_{e-es}^i = P_{e \to es}(v_e^i)$$
$$v_{s-es}^i = P_{s \to es}(v_s^i)$$

Let $L_{es}^{\square}$ be the contrastive loss between ECG and structured EHR, $L_i^{e \to s}$ be the contrastive loss directed from ECG to structured EHR, and $L_i^{s \to e}$ be the contrastive loss directed from structured EHR to ECG. Then, the loss for the ECG-structured EHR model is given by:

$$L_{es}^{\square} = \frac{1}{n}\sum_{i=1}^{N}(\lambda_{es}L_i^{e \to s} + (1 - \lambda_{es})L_i^{s \to e})$$

Contrastive loss between ECG and structured EHR is applied in ECG-sEHR joint embedding space where:

$$L_i^{e \to s} = -\log\frac{\exp(s(v_{e-es}^i, v_{s-es}^i)/T)}{\sum_{K=1}^{N}\exp(s(v_{e-es}^i, v_{s-es}^k)/T)}$$

$$L_i^{s \to e} = -\log\frac{\exp(s(v_{s-es}^i, v_{e-es}^i)/T)}{\sum_{K=1}^{N}\exp(s(v_{s-es}^i, v_{e-es}^k)/T)}$$

Details described herein may be consistent with any details disclosed in U.S. patent application Ser. No. 18/230,043, filed on Dec. 21, 2023, entitled "APPARATUS AND A METHOD FOR GENERATING A DIAGNOSTIC LABEL", the entirety of which is incorporated herein by reference.

Figure 2D:
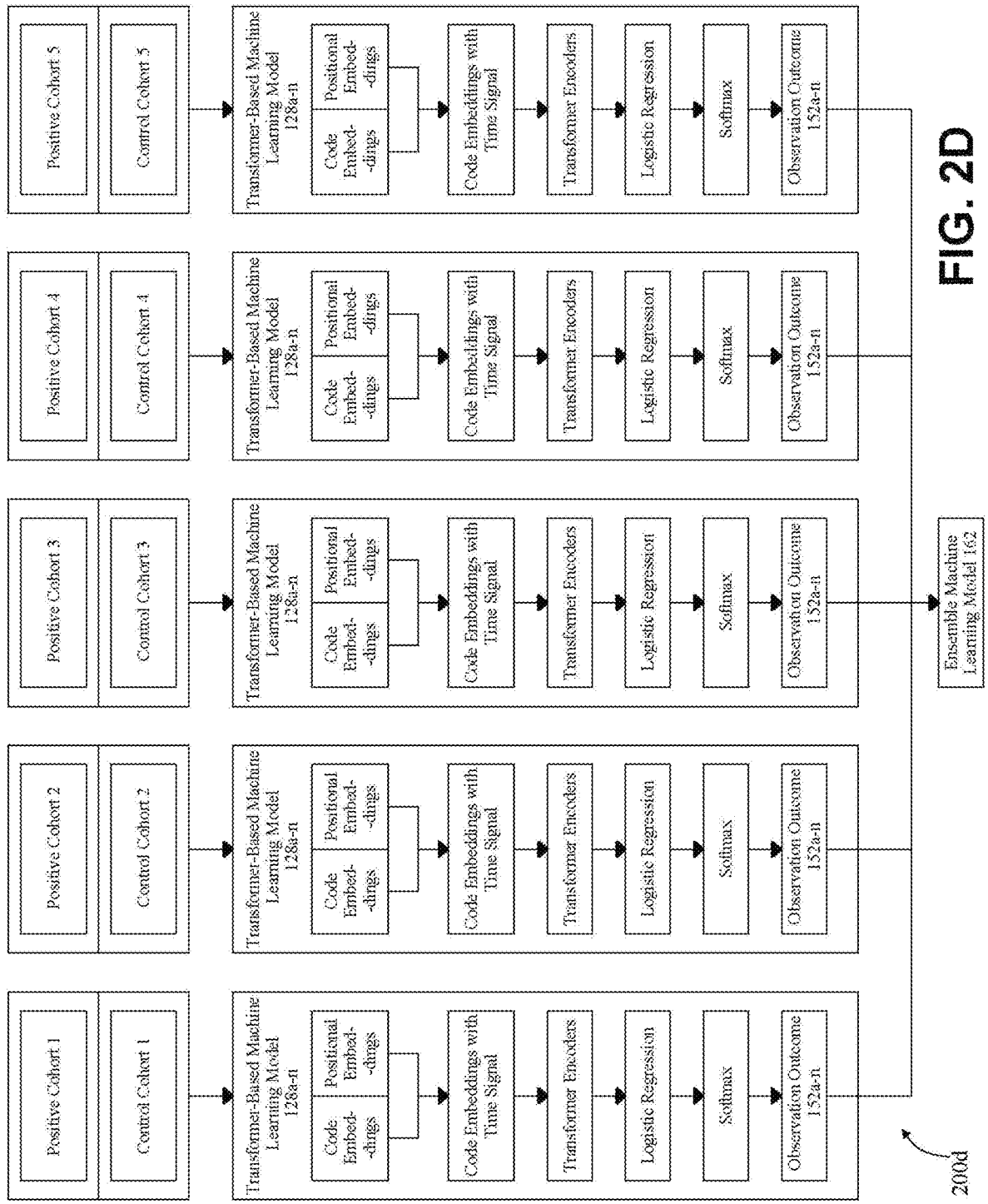
FIG. 2D is an exemplary embodiment of workflow for an ensemble machine learning model.

Referring now to FIG. 2D, an exemplary embodiment 200d of a workflow for an ensemble machine learning model 162 is illustrated. In one or more embodiments, patient timeline may include observation time 126 as described above. In one or more embodiments, five randomly selected control cohorts may be created, enabling training of five transformer-based machine learning models 130. Each of the transformer-based machine learning models 130 may use the same disease cohort but trained with a different control cohort. As a nonlimiting example, for a first medical condition, the case-to-control ratio may be 1:5, and for second medical condition, the case-to-control ratio may be 1:10. The output of these five transformer-based machine learning models 130 may be used to train an ensemble machine learning model 162 using logistic regression. For the purposes of this disclosure, "logistic regression" is a supervised machine learning algorithm used for binary classification tasks. In one or more embodiments, five independent control cohorts may be created. Five control patients may be matched to each patient with first medical condition, and ten control patients matched to each patient with second medical condition. Five transformer-based machine learning models 130 may be developed by pairing a first medical condition cohort and a second medical condition cohort with five independent control cohorts. These five transformer-based machine learning models 130 may then be integrated into a single ensemble machine learning model 162, as described above using logistic regression.

Figure 2E:
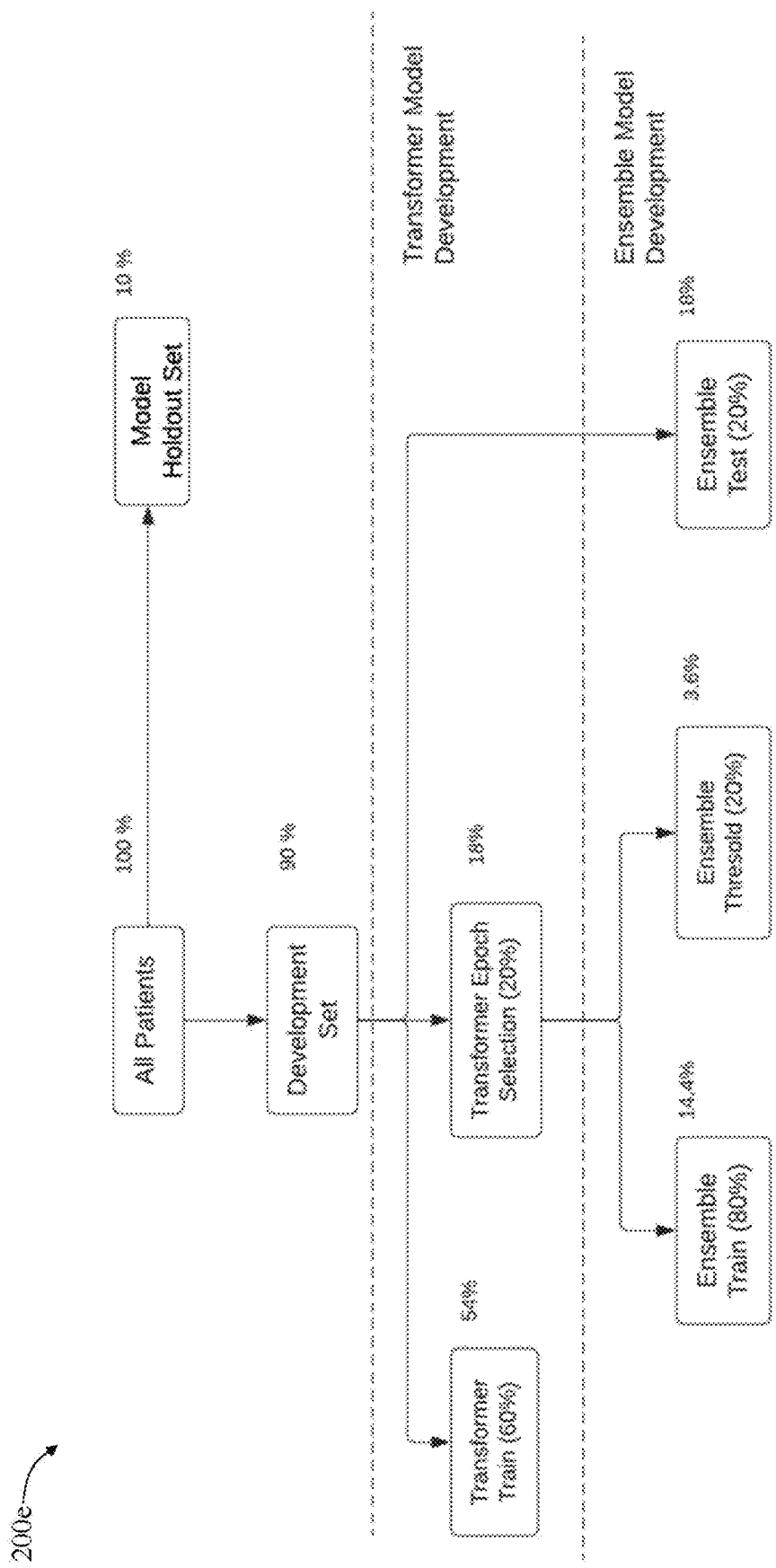
FIG. 2E is an exemplary embodiment of a partition of data used for training a machine learning model.

Referring now to FIG. 2E, an exemplary embodiment 200e of a partition of data used for training a machine learning model is illustrated. At the outset, 10% of the data may be kept aside as a holdout test data set: the Model Holdout Set (MHS). The rest of the data may be used in training the transformer and ensemble models, i.e., the Development Set (DS). The DS may be split into 3 sets in a ratio of 60:20:20. 60% of the DS may be used to train transformer-based machine learning model 130, i.e., the Transformer Training Set. 20% of the DS may be used to choose the best epoch for transformer-based machine learning model 130, i.e., the Transformer Epoch Set (TES). The last 20% may be used to train ensemble machine learning model 162, i.e., the Ensemble Test Set. In some cases, the TES may also be used to train ensemble machine learning model 162. Accordingly, the TES may be further split in a ratio of 80:20. 80% of the TES may be used for training ensemble machine learning model 162, i.e., the Ensemble Training Set, and 20% may be used to calibrate the ensemble machine learning model 162, i.e., the Ensemble Development Set. The output of ensemble machine learning model 162 may include a softmax score ranging from 0 to 1, as described above. The threshold for dichotomization for the ensemble result may be chosen based on the Youden J method to maximize the area under the receiver-operating curve (AUROC) of the model. A score above the threshold may indicate that the patient is at a substantial risk of being diagnosed with one or more medical conditions in the next year and screening should be considered.

Figure 3:
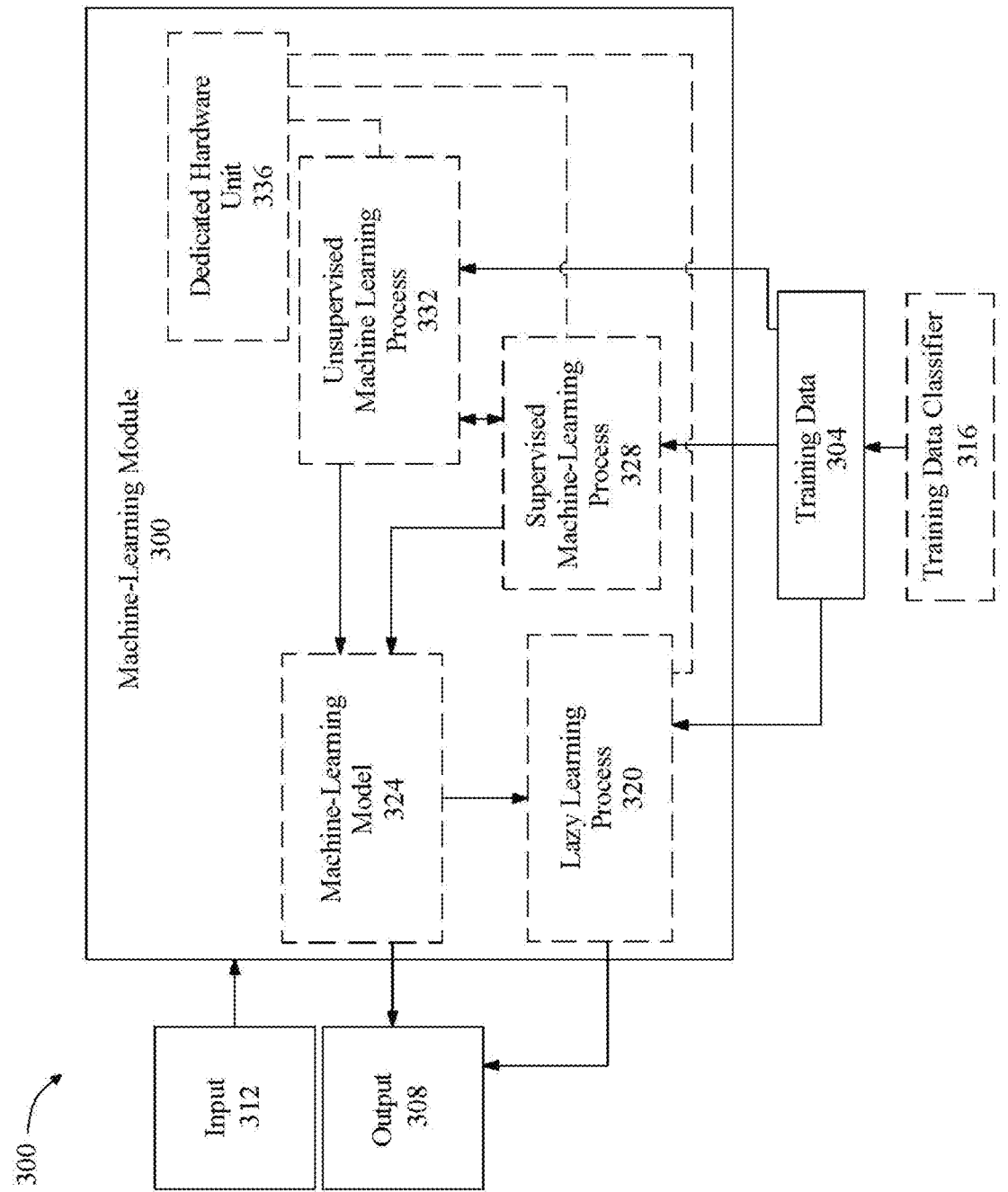
FIG. 3 is a block diagram of an exemplary embodiment of a machine learning process.

Referring now to FIG. 3, an exemplary embodiment of a machine learning module 300 that may perform one or more machine learning processes as described above is illustrated. Machine learning module may perform determinations, classification, and/or analysis steps, methods, processes, or the like as described in this disclosure using machine learning processes. For the purposes of this disclosure, a "machine learning process" is an automated process that uses training data 304 to generate an algorithm instantiated in hardware or software logic, data structures, and/or functions that will be performed by a computing device/module to produce outputs 308 given data provided as inputs 312; this is in contrast to a non-machine learning software program where the commands to be executed are pre-determined by user and written in a programming language.

With continued reference to FIG. 3, "training data", for the purposes of this disclosure, are data containing correlations that a machine learning process may use to model relationships between two or more categories of data elements. For instance, and without limitation, training data 304 may include a plurality of data entries, also known as "training examples", each entry representing a set of data elements that were recorded, received, and/or generated together. Data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine learning processes as described in further detail below. Training data 304 may be formatted and/or organized by categories of data elements, for instance by associating data elements with one or more descriptors corresponding to categories of data elements. As a nonlimiting example, training data 304 may include data entered in standardized forms by persons or processes, such that entry of a given data element within a given field in a given form may be mapped to one or more descriptors of categories. Elements in training data 304 may be linked to descriptors of categories by tags, tokens, or other data elements. For instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

With continued reference to FIG. 3, alternatively or additionally, training data 304 may include one or more elements that are uncategorized; that is, training data 304 may not be formatted or contain descriptors for some elements of data. Machine learning algorithms and/or other processes may sort training data 304 according to one or more categorizations using, for instance, natural language processing algorithms, tokenization, detection of correlated values in raw data, and the like; categories may be generated using correlation and/or other processing algorithms. As a nonlimiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine learning algorithms, and/or automated association of data in the data entry with descriptors or into a given format. The ability to categorize data entries automatedly may enable the same training data 304 to be made applicable for two or more distinct machine learning algorithms as described in further detail below. Training data 304 used by machine learning module 300 may correlate any input data as described in this disclosure to any output data as described in this disclosure. As a nonlimiting illustrative example, inputs may include plurality of reference ECGs 114 or reference EHRs 108, whereas outputs may include plurality of reference features 118 or reference factors 120, respectively.

With continued reference to FIG. 3, training data 304 may be filtered, sorted, and/or selected using one or more supervised and/or unsupervised machine learning processes and/or models as described in further detail below; such processes and/or models may include without limitation a training data classifier 316. For the purposes of this disclosure, a "classifier" is a machine learning model, that sorts inputs into categories or bins of data, outputting the categories or bins of data and/or labels associated therewith. A classifier may include a data structure representing and/or using a mathematical model, neural net, or a program generated by a machine learning algorithm, known as a "classification algorithm". A classifier may be configured to output at least a datum that labels or otherwise identifies a set of data that are clustered together, found to be close under a distance metric as described below, or the like. A distance metric may include any norm, such as, without limitation, a Pythagorean norm. Machine learning module 300 may generate a classifier using a classification algorithm. For the purposes of this disclosure, a "classification algorithm" is a process wherein a computing device and/or any module and/or component operating therein derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, Fisher's linear discriminant, quadratic classifiers, decision trees, boosted trees, random forest classifiers, learning vector quantization, and/or neural network-based classifiers. In one or more embodiments, training data classifier 316 may classify elements of training data to a plurality of cohorts as a function of certain anatomic and/or demographic traits.

With continued reference to FIG. 3, machine learning module 300 may be configured to generate a classifier using a naive Bayes classification algorithm. Naive Bayes classification algorithm generates classifiers by assigning class labels to problem instances, represented as vectors of element values. Class labels are drawn from a finite set. Naive Bayes classification algorithm may include generating a family of algorithms that assume that the value of a particular element is independent of the value of any other element, given a class variable. Naive Bayes classification algorithm may be based on Bayes Theorem expressed as P(A/B)=P(B/A)×P(A)+P(B), where P(A/B) is the probability of hypothesis A given data B, also known as posterior probability; P(B/A) is the probability of data B given that the hypothesis A was true; P(A) is the probability of hypothesis A being true regardless of data, also known as prior probability of A; and P(B) is the probability of the data regardless of the hypothesis. A naive Bayes algorithm may be generated by first transforming training data into a frequency table. Machine learning module 300 may then calculate a likelihood table by calculating probabilities of different data entries and classification labels. Machine learning module 300 may utilize a naive Bayes equation to calculate a posterior probability for each class. A class containing the highest posterior probability is the outcome of prediction. Naive Bayes classification algorithm may include a gaussian model that follows a normal distribution. Naive Bayes classification algorithm may include a multinomial model that is used for discrete counts. Naive Bayes classification algorithm may include a Bernoulli model that may be utilized when vectors are binary.

With continued reference to FIG. 3, machine learning module 300 may be configured to generate a classifier using a k-nearest neighbors (KNN) algorithm. For the purposes of this disclosure, a "k-nearest neighbors algorithm" is or at least includes a classification method that utilizes feature similarity to analyze how closely out-of-sample features resemble training data 304 and to classify input data to one or more clusters and/or categories of features as represented in training data 304. This may be performed by representing both training data 304 and input data in vector forms and using one or more measures of vector similarity to identify classifications within training data 304 and determine a classification of input data. K-nearest neighbors algorithm may include specifying a k-value, or a number directing the classifier to select the k most similar entries of training data 304 to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a nonlimiting example, an initial heuristic may include a ranking of associations between inputs 312 and elements of training data 304. Heuristic may include selecting some number of highest-ranking associations and/or training data elements.

With continued reference to FIG. 3, generating k-nearest neighbors algorithm may generate a first vector output containing a data entry cluster, generating a second vector output containing input data, and calculate the distance between the first vector output and the second vector output using any suitable norm such as cosine similarity, Euclidean distance measurement, or the like. Each vector output may be represented, without limitation, as an n-tuple of values, where n is at least 2. Each value of n-tuple of values may represent a measurement or other quantitative value associated with a given category of data or attribute, examples of which are provided in further detail below. A vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent when their directions and/or relative quantities of values are the same; thus, as a nonlimiting example, a vector represented as [5, 10, 15] may be treated as equivalent, for the purposes of this disclosure, as a vector represented as [1, 2, 3]. Vectors may be more similar where their directions are more similar, and more different where their directions are more divergent. However, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized", or divided by a "length" attribute, such as a length attribute 1 as derived using a Pythagorean norm:

$$l = \sqrt{\Sigma_{i=0}^{n} a_i^2},$$

where $a_i$ is attribute number of vector i. Scaling and/or normalization may function to make vector comparison independent of absolute quantities of attributes, while preserving any dependency on similarity of attributes. This may, for instance, be advantageous where cases represented in training data 304 are represented by different quantities of samples, which may result in proportionally equivalent vectors with divergent values.

With continued reference to FIG. 3, training examples for use as training data may be selected from a population of potential examples according to cohorts relevant to an analytical problem to be solved, a classification task, or the like. Alternatively or additionally, training data 304 may be selected to span a set of likely circumstances or inputs for a machine learning model and/or process to encounter when deployed. For instance, and without limitation, for each category of input data to a machine learning model and/or process that may exist in a range of values in a population of phenomena such as images, user data, process data, physical data, or the like, a computing device, processor 102, and/or machine learning module 300 may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to user, so that a process can detect, automatically or via user input, one or more values that are not included in the set of training examples. Computing device, processor 102, and/or machine learning module 300 may automatically generate a missing training example. This may be done by receiving and/or retrieving a missing input and/or output value and correlating the missing input and/or output value with a corresponding output and/or input value collocated in a data record with the retrieved value, provided by user, another device, or the like.

With continued reference to FIG. 3, computing device, processor 102, and/or machine learning module 300 may be configured to preprocess training data 304. For the purposes of this disclosure, "preprocessing" training data is a process that transforms training data from a raw form to a format that can be used for training a machine learning model. Preprocessing may include sanitizing, feature selection, feature scaling, data augmentation and the like.

With continued reference to FIG. 3, computing device, processor 102, and/or machine learning module 300 may be configured to sanitize training data. For the purposes of this disclosure, "sanitizing" training data is a process whereby training examples that interfere with convergence of a machine learning model and/or process are removed to yield a useful result. For instance, and without limitation, a training example may include an input and/or output value that is an outlier from typically encountered values, such that a machine learning algorithm using the training example will be skewed to an unlikely range of input 312 and/or output 308; a value that is more than a threshold number of standard deviations away from an average, mean, or expected value, for instance, may be eliminated. Alternatively or additionally, one or more training examples may be identified as having poor-quality data, where "poor-quality" means having a signal-to-noise ratio below a threshold value. In one or more embodiments, sanitizing training data may include steps such as removing duplicative or otherwise redundant data, interpolating missing data, correcting data errors, standardizing data, identifying outliers, and/or the like. In one or more embodiments, sanitizing training data may include algorithms that identify duplicate entries or spell-check algorithms.

With continued reference to FIG. 3, in one or more embodiments, images used to train an image classifier or other machine learning model and/or process that takes images as inputs 312 or generates images as outputs 308 may be rejected if image quality is below a threshold value. For instance, and without limitation, computing device, processor 102, and/or machine learning module 300 may perform blur detection. Elimination of one or more blurs may be performed, as a nonlimiting example, by taking Fourier transform or a Fast Fourier Transform (FFT) of image and analyzing a distribution of low and high frequencies in the resulting frequency-domain depiction of the image. Numbers of high-frequency values below a threshold level may indicate blurriness. As a further nonlimiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of image, based on the hypothesis that rapid changes indicate sharp edges in the image, and thus are indicative of a lower degree of blurriness. Blur detection may be performed using a wavelet-based operator, which uses coefficients of a discrete wavelet transform to describe the frequency and spatial content of images. Blur detection may be performed using statistics-based operators that take advantage of several image statistics as texture descriptors in order to compute a focus level. Blur detection may be performed by using discrete cosine transform (DCT) coefficients in order to compute a focus level of an image from its frequency content.

With continued reference to FIG. 3, computing device, processor 102, and/or machine learning module 300 may be configured to precondition one or more training examples. For instance, and without limitation, where a machine learning model and/or process has one or more inputs 312 and/or outputs 308 requiring, transmitting, or receiving a certain number of bits, samples, or other units of data, one or more elements of training examples to be used as or compared to inputs 312 and/or outputs 308 may be modified to have such a number of units of data. In one or more embodiments, computing device, processor 102, and/or machine learning module 300 may convert a smaller number of units, such as in a low pixel count image, into a desired number of units by upsampling and interpolating. As a nonlimiting example, a low pixel count image may have 100 pixels, whereas a desired number of pixels may be 128. Processor 102 may interpolate the low pixel count image to convert 100 pixels into 128 pixels. It should also be noted that one of ordinary skill in the art, upon reading the entirety of this disclosure, would recognize the various methods to interpolate a smaller number of data units such as samples, pixels, bits, or the like to a desired number of such units. In one or more embodiments, a set of interpolation rules may be trained by sets of highly detailed inputs 312 and/or outputs 308 and corresponding inputs 312 and/or outputs 308 downsampled to smaller numbers of units, and a neural network or another machine learning model that is trained to predict interpolated pixel values using the training data 304. As a nonlimiting example, a sample input 312 and/or output 308, such as a sample picture, with sample-expanded data units (e.g., pixels added between the original pixels) may be input to a neural network or machine learning model and output a pseudo replica sample picture with dummy values assigned to pixels between the original pixels based on a set of interpolation rules. As a nonlimiting example, in the context of an image classifier, a machine learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, computing device, processor 102, and/or machine learning module 300 may utilize sample expander methods, a low-pass filter, or both. For the purposes of this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor 102, and/or machine learning module 300 may use averaging, such as luma or chroma averaging in images, to fill in data units in between original data units.

With continued reference to FIG. 3, in one or more embodiments, computing device, processor 102, and/or machine learning module 300 may downsample elements of a training example to a desired lower number of data elements. As a nonlimiting example, a high pixel count image may contain 256 pixels, however a desired number of pixels may be 128. Processor 102 may downsample the high pixel count image to convert 256 pixels into 128 pixels. In one or more embodiments, processor 102 may be configured to perform downsampling on data. Downsampling, also known as decimation, may include removing every $N^{th}$ entry in a sequence of samples, all but every $N^{th}$ entry, or the like, which is a process known as "compression" and may be performed, for instance by an N-sample compressor implemented using hardware or software. Anti-aliasing and/or anti-imaging filters, and/or low-pass filters, may be used to eliminate side effects of compression.

With continued reference to FIG. 3, feature selection may include narrowing and/or filtering training data 304 to exclude features and/or elements, or training data including such elements that are not relevant to a purpose for which a trained machine learning model and/or algorithm is being trained, and/or collection of features, elements, or training data including such elements based on relevance to or utility for an intended task or purpose for which a machine learning model and/or algorithm is being trained. Feature selection may be implemented, without limitation, using any process described in this disclosure, including without limitation using training data classifiers, exclusion of outliers, or the like.

With continued reference to FIG. 3, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, wherein a difference between each value, X, and a minimum value, $X_{min}$, in a set or subset of values is divided by a range of values, $X_{max}-X_{min}$, in the set or subset:

$$\frac{X - X_{min}}{X_{max} - X_{min}}.$$

Feature scaling may include mean normalization, wherein a difference between each value, X, and a mean value of a set and/or subset of values, $X_{mean}$, is divided by a range of values, $X_{max}-X_{min}$, in the set or subset:

$$X_{new} = \frac{X - X_{mean}}{X_{max} - X_{min}}.$$

Feature scaling may include standardization, wherein a difference between X and $X_{mean}$ is divided by a standard deviation, $\sigma$, of a set or subset of values:

$$X_{new} = \frac{X - X_{mean}}{\sigma}.$$

Feature scaling may be performed using a median value of a set or subset, $X_{median}$, and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

A Person of ordinary skill in the art, upon reviewing the entirety of this disclosure, will be aware of various alternative or additional approaches that may be used for feature scaling.

With continued reference to FIG. 3, computing device, processor 102, and/or machine learning module 300 may be configured to perform one or more processes of data augmentation. For the purposes of this disclosure, "data augmentation" is a process that adds data to a training data 304 using elements and/or entries already in the dataset. Data augmentation may be accomplished, without limitation, using interpolation, generation of modified copies of existing entries and/or examples, and/or one or more generative artificial intelligence (AI) processes, for instance using deep neural networks and/or generative adversarial networks. Generative processes may be referred to alternatively in this context as "data synthesis" and as creating "synthetic data". Augmentation may include performing one or more transformations on data, such as geometric, color space, affine, brightness, cropping, and/or contrast transformations of images.

With continued reference to FIG. 3, machine learning module 300 may be configured to perform a lazy learning process and/or protocol 320. For the purposes of this disclosure, a "lazy learning" process and/or protocol is a process whereby machine learning is conducted upon receipt of input 312 to be converted to output 308 by combining the input 312 and training data 304 to derive the algorithm to be used to produce the output 308 on demand. A lazy learning process may alternatively be referred to as a "lazy loading" or "call-when-needed" process and/or protocol. For instance, an initial set of simulations may be performed to cover an initial heuristic and/or "first guess" at an output 308 and/or relationship. As a nonlimiting example, an initial heuristic may include a ranking of associations between inputs 312 and elements of training data 304. Heuristic may include selecting some number of highest-ranking associations and/or training data 304 elements. Lazy learning may implement any suitable lazy learning algorithm, including without limitation a k-nearest neighbors algorithm, a lazy naive Bayes algorithm, or the like. A person of ordinary skill in the art, upon reviewing the entirety of this disclosure, will be aware of various lazy learning algorithms that may be applied to generate outputs as described in this disclosure, including without limitation lazy learning applications of machine learning algorithms as described in further detail below.

With continued reference to FIG. 3, alternatively or additionally, machine learning processes as described in this disclosure may be used to generate machine learning models 324. A "machine learning model", for the purposes of this disclosure, is a data structure representing and/or instantiating a mathematical and/or algorithmic representation of a relationship between inputs 312 and outputs 308, generated using any machine learning process including without limitation any process described above, and stored in memory. An input 312 is submitted to a machine learning model 324 once created, which generates an output 308 based on the relationship that was derived. For instance, and without limitation, a linear regression model, generated using a linear regression algorithm, may compute a linear combination of input data using coefficients derived during machine learning processes to calculate an output datum. As a further nonlimiting example, a machine learning model 324 may be generated by creating an artificial neural network, such as a convolutional neural network including an input layer of nodes, one or more intermediate layers, and an output layer of nodes. Connections between nodes may be created by "training" the network, in which elements from a training data 304 are applied to the input nodes, and a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning, as described in detail below.

With continued reference to FIG. 3, machine learning module 300 may perform at least a supervised machine learning process 328. For the purposes of this disclosure, a "supervised" machine learning process is a process with algorithms that receive training data 304 relating one or more inputs 312 to one or more outputs 308, and seek to generate one or more data structures representing and/or instantiating one or more mathematical relations relating input 312 to output 308, where each of the one or more mathematical relations is optimal according to some criterion specified to the algorithm using some scoring function. For instance, a supervised learning algorithm may include inputs 312 described above as inputs, and outputs 308 described above as outputs, and a scoring function representing a desired form of relationship to be detected between inputs 312 and outputs 308. Scoring function may, for instance, seek to maximize the probability that a given input 312 and/or combination thereof is associated with a given output 308 to minimize the probability that a given input 312 is not associated with a given output 308. Scoring function may be expressed as a risk function representing an "expected loss" of an algorithm relating inputs 312 to outputs 308, where loss is computed as an error function representing a degree to which a prediction generated by the relation is incorrect when compared to a given input-output pair provided in training data 304. Supervised machine learning processes may include classification algorithms as defined above. A person of ordinary skill in the art, upon reviewing the entirety of this disclosure, will be aware of various possible variations of at least a supervised machine learning process 328 that may be used to determine a relation between inputs and outputs.

With continued reference to FIG. 3, training a supervised machine learning process may include, without limitation, iteratively updating coefficients, biases, and weights based on an error function, expected loss, and/or risk function. For instance, an output 308 generated by a supervised machine learning process 328 using an input example in a training example may be compared to an output example from the training example; an error function may be generated based on the comparison, which may include any error function suitable for use with any machine learning algorithm described in this disclosure, including a square of a difference between one or more sets of compared values or the like. Such an error function may be used in turn to update one or more weights, biases, coefficients, or other parameters of a machine learning model through any suitable process including without limitation gradient descent processes, least-squares processes, and/or other processes described in this disclosure. This may be done iteratively and/or recursively to gradually tune such weights, biases, coefficients, or other parameters. Updates may be performed in neural networks using one or more back-propagation algorithms. Iterative and/or recursive updates to weights, biases, coefficients, or other parameters as described above may be performed until currently available training data 304 are exhausted and/or until a convergence test is passed. For the purposes of this disclosure, a "convergence test" is a test for a condition selected to indicate that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

With continued reference to FIG. 3, a computing device, processor 102, and/or machine learning module 300 may be configured to perform method, method step, sequence of method steps, and/or algorithm described in reference to this figure, in any order and with any degree of repetition. For instance, computing device, processor 102, and/or machine learning module 300 may be configured to perform a single step, sequence, and/or algorithm repeatedly until a desired or commanded outcome is achieved; repetition of a step or a sequence of steps may be performed iteratively and/or recursively using outputs 308 of previous repetitions as inputs 312 to subsequent repetitions, aggregating inputs 312 and/or outputs 308 of repetitions to produce an aggregate result, reduction or decrement of one or more variables such as global variables, and/or division of a larger processing task into a set of iteratively addressed smaller processing tasks. A computing device, processor 102, system 100, or machine learning module 300 may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. A person of ordinary skill in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 3, machine learning process may include at least an unsupervised machine learning process 332. For the purposes of this disclosure, an unsupervised machine learning process is a process that derives inferences in datasets without regard to labels. As a result, an unsupervised machine learning process 332 may be free to discover any structure, relationship, and/or correlation provided in the data. Unsupervised processes 332 may not require a response variable, may be used to find interesting patterns and/or inferences between variables, to determine a degree of correlation between two or more variables, or the like.

With continued reference to FIG. 3, machine learning module 300 may be designed and configured to create machine learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include an elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to a person of ordinary skill in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought. Similar methods to those described above may be applied to minimize error functions, as will be apparent to a person of ordinary skill in the art upon reviewing the entirety of this disclosure.

With continued reference to FIG. 3, machine learning algorithms may include, without limitation, linear discriminant analysis. Machine learning algorithm may include quadratic discriminant analysis. Machine learning algorithms may include kernel ridge regression. Machine learning algorithms may include support vector machines, including without limitation support vector classification-based regression processes. Machine learning algorithms may include stochastic gradient descent algorithms, including classification and regression algorithms based on stochastic gradient descent. Machine learning algorithms may include nearest neighbors algorithms. Machine learning algorithms may include various forms of latent space regularization such as variational regularization. Machine learning algorithms may include Gaussian processes such as Gaussian Process Regression. Machine learning algorithms may include cross-decomposition algorithms, including partial least squares and/or canonical correlation analysis. Machine learning algorithms may include naive Bayes methods. Machine learning algorithms may include algorithms based on decision trees, such as decision tree classification or regression algorithms. Machine learning algorithms may include ensemble methods such as bagging meta-estimator, forest of randomized trees, AdaBoost, gradient tree boosting, and/or voting classifier methods. Machine learning algorithms may include neural net algorithms, including convolutional neural net processes.

With continued reference to FIG. 3, a machine learning model and/or process may be deployed or instantiated by incorporation into a program, apparatus, system, and/or module. For instance, and without limitation, a machine learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit, to represent a number according to any suitable encoding system including twos complement or the like, or may be stored in any volatile and/or non-volatile memory. Similarly, mathematical operations and input 312 and/or output 308 of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine learning process and/or model, including without limitation any combination of production and/or configuration of non-reconfigurable hardware elements, circuits, and/or modules such as without limitation application-specific integrated circuits (ASICs), production and/or configuration of reconfigurable hardware elements, circuits, and/or modules such as without limitation field programmable gate arrays (FPGAs), production and/or configuration of non-reconfigurable and/or non-rewritable memory elements, circuits, and/or modules such as without limitation non-rewritable read-only memory (ROM), other memory technology described in this disclosure, and/or production and/or configuration of any computing device and/or component thereof as described in this disclosure. Such deployed and/or instantiated machine learning model and/or algorithm may receive inputs 312 from any other process, module, and/or component described in this disclosure, and produce outputs 308 to any other process, module, and/or component described in this disclosure.

With continued reference to FIG. 3, any process of training, retraining, deployment, and/or instantiation of any machine learning model and/or algorithm may be performed and/or repeated after an initial deployment and/or instantiation to correct, refine, and/or improve the machine learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs 308 of machine learning models and/or algorithms, and/or errors and/or error functions thereof, to any thresholds, convergence tests, or the like, and/or may compare outputs 308 of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

With continued reference to FIG. 3, retraining and/or additional training may be performed using any process for training described above, using any currently or previously deployed version of a machine learning model and/or algorithm as a starting point. Training data for retraining may be collected, preconditioned, sorted, classified, sanitized, or otherwise processed according to any process described in this disclosure. Training data 304 may include, without limitation, training examples including inputs 312 and correlated outputs 308 used, received, and/or generated from any version of any system, module, machine learning model or algorithm, apparatus, and/or method described in this disclosure. Such examples may be modified and/or labeled according to user feedback or other processes to indicate desired results, and/or may have actual or measured results from a process being modeled and/or predicted by system, module, machine learning model or algorithm, apparatus, and/or method as "desired" results to be compared to outputs 308 for training processes as described above. Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

With continued reference to FIG. 3, one or more processes or algorithms described above may be performed by at least a dedicated hardware unit 336. For the purposes of this disclosure, a "dedicated hardware unit" is a hardware component, circuit, or the like, aside from a principal control circuit and/or processor 102 performing method steps as described in this disclosure, that is specifically designated or selected to perform one or more specific tasks and/or processes described in reference to this figure, such as without limitation preprocessing and/or sanitization of training data and/or training a machine learning algorithm and/or model. Dedicated hardware unit 336 may include, without limitation, a hardware unit that can perform iterative or massed calculations, such as matrix-based calculations to update or tune parameters, weights, coefficients, and/or biases of machine learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously, in parallel, and/or the like. Such dedicated hardware units 336 may include, without limitation, graphical processing units (GPUs), dedicated signal processing modules, field programmable gate arrays (FPGA), other reconfigurable hardware that has been configured to instantiate parallel processing units for one or more specific tasks, or the like. Computing device, processor 102, system 100, or machine learning module 300 may be configured to instruct one or more dedicated hardware units 336 to perform one or more operations described herein, such as evaluation of model and/or algorithm outputs, one-time or iterative updates to parameters, coefficients, weights, and/or biases, vector and/or matrix operations, and/or any other operations described in this disclosure.

Figure 4:
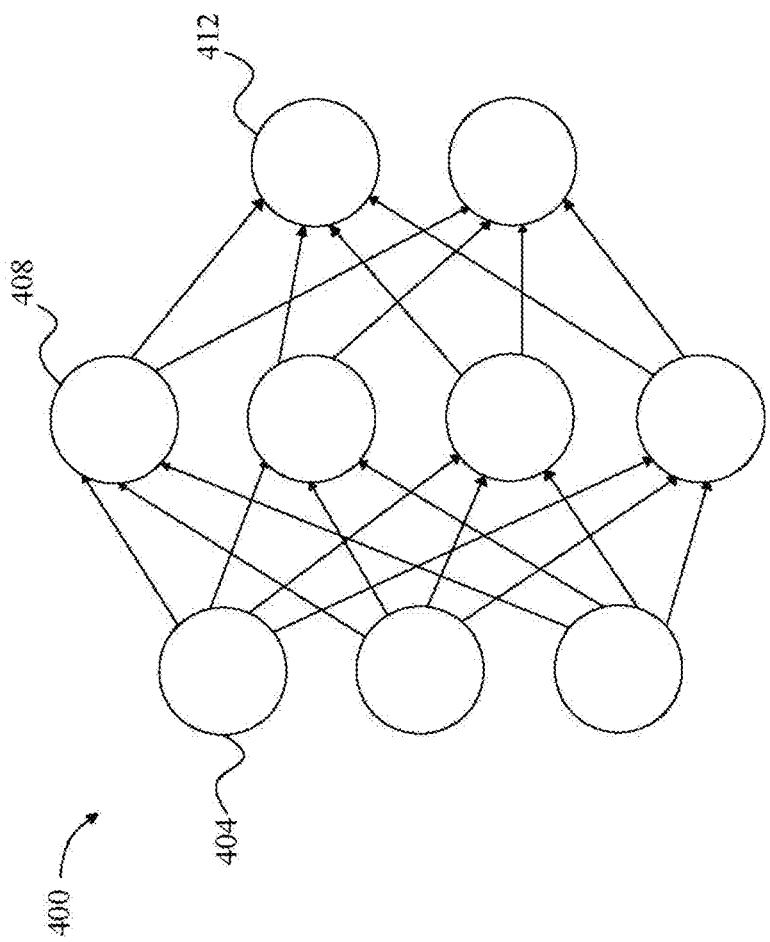
FIG. 4 is a block diagram of an exemplary embodiment of a neural network.

Referring now to FIG. 4, an exemplary embodiment of neural network 400 is illustrated. For the purposes of this disclosure, a neural network or artificial neural network is a network of "nodes" or data structures having one or more inputs, one or more outputs, and a function determining outputs based on inputs. Such nodes may be organized in a network, such as without limitation a convolutional neural network, including an input layer of nodes 404, at least an intermediate layer of nodes 408, and an output layer of nodes 412. Connections between nodes may be created via the process of "training" neural network 400, in which elements from a training dataset are applied to the input nodes, and a suitable training algorithm (such as Levenberg-Marquardt, conjugate gradient, simulated annealing, or other algorithms) is then used to adjust the connections and weights between nodes in adjacent layers of the neural network 400 to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network". As a further nonlimiting example, neural network 400 may include a convolutional neural network including an input layer of nodes 404, one or more intermediate layers of nodes 408, and an output layer of nodes 412. For the purposes of this disclosure, a "convolutional neural network" is a type of neural network 400 in which at least one hidden layer is a convolutional layer that convolves inputs to that layer with a subset of inputs known as a "kernel", along with one or more additional layers such as pooling layers, fully connected layers, and the like.

Figure 5:
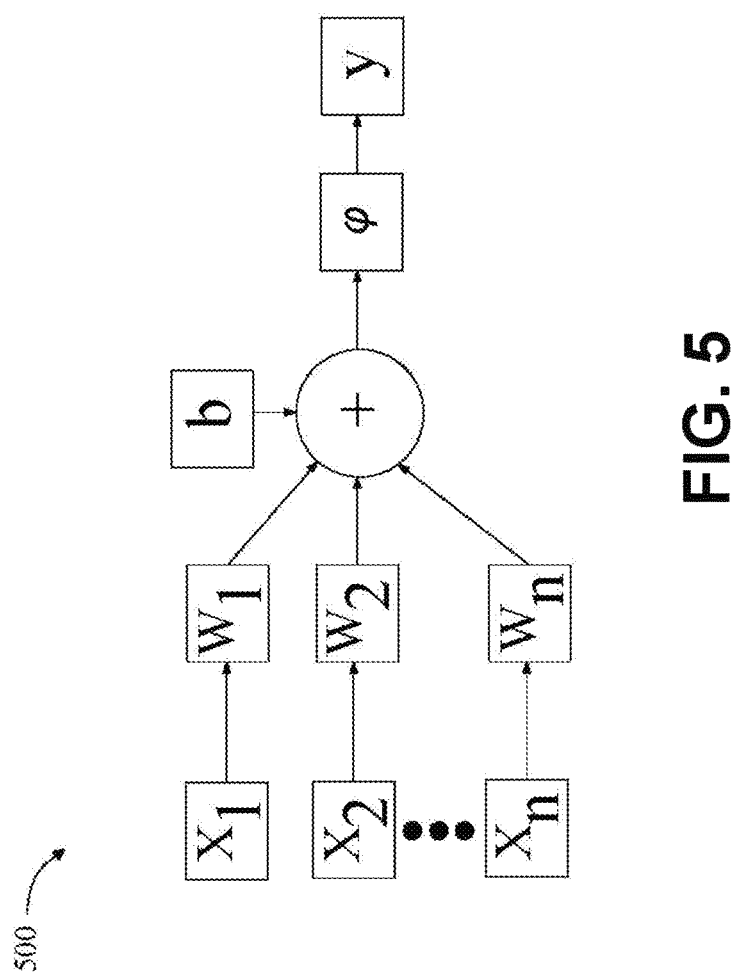
FIG. 5 is a block diagram of an exemplary embodiment of a node of a neural network.

Referring now to FIG. 5, an exemplary embodiment of a node 500 of neural network 400 is illustrated. Node 500 may include, without limitation, a plurality of inputs, xi, that may receive numerical values from inputs to neural network 400 containing the node 500 and/or from other nodes 500. Node 500 may perform one or more activation functions to produce its output given one or more inputs, such as without limitation computing a binary step function comparing an input to a threshold value and outputting either a logic 1 or logic 0 output or its equivalent, a linear activation function whereby an output is directly proportional to input, and/or a nonlinear activation function wherein the output is not proportional to the input. Nonlinear activation functions may include, without limitation, a sigmoid function of the form $$f(x) = \frac{1}{1-e^{-x}}$$

given input x, a tanh (hyperbolic tangent) function of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some value of a, an exponential linear units function such as $$f(x) = \begin{cases} x & \text{for } x \geq 0 \\ \alpha(e^x - 1) & \text{for } x < 0 \end{cases}$$

for some value of α (this function may be replaced and/or weighted by its own derivative in some embodiments), a softmax function such as $$f(x_i) = \frac{e^x}{\Sigma_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs $x_i$, that may be used as activation functions. As a nonlimiting and illustrative example, node 500 may perform a weighted sum of inputs using weights, $w_i$, that are multiplied by respective inputs, $x_i$. Additionally or alternatively, a bias b may be added to the weighted sum of the inputs such that an offset is added to each unit in a neural network layer that is independent of the input to the layer. The weighted sum may then be input into a function, φ, which may generate one or more outputs, y. Weight, $w_i$, applied to an input, $x_i$, may indicate whether the input is "excitatory", indicating that it has strong influence on the one or more outputs, y, for instance by the corresponding weight having a large numerical value, or "inhibitory", indicating it has a weak influence on the one more outputs, y, for instance by the corresponding weight having a small numerical value. The values of weights, $w_i$, may be determined by training neural network 400 using training data, which may be performed using any suitable process as described above.

Figure 6:
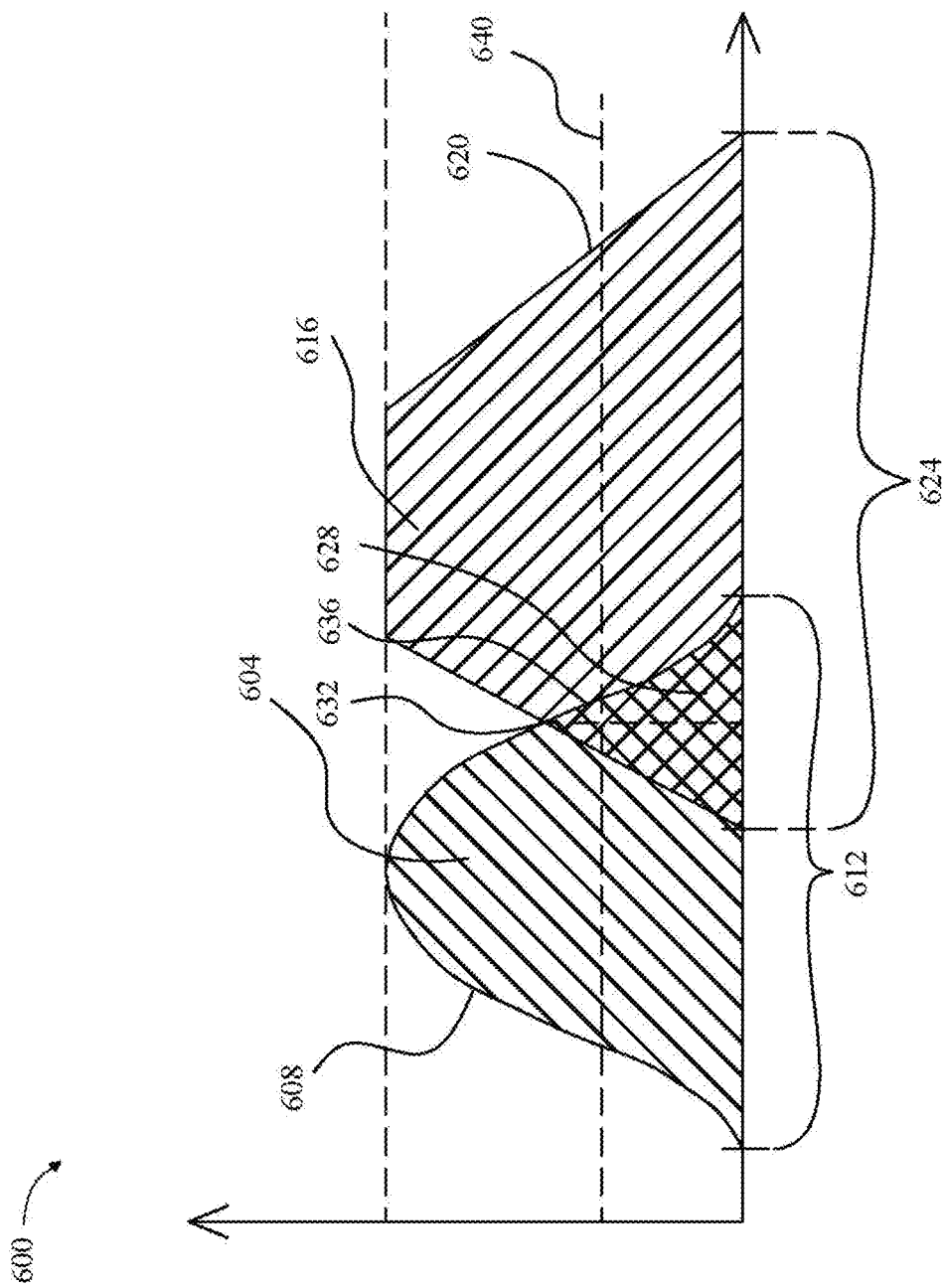
FIG. 6 is an illustration of an exemplary embodiment of fuzzy set comparison.

Referring now to FIG. 6, an exemplary embodiment of fuzzy set comparison 600 is illustrated. A first fuzzy set 604 may be represented, without limitation, according to a first membership function 608 representing a probability that an input falling on a first range of values 612 is a member of the first fuzzy set 604, where the first membership function 608 has values on a range of probabilities such as without limitation the interval [0,1], and an area beneath the first membership function 608 may represent a set of values within the first fuzzy set 604. Although first range of values 612 is illustrated for clarity in this exemplary depiction as a range on a single number line or axis, first range of values 612 may be defined on two or more dimensions, representing, for instance, a Cartesian product between a plurality of ranges, curves, axes, spaces, dimensions, or the like. First membership function 608 may include any suitable function mapping first range of values 612 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, & \text{for } x > c \text{ and } x < a \\ \frac{x-a}{b-a}, & \text{for } a \le x < b \\ \frac{c-x}{c-b}, & \text{if } b < x \le c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:
a Gaussian membership function may be defined as:

$$y(x, a, c) = \frac{1}{1 - e^{-a(x-c)}}$$

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

A person of ordinary skill in the art, upon reviewing the entirety of this disclosure, will be aware of various alternative or additional membership functions that may be used consistently with this disclosure.

With continued reference to FIG. 6, in one or more embodiments, first fuzzy set 604 may represent any value or combination of values as described above, including output from one or more machine learning models. A second fuzzy set 616, which may represent any value which may be represented by first fuzzy set 604, may be defined by a second membership function 620 on a second range 624; second range 624 may be identical and/or overlap with first range of values 612 and/or may be combined with first range via Cartesian product or the like to generate a mapping permitting evaluation overlap of first fuzzy set 604 and second fuzzy set 616. Where first fuzzy set 604 and second fuzzy set 616 have a region 628 that overlaps, first membership function 608 and second membership function 620 may intersect at a point 632 representing a probability, as defined on probability interval, of a match between first fuzzy set 604 and second fuzzy set 616. Alternatively, or additionally, a single value of first and/or second fuzzy set may be located at a locus 636 on first range of values 612 and/or second range 624, where a probability of membership may be taken by evaluation of first membership function 608 and/or second membership function 620 at that range point. A probability at 628 and/or 632 may be compared to a threshold 640 to determine whether a positive match is indicated. Threshold 640 may, in a nonlimiting example, represent a degree of match between first fuzzy set 604 and second fuzzy set 616, and/or single values therein with each other or with either set, which is sufficient for purposes of the matching process; for instance, threshold 640 may indicate a sufficient degree of overlap between an output from one or more machine learning models. Alternatively or additionally, each threshold 640 may be tuned by a machine learning and/or statistical process, for instance and without limitation as described in further detail in this disclosure.

With continued reference to FIG. 6, in one or more embodiments, a degree of match between fuzzy sets may be used to classify query 144, one or more query features therein, and/or one or more query factors therein, as described above in this disclosure. In one or more embodiments, a degree of match between fuzzy sets may be used to identify at least a patient, at least a reference ECG 114, and/or at least a reference EHR 108. In some cases, such task may be accomplished by matching a first set of statistical parameters from query 144 with a second set of statistical parameters from reference ECG 114 or reference EHR 108, as described above in this disclosure. As a nonlimiting example, if one or more query features are associated with a fuzzy set that matches a fuzzy set of a cohort by having a degree of overlap exceeding a threshold, computing device may classify the query feature as belonging to that cohort. Where multiple fuzzy matches are performed, degrees of match for each respective fuzzy set may be computed and aggregated through, for instance, addition, averaging, or the like, to determine an overall degree of match.

With continued reference to FIG. 6, in one or more embodiments, query 144, one or more query features therein, and/or one or more query factors therein may be compared to multiple fuzzy sets of multiple cohorts. As a nonlimiting example, query feature may be represented by a fuzzy set that is compared to each of the multiple fuzzy sets of multiple cohorts, and a degree of overlap exceeding a threshold between the fuzzy set representing the query feature and any of the multiple fuzzy sets representing multiple cohorts may cause computing device to classify the query feature as belonging to that cohort. As a nonlimiting example, there may be two fuzzy sets representing two cohorts, cohort A and cohort B. Cohort A may have a cohort A fuzzy set, cohort B may have a cohort B fuzzy set, and query feature may have a query feature fuzzy set. Computing device may compare query feature fuzzy set with each of cohort A fuzzy set and cohort B fuzzy set, as described above, and classify the query feature to either, both, or neither of cohort A fuzzy set and cohort B fuzzy set. Similar principles may apply to classification of query factors as well. Machine learning methods as described throughout this disclosure may, in a nonlimiting example, generate coefficients used in fuzzy set equations as described above, such as without limitation x, c, and σ of a Gaussian set as described above, as outputs of machine learning methods. Likewise, data such as reference ECG 114, reference EHR 108, query 144, and/or elements related thereto may be used indirectly to determine a fuzzy set, as the fuzzy set may be derived from outputs of one or more machine learning models that take these data directly or indirectly as inputs.

With continued reference to FIG. 6, in one or more embodiments, fuzzy set comparison 600 may include a fuzzy inference model. For the purposes of this disclosure, a "fuzzy inference model" is a model that uses fuzzy logic to reach a decision and derive a meaningful outcome. As a nonlimiting example, a fuzzy inference system may be associated with degrees of a medical condition, such as "Normal", "Grade 1", "Grade 2", "Grade 3", and "Indeterminate". In one or more embodiments, an inferencing rule may be applied to determine a fuzzy set membership of a combined output based on the fuzzy set membership of linguistic variables. As a nonlimiting example, membership of a combined output in a "Grade 3" fuzzy set may be determined based on a percentage membership of a second linguistic variable with a first mode in an "Grade 3" fuzzy set and a percentage membership of a second linguistic variable associated with a second mode in a "Grade 2" fuzzy set. In one or more embodiments, parameters of observation machine learning model 128a-n may then be determined by comparison to a threshold or output using another defuzzification process. Each stage of such a process may be implemented using any type of machine learning model, such as any type of neural network, as described herein. In one or more embodiments, parameters of one or more fuzzy sets may be tuned using machine learning. In one or more embodiments, fuzzy inferencing and/or machine learning may be used to synthesize outputs of plurality of observation machine learning model 128a-n. In some cases, outputs such as observation outcomes 152a-n may be combined to make an overall or final determination, which may be displayed with or instead of individual outputs, consistent with details described above. As another nonlimiting example, outputs may be ranked, wherein the output with the highest confidence score may be the output displayed at display device 160 or displayed first in a ranked display of result outputs, consistent with details described above.

Figure 7:
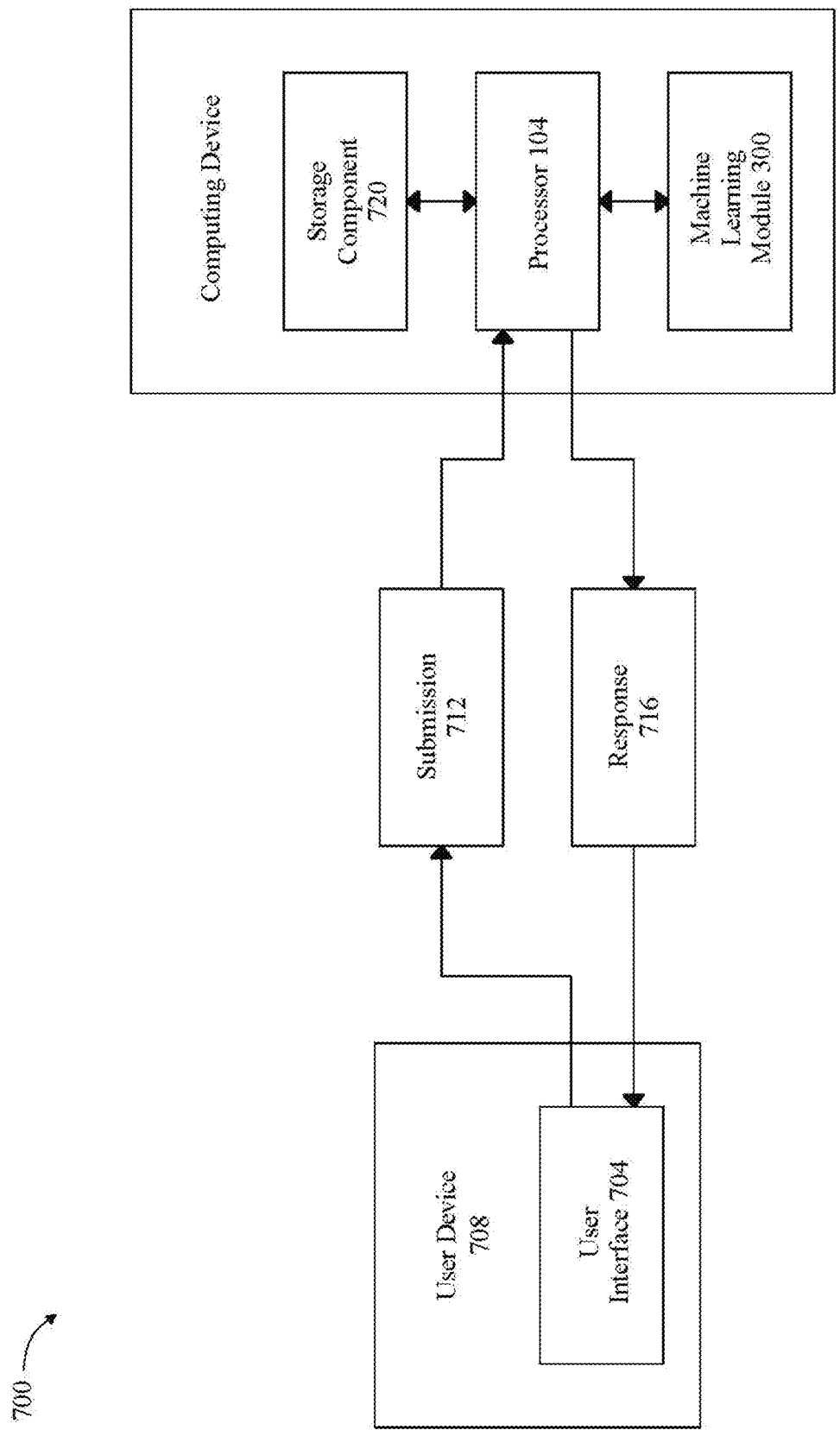
FIG. 7 is an exemplary embodiment of a chatbot system.

Referring now to FIG. 7, in one or more embodiments, system 100 may perform one or more of its functions, such as outputting at least an observation outcome 152a-n, by implementing at least a chatbot system 700, an exemplary embodiment of which is schematically illustrated. In one or more embodiments, a user interface 704 may be communicatively connected with a computing device that is configured to operate a chatbot. In some cases, user interface 704 may be local to computing device. Alternatively, or additionally, in some other cases, user interface 704 may be remote to computing device, e.g., as part of a user device 708, and communicative with the computing device and processor 102 therein, by way of one or more networks, such as without limitation the internet. Alternatively, or additionally, user interface 704 may communicate with user interface 704 and/or computing device using telephonic devices and networks, such as without limitation fax machines, short message service (SMS), or multimedia message service (MMS). Commonly, user interface 704 may communicate with computing device using text-based communication, for example without limitation using a character encoding protocol, such as American Standard for Information Interchange (ASCII). Typically, user interface 704 may conversationally interface a chatbot, by way of at least a submission 712, from the user interface 704 to the chatbot, and a response 716, from the chatbot to the user interface 704. In many cases, one, or both, of submission 712 and response 716 are text-based communication. Alternatively, or additionally, in some cases, one or both of submission 712 and response 716 are audio-based communication.

With continued reference to FIG. 7, submission 712, once received by user interface 704 and/or computing device that operates a chatbot, may be processed by processor 102. In one or more embodiments, processor 102 may process submission 712 using one or more of keyword recognition, pattern matching, and natural language processing. In one or more embodiments, processor 102 may employ real-time learning with evolutionary algorithms. In one or more embodiments, processor 102 may retrieve a pre-prepared response from at least a storage component 720, based upon submission 712. Alternatively, or additionally, in one or more embodiments, processor 102 may communicate a response 716 without first receiving a submission 712, thereby initiating a conversation. In some cases, processor 102 may communicate an inquiry to user interface 704 and/or computing device, wherein processor 102 is configured to process an answer to the inquiry in a following submission 712 from the user interface 704 and/or computing device. In some cases, an answer to an inquiry presented within submission 712 from user interface 704 and/or computing device may be used by the computing device as an input to another function.

Figure 8:
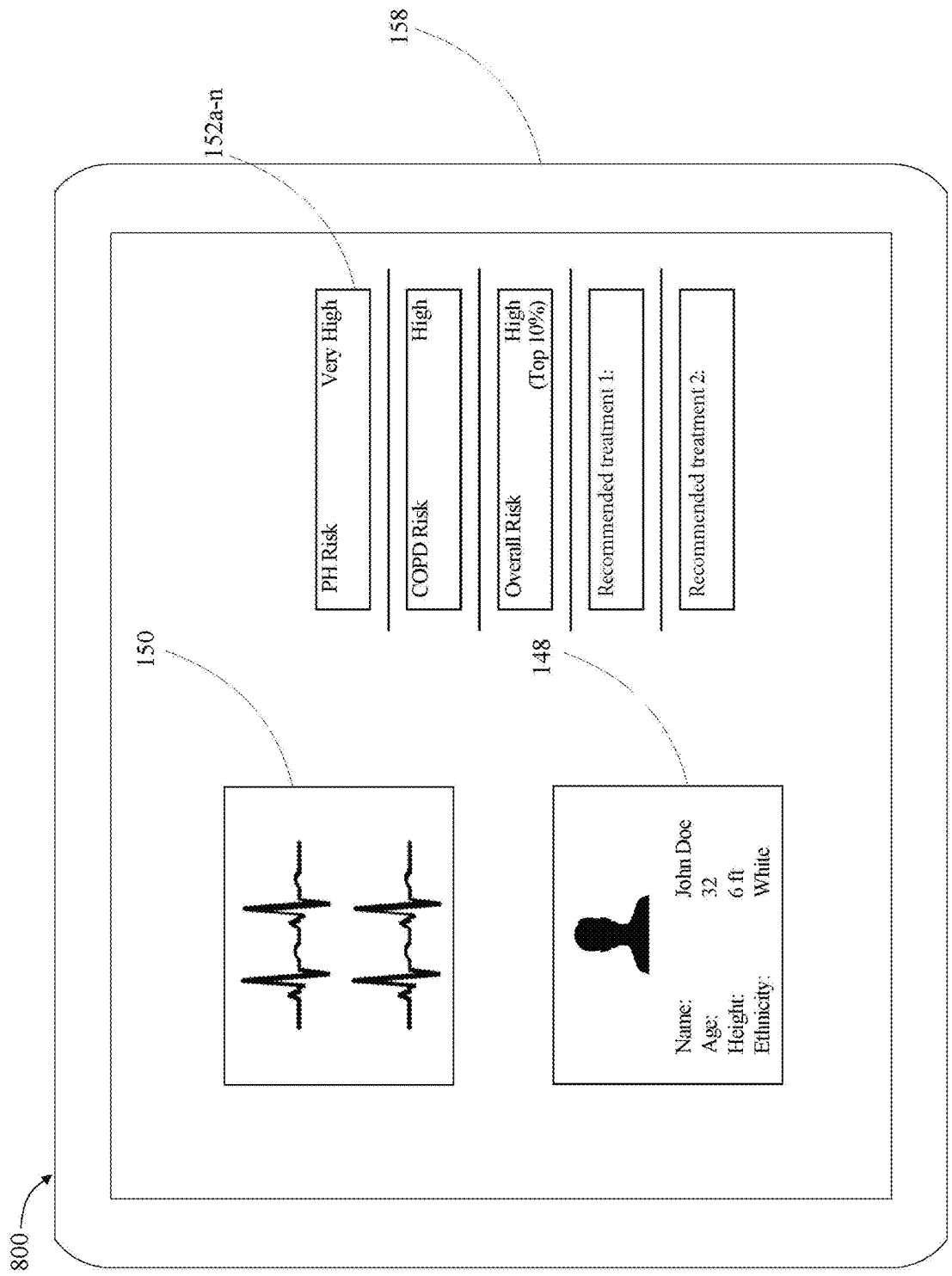
FIG. 8 is an exemplary embodiment of a graphical user interface.

Referring now to FIG. 8, an exemplary GUI 800 is included to demonstrate the functions of system 100. GUI 900 includes a query ECG 150 collected from subject and query EHR 148 retrieved from data repository 106 that pertains to the subject. System 100 uses query features and/or query factors extracted therefrom and observation machine learning model 128a-n trained using medical training data 116 to output observation outcomes 152a-n, e.g., the risk of subject having or developing a case of PH or COPD.

Examples

Referring now to FIGS. 9A-C, 10-12, an exemplary study pertaining to system 100 is illustrated.

1. ABSTRACT

Title of the Study: characterizing pulmonary hypertension due to chronic obstructive pulmonary disease (PH-COPD) and developing a machine learning (ML) algorithm.

Background/Study Rationale: given the lack of treatments and the need for an invasive procedure to diagnose PH-COPD, it is challenging to identify patients who have PH-COPD and may benefit from a PH-specific therapy.

Results from this study were used to develop a machine learning model that can aid in identifying patients likely to have PH-COPD and benefit from therapy. If successful, the model will be validated in other datasets and submitted for qualification by the FDA/EMA to enable its external use.

The objectives of this study are to: i) characterize confirmed PH-COPD diagnosis vs. suspected PH-COPD diagnosis vs. explicitly ruled out PH-COPD diagnosis; ii) develop a preliminary machine learning (ML) algorithm; and iii) estimate prevalence of PH-COPD among patients with COPD across a variety of clinical settings.

Study Design: first, retrospective data may be used for a descriptive analysis of COPD patients using real-world data collected at the Mayo Clinic. Additionally, input from clinicians may be used to ascertain additional patient characteristics that was used to train the algorithm to better identify patients with suspected PH-COPD. Features may also originate directly from clinicians and their experience in treating the condition of interest.

Study Population: Patients with COPD or COPD and PH between 2015-2019

Exposure & Outcome: Correct identification of patients with PH-COPD

Study Setting: This study may use retrospective patient EHR data from the Mayo Clinic.

Statistical Methods: Descriptive statistics for feature space covariates, Cohen's d, t-tests, chi-squared and odds ratios may be performed depending on the type of feature (continuous versus categorical) for a univariate analysis. A multivariate logistic regression analysis may be used to examine the influencing factors between the COPD and PH COPD cohorts. Performance metrics such as AUC, sensitivity, specificity, diagnostic odds ratio, PPV and NPV may be used in algorithm development.

Results: For the four different models (EHR only [supervised], EHR only [self-supervised], ECG only and ECG+ EHR), all AUCs were greater than or equal to 0.79, indicating a high level of discriminative ability between COPD patients with and without PH. Based on the three best performing models (EHR only [self-supervised], ECG only and ECG+EHR), the sensitivity-corrected prevalence of PH in COPD populations were as follows: 6.87%, 5.92% and 6.77%, respectively.

Conclusions: The findings of this study indicate that PH-COPD patients have distinct clinical profiles from COPD-only patients and further understanding of this group may help clinicians identify patients who may benefit from PH-COPD screening. The results also show that models may be leveraged in a clinical system to improve detection of PH among COPD patients. This could facilitate PH-COPD patient referrals to PH specialty centers for individualized care in accordance with current guidelines, potentially improving clinical outcomes.

2. STUDY OBJECTIVES

This study aimed to identify the key clinical characteristics and patterns suggesting a patient has PH-COPD, as identified by an algorithm. Data regarding patient characteristics may be ascertained via natural language processing (NLP), input from clinicians, and machine learning (ML) modeling. Upon completion, results from this project may: (1) curate high quality cohorts of PH-COPD and control patients with complete structured and unstructured clinical records collected in the context of routine clinical care; (2) implement an algorithm for identifying patients with high likelihood of having PH-COPD; (3) evaluate performance of the algorithm in the healthcare system's EMR databases by commonly used metrics (e.g., PPV, NPV, sensitivity, specificity, AUROC, AUPR) or alternative metrics if these cannot be calculated; (4) apply resulting algorithm to large scale unlabeled data from the healthcare system to estimate population prevalence.

2.1 Primary Objectives

1). Characterize 3 populations of patients: (1) confirmed PH-COPD diagnosis; (2) suspected PH-COPD diagnosis; and (3) explicitly ruled out PH-COPD diagnosis (e.g., clinical characteristics, echocardiography data, lab values, PFT values, sequence of symptoms). Specifically,
  a. Identify clinical characteristics that raise suspicion of PH among COPD patients
  b. Describe the patient journey: a descriptive summary of presenting symptoms, referral patterns, diagnostic tests, etc.

2). Develop a preliminary machine learning (ML) algorithm

3). Estimate prevalence of PH-COPD among patients with COPD across a variety of clinical settings (e.g. among all PH patients identified using RHC and Echo values, PH patients with mPAP≥25 versus ≥20, and PH patients with confirmatory RHC data only, combined with the predicted PH-COPD patients from the screening cohort)

3. Research Methods 3.1 Study Design

Descriptive analysis of COPD patients may be performed using structured real-world data collected from the EHR at the Mayo Clinic. Simultaneously, clinical characteristics that raise suspicion of PH among COPD patients may be received from clinicians. A machine learning algorithm may be trained (as described in Section 3.3.3) to identify undiagnosed PH patients more easily in the clinic. For this study, the feature space may consist of covariates from both structured and unstructured EHR data sources including demographics, comorbid diagnoses, lab test results, and measurements collected during ECHO, RHC, ECG, and other procedures. Performance was evaluated using metrics such as area under the curve (AUC), sensitivity and specificity.

3.3 Study Population

The populations of interest may include all patients who are confirmed or strongly suspected of PH-COPD and are diagnosed between 2015 and 2019. These dates were chosen because they capture modern treatment practices, but are not impacted by the COVID pandemic, which may have significantly impacted RWE treatment patterns and observed symptoms and associated cardiac and pulmonary conditions. Patients may be selected into the study if they fulfilled all the inclusion criteria and none of the exclusion criteria outlined below. The study population may include three cohorts of patients: a negative cohort (i.e., COPD-only), positive cohort (i.e., PH-COPD) and an unconfirmed screening PH COPD cohort (i.e. COPD patients without RHC or Echo data confirming or ruling-out PH).

The index date for inclusion in the analysis may be defined as: PH diagnosis date. In the PH-COPD cohort, EHR data in predefined temporal windows relative to PH diagnosis date was used. In the COPD-only cohort, EHR data in predefined temporal windows prior to the rule-out echo/ RHC was used.

Section Sixty (60) patient IDs from each of these cohorts may be randomly selected and manually reviewed by blinded clinical scientists. The process for patient review may include the following steps:

Random selection of de-identified patients from the positive, negative, and screening cohorts The clinical scientists were blinded to the generated cohort labels.

The number of patients with each investigator-reviewed label was compared against the generated labels from the platform.

Decision-rules around re-stratifying cohorts were defined based upon level of agreement and need for additional chart reviews.

3.3.1 Inclusion Criteria

All inclusion and exclusion criteria may be reviewed by the investigator or qualified designee to ensure that the subject qualifies for the study.

Structured codes to identify patients with COPD at the Mayo Clinic, as well as other information from the electronic medical record may be used to define three populations, as described below:

1). PH-COPD diagnosis.
  a. Patients diagnosed with PH-COPD, defined as:
    i. Either:
      1. mPAP≥25 mmHg (eligible for FDA-approved PH treatment)
      2. mPAP>20 mmHg (reflects latest ESC/ERS guidelines for PH diagnosis), or
      3. mPAP>20 mmHg or if no RHC data available, TRV>3.4 m/s (confirmed PH via RHC plus high likelihood of PH by echo)

Note, all measurements may be taken at baseline, i.e. at rest and not during challenge. PH diagnosis date may be defined as the earliest date at which either mPAP or TRV exceeded the specified threshold ii. Presence of one (1) of the following:
      1. ICD code for COPD preceding PH diagnosis date or within 3 months following PH diagnosis
      2. Positive sentiment ("confirmatory language") for COPD preceding PH diagnosis from notes using NLP or within 3 months following PH diagnosis.
        a. For example, a note on Jul. 23, 2009: "Patient was diagnosed with COPD", which would occur before a PH diagnosis by RHC on Oct. 2, 2012.
      3, and does not have Group 1 (Pulmonary Arterial Hypertension ["PAH"]), Group 2, or Group 4 PH, as defined in section 3.3.2.

2). Explicitly ruled out PH-COPD diagnosis
  b. COPD-only (i.e., without a diagnosis of PH), confirmed via RHC:
    i. All RHCs have mPAP≤20 mmHg and no TRV>3.4 m/s prior to last RHC OR all TRV≤2.8 m/s by Transthoracic Echocardiogram if no RHC was performed
    ii. Presence of one (1) of the following:
      1. ICD code for COPD
      2. Positive sentiment ("confirmatory language") for COPD from notes 3). COPD patients with unconfirmed PH status
  c. Screening cohort (Has COPD, does not have RHC or Echo)
    i. Has either structured diagnosis or confirmatory language for COPD, and
    ii. Is not in any of the exclusion cohorts listed in section 3.3.2 below.

3.3.2 Exclusion criteria
  All Cohorts:
  Patient is <18 yo at time of diagnosis
  Patient has retracted standing research authorization agreement with Mayo Clinic
  And does not have Group 1 (PAH), Group 2, or Group 4 PH, defined as:
  1). Group 1 (PAH): patients may be required to meet all criteria to be considered Group 1.
    a. mPAP≥20 mmHg at baseline. Baseline refers to the phase of the RHC itself when the patient is at rest (not during exercise) and has not been administered a drug challenge of any kind. Note, this definition is according to the latest ESC/ERS guidelines for PH diagnosis
    b. Limit to precapillary patients:
      i. PVR≥2.0 WU
      ii. PCWP≤15 mmHg
    c. Use of at least one (1) PAH medication at any time
      i. Medication list: Ambrisentan, Ambrisentan, Bosentan, Epoprostenol, Iloprost, Macitentan, Selexipag, Sildenafil, Treprostinil, Tadalafil
  2). Group 2 PH: patients may be required to meet all criteria to be considered Group 2.
    a. mPAP≥20 mmHg at baseline
    b. Presence of one (1) of the following for the Group 2 diseases of interest (left ventricular systolic or diastolic dysfunction, valvular heart disease, left heart inflow and outflow obstructions not due to valvular disease and congenital cardiomyopathies)
    c. ICD code for disease(s) of interest within 3 months of PH diagnosis (date of mPAP≥20 mmHg)
    d. Positive sentiment ("confirmatory language") for disease(s) of interest within 3 months PH diagnosis or PH secondary to disease(s) of interest from notes using NLP
  3). Group 4 PH: patients may be required to meet all criteria to be considered Group 4.
    a. mPAP & 20 mmHg at baseline
    b. Limit to precapillary patients:
      i. PVR≥2.0 WU
      ii. PCWP≤15 mmHg
    c. Presence of one (1) of the following:
      i. ICD code for CTEPH (date of mPAP≥20 mmHg)
      ii. Positive sentiment ("confirmatory language") for CTEPH from notes using NLP.

3.3.3 Development of PH Detection Algorithm

The algorithm's feature space contained data elements from both structured and unstructured sources. Based on the feature space fill rates, positive and negative cohorts may be refined, and positive and negative cohorts may be randomized into respective algorithm training and test sets.

Once the algorithm was trained, the performance may be evaluated using analyses described in Section 4.2.1 on its corresponding test set.

When training the algorithm, the following may be considered to improve acceptability by users:

Whether algorithm inputs may contain structured data that can be automatically extracted from the EHR system.

Whether certain features may require manual review of patient charts.

Whether a variable may require a significant number of patients to undergo an additional laboratory test or other procedure and how easy/difficult it is to do that test or procedure. For example, NT-proBNP may not be routinely collected in clinical practice but may be an easily obtained lab test. Similarly, PFTs may not be collected/recorded regularly in all patients but are extremely easy to obtain.

3.4 Setting

This study may use retrospective EHR data from the Mayo Clinic Health System (Minnesota, Florida, Arizona sites and all community centers) between 2015-2019. No contingency measures were implemented to manage study conduct because of the pandemic.

3.5 Outcomes of Interest

This study has no health outcomes. Our outcome of interest may be the correct identification of patients with PH-COPD, as identified with the algorithm developed using the definitions listed above in Section 3.3.1

3.6 Description of Covariates

The objective of this algorithm may be to determine what combination of salient covariates distinguish PH-COPD patients from COPD-only controls to identify undiagnosed patients more easily in the clinic. For this study, the feature space may consist of covariates including demographics, structured and unstructured diagnoses, lab tests, and measurements collected during ECHO, RHC, ECG, and/or other procedures. To maximize the degree of coverage across all covariates, there may be different temporal windows preceding PH or following COPD diagnosis (e.g., 3 months, 6 months, 9 months, 1 year, etc.). The PH diagnosis may be used as the index date, so the time windows prior to PH diagnosis but following COPD diagnosis may be considered. Because the intended use population of the algorithm is patients with COPD, patients diagnosed with PH on the same date as COPD may not be used for training because there's no time window with data at which they have a sole COPD diagnosis without concurrent PH diagnosis and thus this algorithm would not be applicable.

In cases where data coverage for a specific feature was <15% of the cohort, the associated data type was dropped.

To characterize the study cohorts, the following features may be assessed
1). Demographics
   a. Age at diagnosis
   b. Race/ethnicity
   c. Gender
   d. Record longitudinally
      i. Time from first record to COPD diagnosis
      ii. Time from COPD diagnosis to last record at Mayo
   e. Death
      i. N (%) patients who have since died
      ii. Time from COPD diagnosis to death
2). Observations
   a. Heart rate
   b. Blood pressure
   c. Height
   d. Weight
   e. Smoking status
   f. Alcohol use
   g. Exercise
3). ECG:
   a. QT interval
   b. P-wave
   c. QRS durations
4). Echo (as available):
   a. TRV—tricuspid regurgitation velocity
   b. IVC (inferior vena cava) diameter
   c. TAPSE—tricuspid annular plane systolic excursion
   d. RVFAC—right ventricular fractional area change
   e. RVSP— right ventricular systolic pressure
   f. RV/LV ratio—right ventricular to left ventricular diameter ratio
   g. RV (right ventricular) size/mass/wall thickness
   h. RV strain
   i. PE—pulmonary embolism
   j. SV— stroke volume (derived, include method of acquisition)
   k. EF—ejection fraction (derived, include method of acquisition)
   l. Myocardial performance index (aka Tei index)
   m. RA (right atrium) and LA (left atrium) size
   n. RVOT VTI—Right ventricular outflow tract velocity time integral
   o. PASP—pulmonary artery systolic pressure
   p. LVEDV—left ventricular end-diastolic volume
   q. LVEF—left ventricular ejection fraction
   r. LV (left ventricular) mass
   s. sPAP—systolic pulmonary arterial pressure
5). Laboratory tests:
   a. BNP— brain natriuretic peptide
   b. NT-proBNP—N-terminal pro b-type natriuretic peptide
   c. eGFR—Estimated glomerular filtration rate
   d. Creatinine
   e. Uric Acid
   f. Anemia
      i. Hemoglobin
      ii. Hematocrit
      iii. Red blood counts
   g. Iron
      i. Serum iron
      ii. Serum ferritin
      iii. Serum transferrin
      iv. Transferrin saturation
   h. Sodium
   i. Red blood cell width distribution
6). Medication history
   a. Diuretics
   b. Inhalers
   c. Bronchodilators
   d. COPD medications including Phosphodiesterase-4 inhibitors, Theophylline, and oral steroids.
7). Other procedures/tests
   a. CT scan: lung/chest CT scan, cardiac CT
   b. VQ scan
   c. X-ray: lung/chest x-ray
   d. Pulmonary function test e. 6-minute walk test f. Oxygen use
8). Healthcare resource utilization
   a. Days hospitalized
   b. Emergency department visits
   c. Visits to Mayo
   d. Healthcare provider specialty (if available at desired level of specificity)
   e. Lung or Heart/lung Transplant procedure
   f. Other procedures/tests
9). Data from unstructured clinical notes using the disease diagnosis model:
   a. Symptoms (both presence and noted absence):
      i. Dyspnea
      ii. Chest pain
      iii. Edema of lower limbs
      iv. Fatigue
      v. Dizziness
      vi. Fainting
      vii. Heart palpitations
      viii. Cyanosis As inputs to the algorithm, symptoms from unstructured clinical notes in the patients' EHRs may be extracted using the disease diagnosis Augmented Curation model. The neural network used to perform disease diagnosis classification may be initially trained using 18,490 sentences containing nearly 250 different cardiovascular, pulmonary, and metabolic diseases and phenotypes. Each sentence may be manually classified into one of four categories: 'Yes' (confirmed phenotype), 'No' (ruled out phenotype), 'Maybe' (suspected phenotype), and 'Other' (alternate context, e.g., family history of a phenotype, risk of adverse event from medication, etc.). Using a 90%:10% train:test split, the model achieved 93.6% overall accuracy and a precision and recall of 95% or better for both positive and negative sentiment classification.

3.7 Study Procedures 3.7.1 Ethics Review

The database used within the platform may contain only de-identified patient information (i.e., does not include names, addresses, social security or medical record numbers or other obvious identifiers), and is fully compliant with the HIPAA. Therefore, no ethics review was necessary. Confidentiality of patient records were maintained at all times. All study reports contained aggregate data only and did not identify individual patients. At no time during the study did the sponsor receive patient identifying information.

3.7.2 Subject Information and Informed Consent

This study required informed consent.

Inclusion in this study may be in accordance with their standing research authorization agreement with Mayo Clinic. If a patient retracts said authorization, they are automatically removed from the database and will not appear in any analyses.

This study may require IRB/EC review.

Investigators may ensure that personal identifiers were removed from any study files that are accessible to non-study personnel in accordance with applicable laws and regulations.

Whenever feasible, study files may be coded and stripped of personal identifiers, and code keys may be stored separate from study files.

The participant was allowed as much time as wished to consider the information, and the opportunity to question the investigator or other independent parties to decide whether they would participate in the study. Electronic ICF was then obtained using the participant's dated signature and the dated signature of the person who presented and obtained the ICF. The person who obtained the consent may be suitably qualified and experienced and have been authorized to do so by the Chief/Principal Investigator. A digital copy of the signed Informed Consent was given to the participant. The original signed electronic form was retained.

3.8 Data Handling and Validation/Data Management/Data Quality Assurance

All data collected for the study was recorded accurately, promptly, and legibly. The investigator or qualified designee was responsible for recording and verifying the accuracy of subject data. By signing this protocol, the investigator acknowledges that his/her electronic signature is the legally binding equivalent of a written signature. By entering his/her electronic signature, the investigator confirms that all recorded data have been verified as accurate.

If this study has been outsourced, the institutional policies of the supplier should be followed for development of data management plans. However, the supplier should ensure compliance with Good Pharmacoepidemiology Practice, and all applicable federal, state, and local laws, rules and regulations relating to the conduct of the study.

Figure 9A:
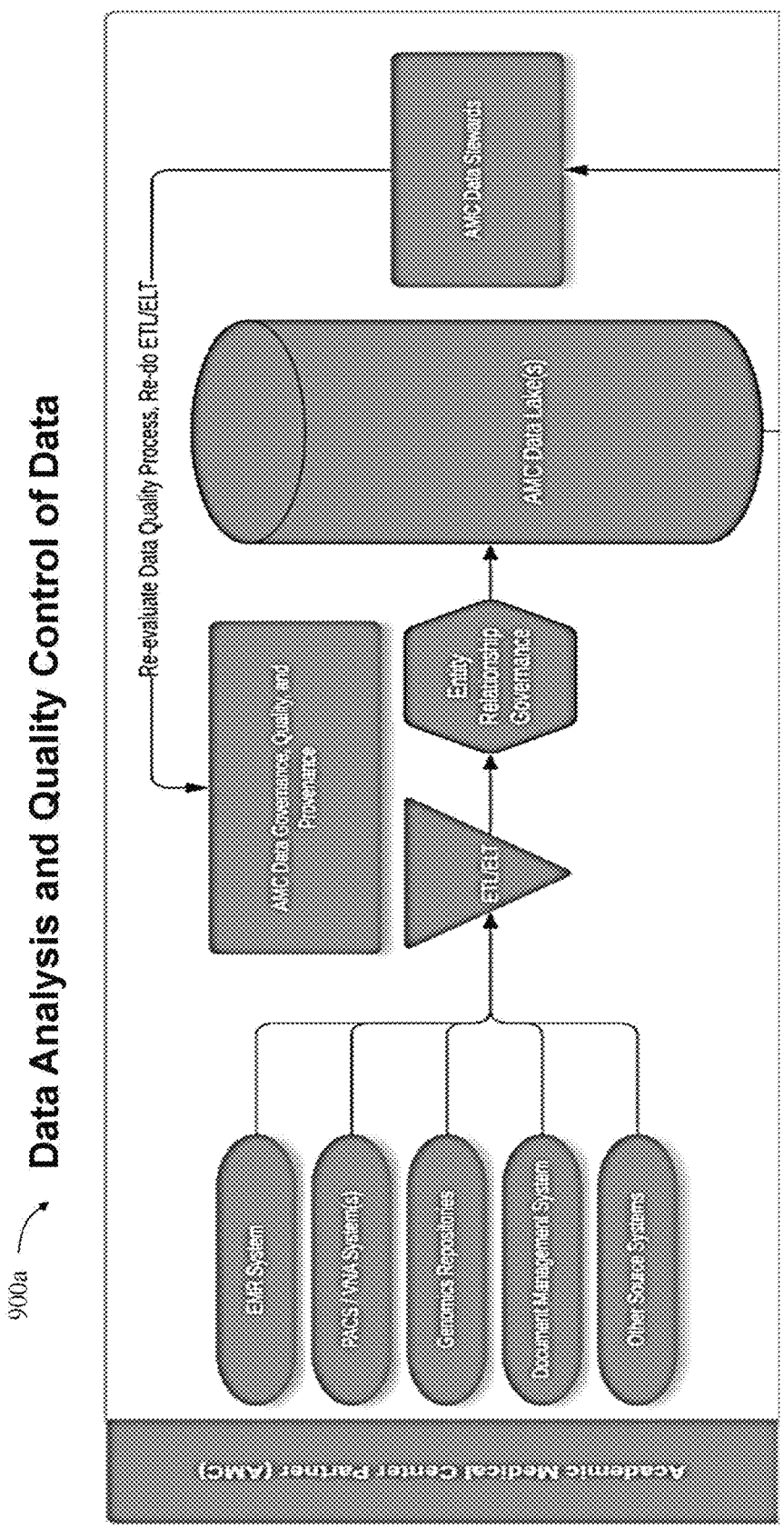
FIGS. 9A-C are exemplary embodiments of a schematic of data management, quality control and validation process.
Figure 9B:
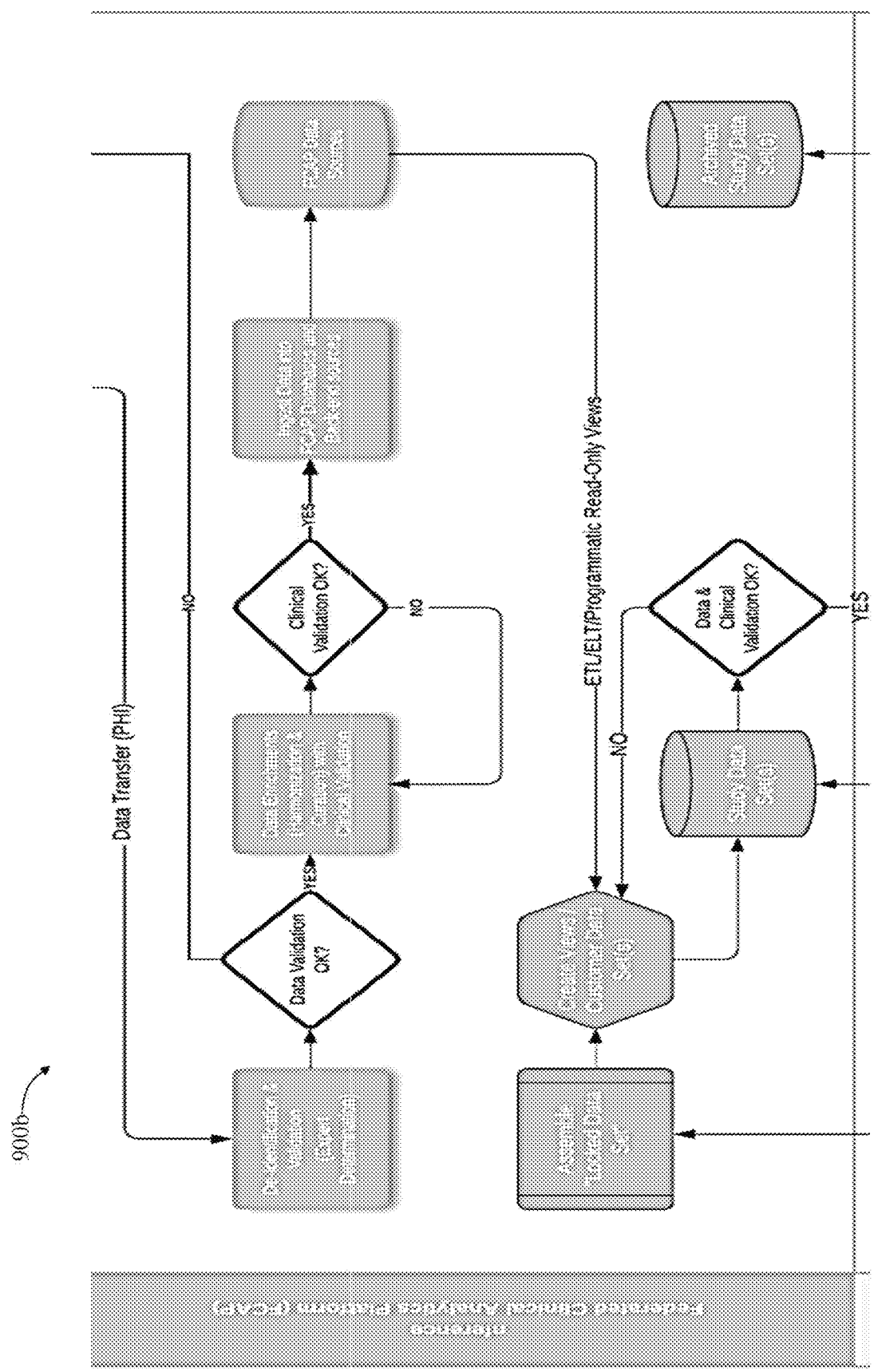
Figure 9C:
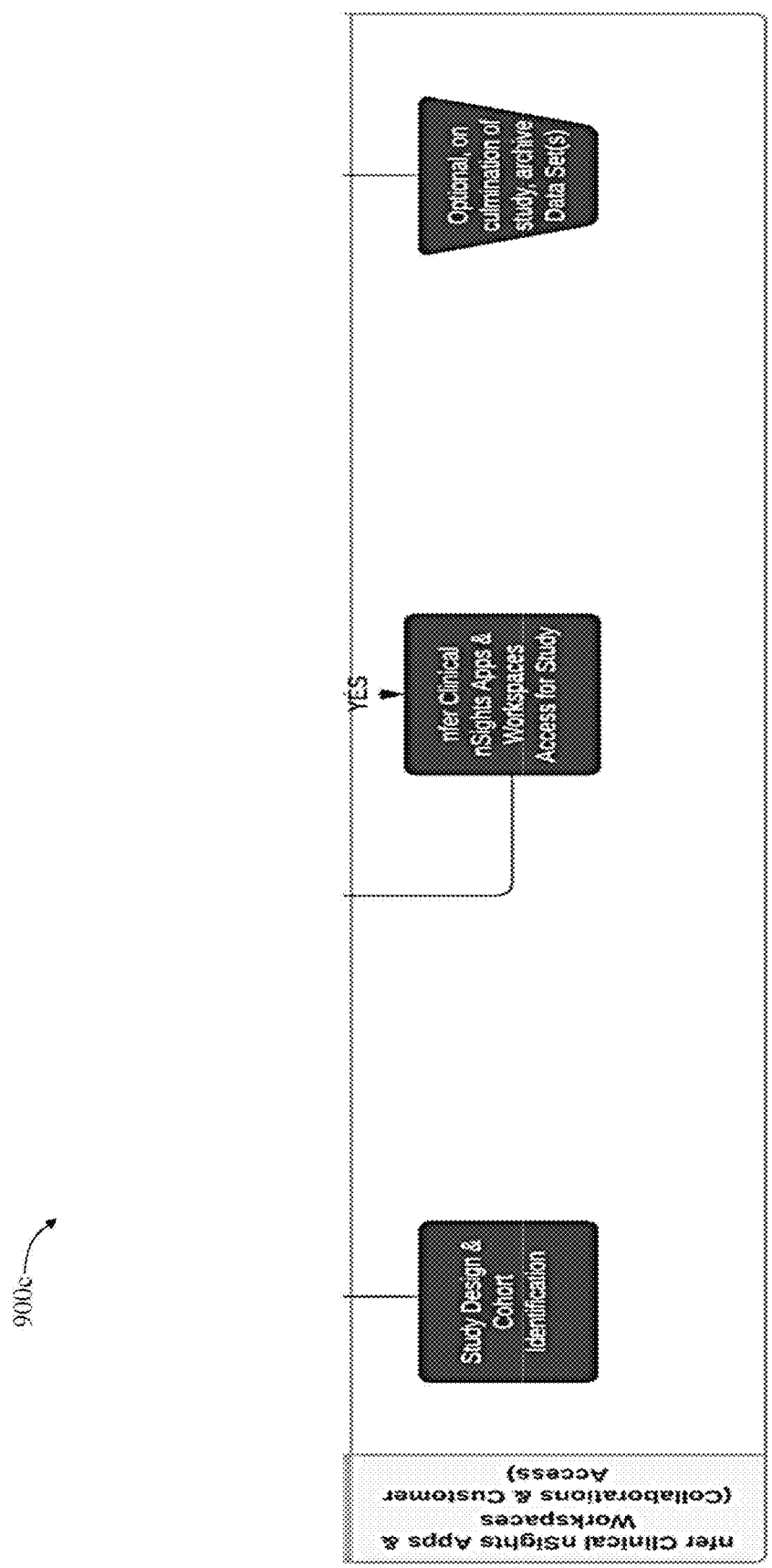

Data within the clinical platform may go through several transformations before it is made available to scientists and customers—the image above illustrates the high-level processes of data analysis and quality control of data, beginning with the Academic Medical Center (AMC) Partners, which is the source of all our data (FIGS. 9A-C, embodiments 900a-c). The platform may leverage the Data Governance frameworks of our AMC Partners to ensure that the quality and provenance of source data is validated for clinical and referential integrity prior to ingestion into the Federated Clinical Analytics Platform (FCAP). Upon ingestion into the FCAP, a team of experts may perform several functions, including de-identification of structured and unstructured data. The de-identification process may be a rigorous, expert determination-based process (details outlined further below), and this process may also involve validation of referential integrity within the data (beyond that of the source AMC's Data Governance process—this is because the platform performs cross-modality linking of clinical data from multiple sources, so cross-table and cross-database referential integrity validation may be a key component). In the event data quality/validation issues are encountered, the platform may reconvene with the Data Stewards of the AMC, so that they can address these issues upstream, and re-process the data extraction and delivery to the FCAP.

Following de-identification, data may undergo several enrichments within the FCAP, namely harmonization and augmented curation (details outlined below), and each of these steps may require rigorous data validation—both from a clinical perspective as well as from a data integrity perspective. The data validation steps during the enrichment phases may be in-line and occur in parallel with the enrichment processes.

Once the enriched data is validated, it may be made available by various means for downstream analytics and data science consumption—specifically, the FCAP may provide access to this data via certain applications and workspaces.

For end-users (data scientists, clinical scientists, etc.) working with the data using certain applications and workspaces, the Schema Visualizer application may provide detailed schema information of the transformed data, including entity relationships as well as provenance and transformation related transparencies, so the user can be sure of the treatment of each individual data element. Details of variable composition, model performance and validation, and more may be made available and displayed for end users. Through this, users may also have the tools and information to be able to determine whether the variables are suited for their use. Additionally, release notes may be made available within the product itself for all users with access as part of the product homepage.

These processes and the included data quality checks are outlined in detail below.

3.8.1 De-identification

The platform may use a "hiding-in-plain-sight" expert-certified de-identification process. Our approach has been published in a peer-reviewed publication. From a performance standpoint, our approach may outperform existing tools, with a recall of 0.992 and precision of 0.979 on the i2b2 2014 dataset and a recall of 0.994 and precision of 0.967 on a dataset of 10,000 notes from the Mayo Clinic.

As previously mentioned, one aspect of the de-identification process may be to ensure referential integrity within and across multiple data sources, such as:

Correct patient data mapping (data associated with ID is data associated with hashID)

Consistency of data substitutions and transformations

General data field mapping (e.g. are flowsheets going to corresponding flowsheets)

Specific data field mapping (e.g. are patient ID flowsheets going to patient hashID flowsheets)

3.8.2 Harmonization

Harmonization is the process of transforming structured and semi-structured data into unified concepts or variables to enable efficient and comprehensive downstream analysis.

This may include:

Automated aggregation of similar concepts based on data characteristics suggested for review (e.g. the shape of the distribution of a set of measurements being similar)

Mapping of equivalent terms, equivalent 'entities' (e.g. lab tests, medications) to a parsimonious dictionary ("deduplication")

Elimination of data elements (terms, values, entities) that are invalid (e.g. physiologically implausible) based on clinical review Creation and maintenance of a relational structure among all data elements in the refined dictionary Harmonization of structured quantitative data (e.g. lab tests) involves technology and software-enabled transformation of data variables, which then may undergo final review and approval by clinical scientists. Any applied transformations may be recorded through the software to track the origins of data and the composition of the final harmonized variables.

Harmonization of structured categorical variables (ex. medications administered, ICD diagnoses) may utilize pipelines that rely on a combination of knowledge graph and logic provided by clinical scientists.

Data harmonization may be an ongoing process. If a variable has been missed, misclassified, or mistransformed, it may be reviewed and updated by our clinical science team. Once validated, the updates are part of a versioned update which is synchronously across setups. The process of harmonization is anchored in four guiding principles. To enable accountability for this dataset processing and earn trust from downstream data users, harmonization may be: Consistent, Clinically informed, Transparent, and/or Well-documented.

To attain consistency, we have developed a standardized pipeline through which each patient metric is processed from its many raw forms into a single shared encoding. To ensure that within this pipeline each decision is made in a clinically informed manner, our harmonization is conducted exclusively by clinically trained individuals (either a medical student or a medical professional). To accomplish transparency in harmonization, the handling of each metric within our pipeline is documented and available to all data users. This documentation reveals all raw data forms that were gathered and unified, as well as all instances where values were converted from one unit of measure to another. Annotations are authored by our curators when complex data handling arises (e.g. when outright mislabeling is discovered in the raw data).

Data that does not undergo harmonization is exposed in unharmonized form as it stands following the de-identification process.

3.8.3 Augmented Curation

Augmented curation is the process of developing and deploying language-based models to extract sentiment from unstructured text. These models may allow us to transform unstructured data into structured form through extraction of key sentiments and relationships from free text at scale. This may allow downstream users to identify and select patients based on information contained in written text of patients' records in an automated way.

Models may fall into two categories—Base (disease-agnostic, should apply to all patients) or Disease/Therapeutic Area-Specific (would apply to only a subset of patients).

Curation models may leverage Bidirectional Encoder Representations from Transformers (BERT)-based neural networks. BERT models were developed by Google as a pre-trained language model. For the model to perform a specific classification of interest well, we may need to fine-tune this base model using labeled datasets. These datasets may consist of fragments from clinical text with the concepts of interest highlighted.

Datasets are labeled by three independent clinical scientists. Datasets are used either for training or for testing of the model (the same dataset is never used for both). Scientists are provided with a tagging guide including examples and must pass a certification dataset to ensure they understand the model objectives and label definitions before they are certified to label datasets for a new model, ensuring some level of standardized understanding.

Dataset generation strategy may include ensuring diverse representation of concepts relevant to the model (ex. diseases from different therapeutic areas) and sentence structures. Vector embeddings of text fragments that meet the criteria required for the model may be generated and clustered, and datasets may be sampled and created from this sentence universe to generate, train, test and validation datasets which are representative of the diversity of text within the entirety of the clinical notes, where the models may ultimately be deployed. Models may be iteratively trained and tested as the datasets are labeled. Active learning methods may be utilized to sample from the sentence universe and iteratively address failure modes of the model.

Once models reach the desired sentence-level performance (typically at least 0.9 precision and recall on test and validation datasets), they may be deployed across all clinical text for the relevant patient population (all patients for base models). The relevant sentences may be identified using the platform's entity extraction service. For example, for the disease diagnosis model, we may first identify all mentions of diseases in notes, select those sentences, and pass each sentence to the model to get a classification of diagnosis versus not. Note, this may be a computationally intensive and time-intensive process to run. The knowledge graph, built on a combination of public ontologies and models, powers the identification of those concepts in the clinical text.

Once deployed, model performance may be continuously monitored. Users can submit error reports to the team responsible for owning the model. Systematic errors in model performance that are identified may be addressed using active learning to select sentences like those which are causing the error, which may then be tagged and then incorporated into model training and testing. Model evaluation and training may be iterative. Full model may run with all available models that take place every quarter and are part of versioned data releases. This may include "first-time" models which have met performance requirements, as well as improved versions of existing or previously deployed models. All models may be included in each quarterly run. If technical errors are identified in model deployment, a versioned patch release may be made.

3.8.4 Study Set Validation

When datasets are created for a defined cohort of interest for a study, there may be additional data quality checks applied. This may include dataset-specific validation of curation models. This may be supported by generating additional labeled datasets for a sampled subset from the dataset. Patient-level validation may also be performed through individual chart review of a sample of patients from each dataset. By default, once study design is completed, the dataset for the study cohort is frozen. Upon request and if appropriate for the study, new records can be released to the dataset based on recent updates. The net new data may go through the same validation and quality check processes described above prior to release.

Once the study was conducted, an independent scientist who was not involved in running the initial study may perform a code review of all the components that were used in the study. This may serve as a secondary validation of the approach and methods used in the study and ensure a level of reproducibility by a second independent scientist. If the study necessitates it, additional reviews can be put in place as requested.

As discussed above, the database used within the platform may contain only de-identified patient information (i.e., does not include names, addresses, social security or medical record numbers or other obvious identifiers), and may be fully compliant with the HIPAA. Therefore, no ethics review was necessary. Confidentiality of patient records was maintained at all times. All study reports contained aggregate data only and did not identify individual patients. At no time during the study did the sponsor receive patient identifying information.

3.9 Changes in the Conduct of the Study

There were no changes in the conduct of the study due to the COVID-19 pandemic.

4. STATISTICAL AND ANALYTICAL METHODS

There were no changes in the planned analyses of the study due to the COVID19 pandemic.

4.1 Characterize Patient Cohorts

All features were extracted from structured and unstructured data sources.

Descriptive analyses were performed to evaluate patient characteristics in the PH-COPD, COPD-only and screening cohorts. The aggregate number N (%) of patients within four 3-month bins to capture the presence of the following features in each time window may be presented:

Demographics
Lab tests and other observations
Medication history
Comorbidities
ECG findings
Echo findings
Imaging findings Means, SD, median and IQR was reported for continuous variables, and frequencies and percentages may be reported for categorical variables.

Figure 10:
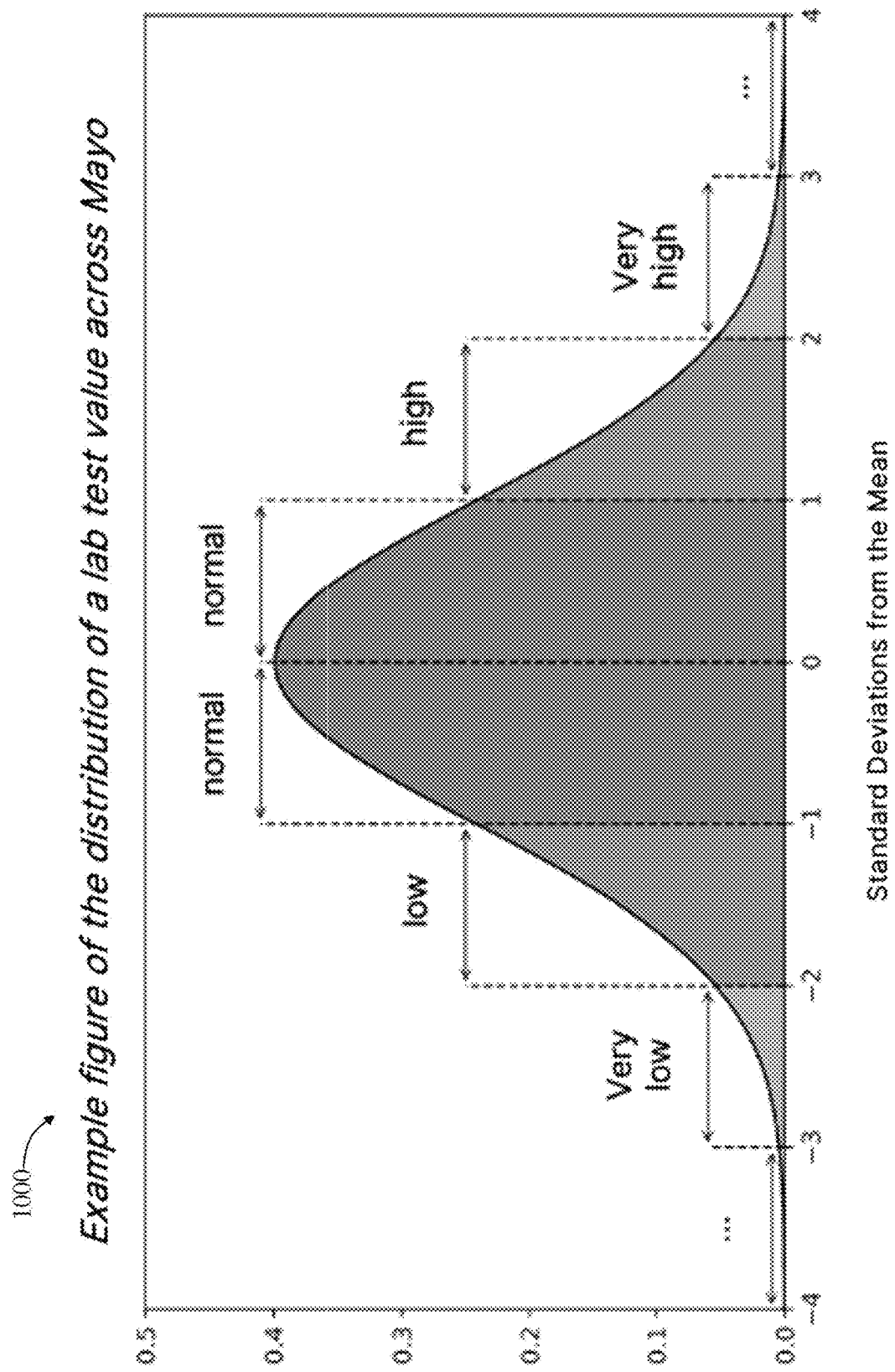
FIG. 10 is an exemplary embodiment of a categorization of lab tests based on a standard normal distribution across all Mayo patients.

To categorize whether a PH-COPD or COPD patient's lab test was abnormal relative to the matched controls, they may be individually compared to standard distributions generated from the entire Mayo Clinic population. Standard normal distributions may be plotted for each lab test based on the entire Mayo Clinic population using the mean of the lab test values for the 26 different lab tests. If a patient had more than 1 occurrence for the same lab test, the mean of means may be utilized to calculate the population's overall lab test mean. From these unimodal plots, the standard deviations may be calculated. Lab values falling within ±1 STD of the normal distribution's mean may be considered in normal range, whereas ±2 STDs of the normal distribution's mean may categorize the lab value as high or low, respectively, ±3 STDs of the normal distribution's mean may categorize the lab value as very high or very low, respectively, and anything +/−4 STDs away from the mean may be considered 'other' (FIG. 10, embodiment 1000).

4.1.2 Univariate Analysis and Logistic Regression

Univariate analysis may be an essential first step to understand the data and identify potential covariates that might be predictive or influential in the modeling process. All features and their associated values (means, STD, medians) may be compared in a one-off analysis to distinguish between the PH-COPD and COPD cohorts. Cohen's d, t-tests, chi-squared and odds ratios may be performed depending on the type of feature (continuous versus categorical). A multivariate logistic regression analysis may be used to examine the influencing factors between these two cohorts.

4.2 Train a Preliminary PH Detection Algorithm

Figure 11:
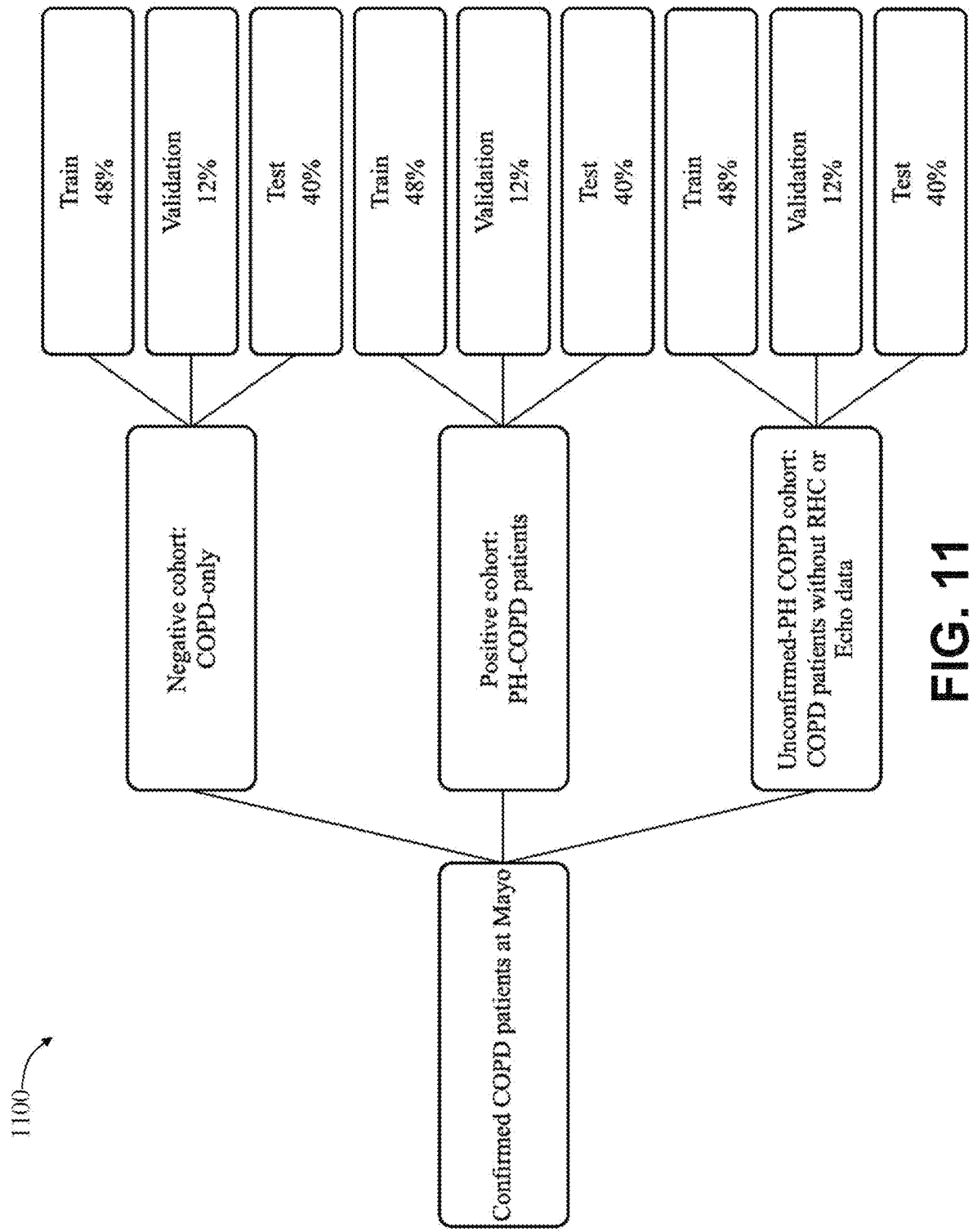
FIG. 11 is an exemplary embodiment of a schematic of PH-COPD, COPD-only and screening COPD cohorts.

Three types of PH detection algorithms may be trained on feature vectors comprised of the covariates listed in Section 3.6 (taken from EHR/ECG data from date of diagnosis to 3 months afterwards) for three sub-cohorts defined by "PH-COPD", "COPD-only" and "Screening/unconfirmed PH": ECG-only, EHR-only and ECG plus EHR. These three cohorts may then be then split into training, validation, and testing groups (FIG. 11, embodiment 1100).

The training/validation/test split is a technique to evaluate the performance of the machine learning model since you cannot evaluate the predictive performance of a model with the same data used for training. Therefore, randomly splitting the data may be a commonly used method for unbiased evaluation at a relative proportion of 48%/12%/40%. The training set may consist of the set of patients and relevant data used for training the model. The validation set may contain the group of patients used to provide an unbiased evaluation of the model fitted on the training dataset while model hyperparameters are tuned. Lastly, the testing dataset may include the unique set of patients used to provide an unbiased evaluation of the final model that was fitted on the training dataset. This may ensure that all three sets are representative of the entire dataset and provides a good way to measure the accuracy of the model.

The feature space may be normalized by patient-level data, such as visit frequency within the time window, i.e. per patient per month. For the EHR-based algorithms, both supervised (hypothesis driven) and contrastive self-supervised (hypothesis-free) approaches may be used.

Logistic regression:
Pros:
Interpretability
Makes no assumptions about distributions of classes in feature space
Insensitive to missing values
Cons:
Cannot accommodate non-numerical values (requires feature scaling or
transformation)
Sensitive to outliers
Can overfit in high-dimensional datasets
Convolutional neural network (CNN):
Pros:
CNNs do not require human supervision for the task of identifying important features.
They are very accurate at image recognition and classification.

Weight sharing is another major advantage.

CNNs minimize computation in comparison with a regular neural network.

They make use of the same knowledge across all image locations.

Cons:

A lot of training data is needed for the CNN to be effective.

Tend to be much slower because of operations like maxpool

Computationally expensive

Non-expressive learning and logics

Prone to overfitting because they tend to be deployed on massive features.

Supervised (hypothesis-driven): Uses labeled data with randomized weights to build a function that classifies the output. For example, An ECG for Patient A who has PH COPD versus EHR data for Patient B who is in the COPD only Cohort. An artificial neural network (ANN) is made up of layers of nodes. Each node has a set of weights and a threshold. The input data is transformed by the weights using a mathematical function. If the resulting value exceeds the threshold, the transformed value is passed to the next layer. A feedback loop is employed to improve performance over successive iterations, refining the weights and thresholds. Supervised models require a good amount of training data. The supervised approach incorporates the full data dictionary including lab values, observations, and augmented curation-derived diagnoses.

Contrastive self-supervised (hypothesis-free): Contrastive self-supervised learning takes two sets of labeled inputs. The first step is to train a model to transform those inputs into numerical vectors and minimize the distance between those vectors for inputs with the same label. The resulting vector is called an "embedding". Once an optimal embedding is determined, it can be used as an input to a supervised model. Additionally, while a supervised network is normally initiated with random weights, this model can be initialized with weights learned during the self-supervised learning and fine-tuned to the new task. This type of model is also benefited by limited training data.

The platform has previously developed a self-supervised embedding for ECG and EHR data using 9M ECGs from 2.4M patients at Mayo Clinic. The EHR vector is the sequence of a patient's ICD codes, medications, and procedures. This "vocabulary" is made up of 28,593 possible features. The embedding clusters patients with similar EHR journeys and ECG signatures closer together. The embedding can be applied separately to ECG and EHR data. Thus, we used this embedding for all 3 model variations. By using this process, it is as if the ECG embeddings contain info about the EHR journey, and vice versa.

For generalizability to health systems beyond the Mayo Clinic, preference may be given to pre-existing, widely available structured features (such as diagnosis codes) and those with high coverage for the patients/windows used (>15%).

In cases where data had missing values, there may be two potential approaches: The associated data type may be inputted as a null for that variable for the given patient. The value may be filled in with the median (for numerical) or mode (categorical) for the training set as a whole.

The approaches used may be determined by a combination of the feature's clinical relevance/importance to PH-COPD and the percentage of missing values for that feature.

Model performance may be assessed on a unique holdout set of patients to determine generalizability.

4.2.1 Statistical Measures of ML Model Validation

A true positive (TP) is where the model correctly predicts the patient as having PH. Similarly, a true negative (TN) is an outcome where the model correctly predicts that the patient does not have PH. A false positive (FP) is where the model incorrectly predicts the patient as having PH. And a false negative (FN) is where the model incorrectly assigns a true PH patient as being a control patient.

The recall, also termed the true positive rate (TPR) or sensitivity, is the ratio: TP/(TP+FN). Thus, sensitivity assesses the ability of the classifier to find all the positive patients—a highly sensitive test indicates there are few false negative results, and most disease patients are identified correctly. The specificity of a test: TN/(FP+TN) is its ability to appropriately designate an individual who does not have a disease as negative. The false positive rate (FPR)=FP/(FP+TN) and is a measure of accuracy for the diagnostic model, meaning the probability of falsely rejecting the null hypothesis.

The area under the curve (AUC) may provide an aggregate measure of performance across all possible classification thresholds. One way of interpreting AUC may be to interpret it as the probability that the model ranks a random positive example more highly than a random negative example. 100% prediction accuracy has an AUC of 1.0.

The Diagnostic Odds Ratio (DOR) may be calculated according to the formula: (TP/FN)/(FP/TN). DOR may depend significantly on the sensitivity and specificity of a test. A test with high specificity and sensitivity with low rate of false positives and false negatives may have high a DOR.

Positive predictive value (PPV), also known as precision, refers to the probability that a patient who tests positive for pulmonary hypertension has the condition, i.e. it measures the proportion of true positives among all the patients who tested positive and is calculated as TP (TP+FP). Negative predictive value (NPV) indicates the probability that a patient who tests negative for pulmonary hypertension is a true control. It measures the proportion of true negatives among all the patients who tested negative and is calculated as: TN (TN+FN).

Youden's J=TPR−FPR finds the optimal threshold using the best TPR with a low FPR.

4.2.2 Attention Mapping

Supervised and self-supervised ensemble transformer EHR models may be limited in their interpretability. Attention mapping may allow for identification of these salient features by using an axiomatic model interpretability algorithm to assign importance scores to each input feature by approximating the integral of gradients of the model's output with respect to the inputs along the path from given baselines or references to inputs.

4.3 Estimate Prevalence of PH-COPD Among Patients with COPD Across the Best Performing Models Prevalence estimation may be based on the results from the three best performing models (ECG-only, EHR+ECG, EHR-only). To estimate the prevalence of PH in a COPD population, we divided the patients identified as PH-COPD in the screening cohort based on each model's output plus the 3012 known PH positive patients, divided by either the number of patients that have a COPD diagnosis between 2015-2019, do not have a PH diagnosis prior to COPD diagnosis, and have an ECG on or after COPD index within the study window (n=53327) or the number of patients that have a COPD diagnosis between 2015-2019 but do not have a PH diagnosis prior to COPD index (n=76,818). These predicted prevalence estimations may then be adjusted using the models' sensitivity (%) to get a resultant sensitivity-corrected prevalence.

5. RESULTS

5.1 Construction of Study Sample

Of 99,970 adults with COPD between 2015-2019 at Mayo Clinic, 3,012 PH-COPD patients were found with 1) mean pulmonary arterial pressure (mPAP)>20 mmHg on RHC or tricuspid regurgitation velocity (TRV)>3.4 m/s via echocardiogram, 2) COPD diagnosis before or ≤3 months after PH diagnosis, and 3) no Group 1, 2, or 4 PH. A COPD-only cohort of 6,127 patients without PH was identified with mPAP≤20 mmHg on all RHCs and no TRV>3.4 m/s, or if no RHC, all TRV≤2.8 m/s. A screening cohort of 31,362 patients had COPD but with no rule-out or confirmatory RHC or echo (Table 1).

TABLE 1

Patient counts of PH-COPD, COPD-only and screening cohorts

| Cohort | Patient Counts 2015-2019 |
|---|---|
| PH-COPD | 3012 |
| COPD-only | 6127 |
| Screening | 31362 |

5.2 Main Results

5.2.2 Univariate Analysis and Logistic Regression

5.2.2.1 Univariate Analysis

A univariate analysis was performed comparing continuous and categorical features between PH-COPD patients to COPD patients (Tables 3,4). Cohorts were similar with respect to race and sex and only small differences were observed between symptoms. The largest differences were found for laboratory tests: NT-proBNP (PH-COPD vs COPD-only mean: 5520.29 vs 2345.51 pg/mL), creatinine (1.43 vs 1.12 mg/dL), hemoglobin (11.8 vs 12.75 g/dL), erythrocyte distribution width (15.38 vs 14.452%); and Echo/ECG measurements: LV mass (221.13 vs 181.25), LV mass index (112.58 vs 95.23 g/m$^2$), LA volume (85.38 vs 65.96 mL), RVSP (45.99 vs 31.62 mmHg), RA volume (73.65 vs 51.42 mL), RA volume index (37.71 vs 27.53 mL/m$^2$), and QRS duration (109.06 vs 97.55 ms), with all $p<0.001$. These findings indicate PH-COPD patients have distinct clinical profiles and further understanding of this group will help clinicians identify patients who may benefit from PH-COPD screening.

TABLE 3

Univariate analysis of continuous variables between PH-COPD and COPD-only patients

| | PH-COPD | | COPD-only | | Comparison metrics[1] | | | |
|---|---|---|---|---|---|---|---|---|
| | | | | | cohen's | | p-value | p-value |
| | mean | std | mean | std | d | t-test | (t-test) | (u-test) |
| Demographics | | | | | | | | |
| Age at COPD diagnosis | 71.7 | 11.11 | 67.12 | 12.52 | 0.3868 | 17.7465 | 0 | 0 |
| Time from first record to COPD diagnosis (months) | 210.18 | 143.2 | 193.97 | 145.83 | 0.1122 | 5.0561 | 0 | 0 |
| Time from COPD diagnosis to last record at Mayo (months) | 96.08 | 65.24 | 75.31 | 53.61 | 0.3478 | 15.1357 | 0 | 0 |
| Observations | | | | | | | | |
| Heart rate (range: 2.5-97.5 percentile) | 80.2 | 14.49 | 80.39 | 14.7 | −0.0129 | −0.4643 | 0.6425 | 0.8221 |
| Height (range: 2.5-97.5 percentile) | 1.68 | 0.08 | 1.68 | 0.08 | −0.0031 | −0.1191 | 0.9052 | 0.9343 |
| Weight (range: 2.5-97.5 percentile) | 84.15 | 23.02 | 82.41 | 21.65 | 0.0779 | 3.1644 | 0.0016 | 0.0063 |
| BMI (range: 5.0-95.0 percentile) | 26.4 | 7.5 | 26.22 | 6.97 | 0.0255 | 0.9956 | 0.3195 | 0.0535 |
| Systolic blood pressure (range: 2.5-97.5 percentile) | 129.5 | 17.1 | 127.03 | 16.38 | 0.1473 | 3.9795 | 0.0001 | 0.0002 |
| Diastolic blood pressure (range: 2.5-97.5 percentile) | 68.73 | 8.89 | 72.55 | 9.05 | −0.4264 | −11.6341 | 0 | 0 |
| Healthcare resource utilization | | | | | | | | |
| Days hospitalized | 4.03 | 7.83 | 1.57 | 4.37 | 0.3875 | 16.0375 | 0 | 0 |
| Emergency department visits | 1.22 | 1.99 | 0.65 | 1.35 | 0.3315 | 14.038 | 0 | 0 |
| Visits to Mayo | 9.39 | 11.84 | 5.27 | 7.83 | 0.4103 | 17.3193 | 0 | 0 |
| Other procedures/tests | | | | | | | | |
| CT scan: lung/chest CT scan, cardiac CT | 0.58 | 0.94 | 0.4 | 0.77 | 0.2073 | 9.0134 | 0 | 0 |
| X-ray: lung/chest x-ray | 2.31 | 3.12 | 1.1 | 1.86 | 0.4696 | 19.569 | 0 | 0 |
| Oxygen use | 1.85 | 3.73 | 0.8 | 2.51 | 0.3293 | 13.9334 | 0 | 0 |
| Laboratory tests: | | | | | | | | |
| NT-proBNP- N-terminal pro b-type natriuretic peptide (range: 2.5-97.5 percentile) | 5520.29 | 7699.51 | 2345.51 | 5208.64 | 0.483 | 13.6064 | 0 | 0 |
| Creatinine (range: 2.5-97.5 percentile) | 1.43 | 1.15 | 1.12 | 0.9 | 0.3056 | 12.0559 | 0 | 0 |
| Hemoglobin (range: 2.5-97.5 percentile) | 11.8 | 2.13 | 12.75 | 2.02 | −0.4558 | −18.331 | 0 | 0 |

TABLE 3-continued

Univariate analysis of continuous variables between PH-COPD and COPD-only patients

|  | PH-COPD | | COPD-only | | Comparison metrics[1] | | | |
|---|---|---|---|---|---|---|---|---|
|  | mean | std | mean | std | cohen's d | t-test | p-value (t-test) | p-value (u-test) |
| Hematocrit (range: 2.5-97.5 percentile) | 36.58 | 6.22 | 38.63 | 5.75 | −0.3428 | −13.6829 | 0 | 0 |
| Sodium (range: 2.5-97.5 percentile) | 139.13 | 3.86 | 139.49 | 3.6 | −0.0951 | −3.7999 | 0.0001 | 0.0001 |
| Red blood cell width distribution (range: 2.5-97.5 percentile) | 15.38 | 1.96 | 14.45 | 1.9 | 0.4799 | 19.2563 | 0 | 0 |
| Medication history[2] | | | | | | | | |
| Diuretics [furosemide (Lasix), bumetanide (Bumex), and spironolactone (Aldactone)] | 3.6 | 6.61 | 1.03 | 3.09 | 0.4979 | 20.2705 | 0 | 0 |
| Inhaled Corticosteroids | 2.26 | 5.57 | 1.13 | 3.64 | 0.2409 | 10.1533 | 0 | 0 |
| Bronchodilators | 3.88 | 6.9 | 1.83 | 4.17 | 0.3605 | 15.0481 | 0 | 0 |
| COPD medications [Phosphodiesterase-5 inhibitors, Theophylline, and oral steroids] | 2.87 | 6.17 | 1.69 | 4.3 | 0.2213 | 9.4026 | 0 | 0 |
| Echo (as available)[3] | | | | | | | | |
| SV- stroke volume (derived, include method of acquisition) | 73.52 | 21.75 | 69.54 | 21.03 | 0.1858 | 2.8702 | 0.0042 | 0.0022 |
| SV index (stroke volume index) | 40.04 | 11.09 | 39.55 | 9.87 | 0.0468 | 0.7058 | 0.4805 | 0.7088 |
| LVEF- left ventricular ejection fraction | 53.7 | 13.16 | 54.4 | 11.96 | −0.0558 | −0.8629 | 0.3884 | 0.5313 |
| LV (left ventricular) mass | 221.13 | 78.1 | 181.25 | 66.55 | 0.5496 | 8.673 | 0 | 0 |
| LV (left ventricular) mass index | 112.58 | 36.32 | 95.23 | 29.99 | 0.5207 | 8.2411 | 0 | 0 |
| LA (left atrium) volume | 85.38 | 37.09 | 65.96 | 33.69 | 0.5484 | 8.172 | 0 | 0 |
| LA (left atrium) volume index | 44.24 | 19.87 | 35.07 | 16.01 | 0.5083 | 7.6386 | 0 | 0 |
| LVEDV- left ventricular end-diastolic volume lvedv | 131.01 | 59.85 | 113.07 | 48.26 | 0.3301 | 4.2267 | 0 | 0.0001 |
| RVSP- right ventricular systolic pressure rvsp | 45.99 | 8.93 | 31.62 | 6.68 | 1.8217 | 16.6617 | 0 | 0 |
| RV/LV ratio - right ventricular to left ventricular diameter ratio rvlv_ratio | 44.3 | 10.67 | 43.83 | 9.61 | 0.0462 | 0.4162 | 0.6775 | 0.8215 |
| ra_vol | 73.65 | 43.39 | 51.42 | 29.49 | 0.5993 | 4.0051 | 0.0001 | 0.0002 |
| ra_vol_index | 37.71 | 20.74 | 27.53 | 14.97 | 0.5624 | 3.7199 | 0.0003 | 0.0004 |
| ECG (as available): | | | | | | | | |
| QT interval | 405.78 | 51.05 | 395.88 | 44.86 | 0.2061 | 7.744 | 0 | 0 |
| QRS durations | 109.06 | 31.37 | 97.55 | 24.31 | 0.4102 | 15.1938 | 0 | 0 |

[1]values that are 0 are at least <0.00005
[2]Mean orders per patient
[3]Echocardiogram measurements used are from the non-diagnostic echocardiogram, if available

TABLE 4

Univariate analysis of categorical variables between PH-COPD and COPD-only patients

|  | odds ratio (OR)[1] | p-value (odds ratio)[1] | chi-sq[1] | p-value (chi-sq)[1] |
|---|---|---|---|---|
| Demographics | | | | |
| Race (White) | 0.93 | 0.4241 | 0.6 | 0.44 |
| Ethnicity (Not Hispanic or Latino) | 1.45 | 0.0005 | 11.35 | 0.0008 |
| Gender (Female) | 0.91 | 0.0385 | 4.2 | 0.0405 |
| Findings on imaging tests | | | | |
| Pulmonary artery enlargement/dilated pulmonary artery | 8.19 | 0 | 28.05 | 0 |
| cardiac chamber enlargement | 3.94 | 0 | 88.56 | 0 |
| right ventricular enlargement | 9.53 | 0 | 16.63 | 0 |
| chronic pulmonary embolism | 2.03 | 0.6027 | 0.04 | 0.8467 |
| mosaicism | 3.09 | 0 | 53.05 | 0 |
| centrilobular ground glass opacities | 0 | 1 | 0 | 1 |
| Interstitial lung disease/ILD | 3.08 | 0 | 39.21 | 0 |
| fibrosis/fibrotic tissue | 3.5 | 0 | 31.94 | 0 |
| honeycombing | 2.17 | 0.0017 | 9.8 | 0.0017 |
| traction bronchiectasis | 2.58 | 0 | 26.37 | 0 |
| combined pulmonary fibrosis and emphysema | 1.32 | 0 | 19.89 | 0 |

TABLE 4-continued

Univariate analysis of categorical variables between PH-COPD and COPD-only patients

|  | odds ratio (OR)[1] | p-value (odds ratio)[1] | chi-sq[1] | p-value (chi-sq)[1] |
|---|---|---|---|---|
| usual interstitial pneumonia (UIP) | 3.46 | 0.0004 | 12.89 | 0.0003 |
| hypersensitivity pneumonitis | 1.53 | 0.691 | 0.02 | 0.8766 |
| organizing pneumonia | 2.04 | 0.4521 | 0.42 | 0.5159 |
| interstitial pneumonia | 2.71 | 0.2283 | 0.92 | 0.3373 |
| non specific interstitial pneumonia | 10.19 | 0.0169 | 4.8 | 0.0284 |
| reticular opacities | 2.24 | 0 | 28.41 | 0 |
| linear opacities | 1.45 | 0.0206 | 5.2 | 0.0226 |
| Symptoms (by ICD or NLP) |  |  |  |  |
| Dyspnea | 1.88 | 0 | 197.03 | 0 |
| Chest pain | 1.06 | 0.3917 | 0.69 | 0.4059 |
| Edema of lower limbs | 2.38 | 0 | 143.49 | 0 |
| Fatigue | 1.14 | 0.0827 | 2.96 | 0.0853 |
| Dizziness | 1.16 | 0.0997 | 2.7 | 0.1004 |
| Fainting/Syncope | 1.14 | 0.1743 | 1.78 | 0.1823 |
| Heart palpitations | 1 | 0.9629 | 0 | 1 |
| Cyanosis | 8.16 | 0.0031 | 8.01 | 0.0047 |

[1]values that are 0 are at least <0.00005

5.2.2.2 Logistic Regression

Figure 12:
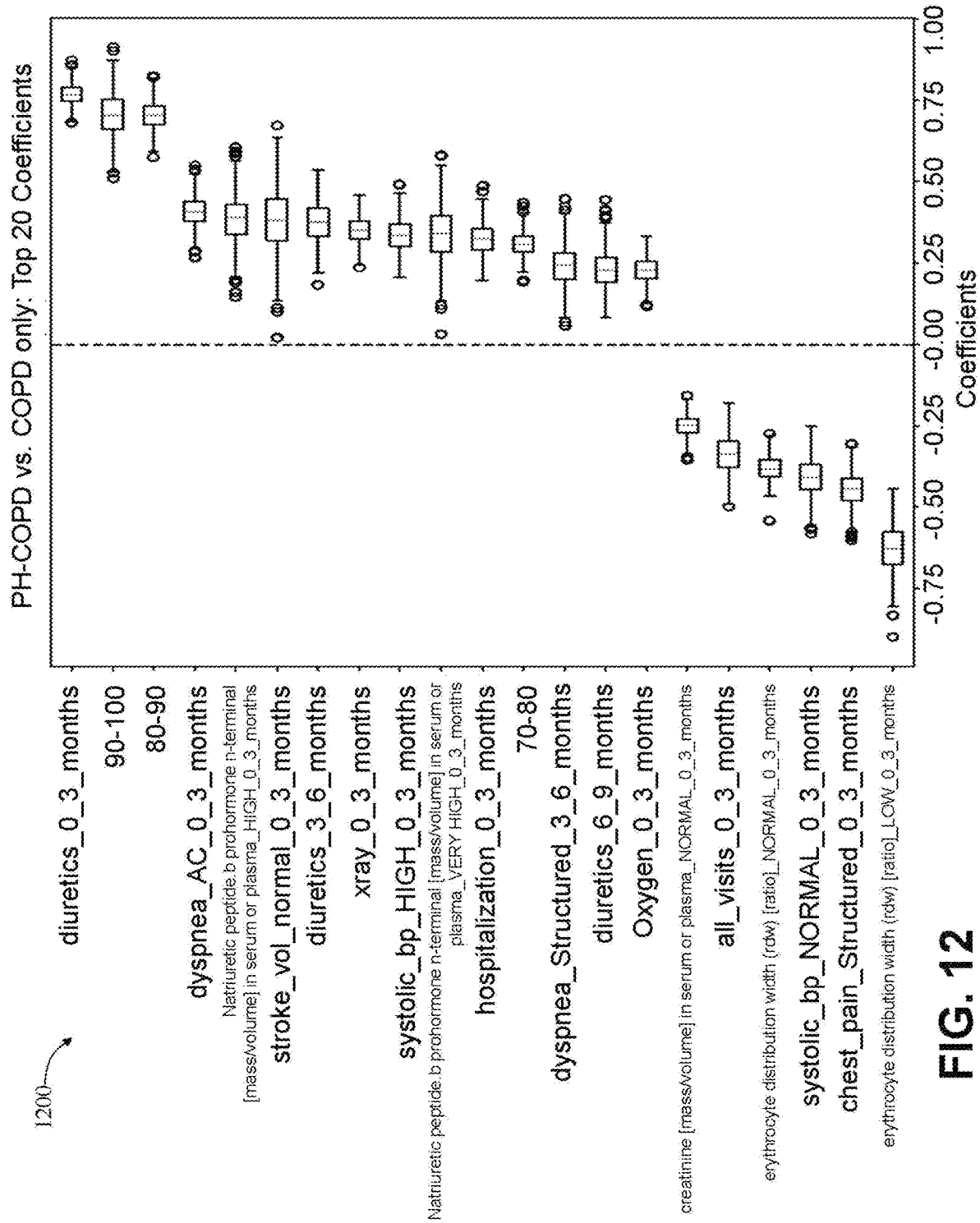
FIG. 12 is an exemplary embodiment of a result for multivariate logistic regression predicting PH-COPD versus COPD only.

Overall, the multivariate logistic regression showed an AUC of 0.76, suggesting relatively good discrimination ability. FIG. 12, embodiment 1200, highlights the top 20 coefficients identified through multivariate logistic regression analysis on all clinical variables listed in Tables 3 and 4. Coefficients that are greater than 0 predict PH-COPD while those less than 0 predict COPD only. Use of diuretics, comorbid dyspnea, high systolic blood pressure, elevated NT proBNP, oxygen dependence and increased hospitalization were all identified as variables predictive of PH-COPD. The coefficients marked as 'NR' were features that did not reach 50% agreement from panelists.

Worsening lung diffusion capacity from pulmonary function tests were not included for model building due to low coverage within the de-identified data source.

TABLE 5

Features with high physician agreement and significant model coefficients

|  | Physician Agreement (N = 8) | Model Coefficient [95% CI][a] |
|---|---|---|
| High O₂ requirement | 75% | 0.23[0.15, 0.3]* |
| Worsening lung diffusion capacity | 75% | NA[b] |
| High BNP/NT-proBNP | 75% | 0.39[0.24, 0.54] |
| Increased dyspnea on exertion | 50% | 0.41[0.32, 0.49] |
| Lower extremity edema | 50% | 0.14[0.05, 0.23] |
| Signs of right heart dysfunction | 50% | NA[b] |
| Diuretic use | NR | 0.77[0.69, 0.84] |
| Age (80-89y) | NR | 0.7[0.61,0.78] |
| Low erythrocyte distribution width | NR | −0.63[−0.76, −0.5] |
| Low hemoglobin | NR | 0.17[0.08, 0.25] |

NR = Not reported
[a]All p < 0.05; coefficients >0 predict PH-COPD, <0 COPD only
[b]Excluded from model: low coverage (<10% of PH-COPD patients)

5.2.3 PH Detection Algorithm Development
5.2.3.1 EHR Only, ECG Only and ECG+EHR Models Table 6 shows the performance metrics for the four different models (EHR only [supervised], EHR only [self-supervised], ECG only and ECG+EHR). All AUCs were greater than or equal to 0.79, indicating a high level of discriminative ability between COPD patients with and without PH.

At the optimal threshold (0.295), the ECG-only model showed the highest sensitivity and specificity of 80.2 (95% CI: 76.94-84.39) and 80.02 (95% CI: 77.79-82.08), respectively, demonstrating that 80% of the true negative cases were accurately identified by the model. The diagnostic odds ratio was calculated to quantify the effectiveness of the model as a diagnostic tool. The DOR for this model was 16.44 (95% CI: 13.49-21.11), indicating that the odds of the model correctly identifying PH in COPD patients were approximately 16 times higher than the odds of a false positive. The PPV of the model was 0.61 (95% CI: 0.58-0.64), which reflects that 61% of the patients predicted to have PH by the model have PH. The NPV was 0.91 (95% CI: 0.90-0.93), indicating that 91% of the patients predicted not to have PH by the model were COPD only.

For the EHR only (self-supervised), sensitivity and specificity values (95% CI) were 76.4 (74.53-78.12) and 76.2 (74.99-77.44), respectively. The DOR for this model was 10.4 (95% CI: 9.38-11.76), indicating that the odds of the model correctly identifying PH in COPD patients were approximately 10 times higher than the odds of a false positive. The PPV of the model was 0.63 (95% CI: 0.62-0.65), which reflects that 63% of the patients predicted to have PH by the model have PH. The NPV was 0.86 (95% CI: 0.85-0.87), indicating that 86% of the patients predicted not to have PH by the model were COPD only.

For the ECG+EHR (self-supervised) model, the model's sensitivity was 80.27 (95% CI: 76.58-83.83), meaning it correctly identified roughly 80% of the actual PH cases in COPD patients. The specificity was 80.24 (95% CI: 78.05-82.02), similarly indicating that 80% of the non-PH cases were accurately identified as such by the model. The Diagnostic Odds Ratio was 16.76 (95% CI: 13.35-20.94). This suggests that the odds of the model correctly identifying PH in COPD patients were almost 17 times higher than the odds of a false positive. The PPV of the model was 0.61(95% CI: 0.58-0.64), which means that 61% of patients predicted to have PH by the model were true positives. The NPV was 0.91 (95% CI: 0.9-0.93), indicating that 90% of patients predicted to be COPD-only were indeed negative cases.

TABLE 6

Performance metrics for the EHR-only, ECG-only and ECG + EHR algorithms

| Metric | EHR-only (supervised) | | EHR-only (self-supervised) | | ECG-only | | ECG + EHR | |
|---|---|---|---|---|---|---|---|---|
| | Mean | 95% CI | Mean | 95% CI | Mean | 95% CI | Mean | 95% CI |
| AUC | 0.79 | (0.78-0.81) | 0.84 | (0.83-0.86) | 0.87 | (0.85-0.90) | 0.87 | (0.85-0.90) |
| Sensitivity, % | 72.63 | (70.56-74.53) | 76.85 | (74.53-78.12) | 80.2 | (76.94-84.39) | 80.27 | (76.58-83.83) |
| Specificity, % | 72.2 | (70.77-73.75) | 76.62 | (75.62-77.98) | 80.02 | (77.79-82.08) | 80.24 | (78.05-82.02) |
| Diagnostic odds ratio | 6.91 | 6.23-7.92 | 10.91 | (9.66-12.20) | 16.44 | (13.49-21.11) | 16.76 | (13.35-20.94) |
| PPV | 0.58 | 0.57-0.60 | 0.61 | (0.60-0.63) | 0.61 | (0.58-0.64) | 0.61 | (0.58-0.64) |
| NPV | 0.83 | 0.82-0.84 | 0.87 | (0.86-0.88) | 0.91 | (0.90-0.93) | 0.91 | (0.90-0.93) |
| Threshold | 0.214 | | 0.332 | | 0.295 | | 0.29 | |

5.2.3.2 Attention Mapping

Attention mapping highlighted the key features that were integral in the EHR only (supervised and self-supervised) models' decision-making process and provided insights into the significant factors associated with PH in COPD patients (Tables 7,8). In the supervised EHR only model, which uses the full data dictionary including unstructured text, lab tests and observations, some of the highest scored features included symptoms such as dyspnea, dizziness, and chest pain. Lab tests like elevated NT pro-BNP, RDW and decreased hematocrit were also highly important variables. Similarly, observations like obesity and elevated diastolic blood pressure came up.

In the self-supervised approach, commonly presenting comorbid conditions were found as salient including ischemic heart disease, CKD, hypertension, atrial fibrillation, and bundle branch blocks which we know are associated with pulmonary hypertension. Several pulmonology related diseases are present as well including pleural effusion and structured diagnosis codes related to breathing difficulties. The use of diuretics is also highly weighted. ECG abnormalities are also present, underscoring the predictive capabilities of the ECG for a disease etiology only diagnosed traditionally by RHC and echo.

TABLE 7

Highest scored features using attention mapping from the supervised EHR only model

| Description | score |
|---|---|
| diuretics | 200.3756 |
| natriuretic peptide.b prohormone n-terminal [mass/volume] in serum or plasma_OTHER | 69.742 |
| creatinine [mass/volume] in serum or plasma_OTHER | 44.1736 |
| erythrocyte distribution width (rdw) [ratio]_OTHER | 27.5285 |
| dyspnea_AC | 27.1299 |
| natriuretic peptide.b prohormone n-terminal [mass/volume] in serum or plasma_HIGH | 16.8456 |
| all_visits | 16.6613 |
| weight_NORMAL | 15.3672 |
| natriuretic peptide.b prohormone n-terminal [mass/volume] in serum or plasma_VERY HIGH | 14.7214 |
| QRSDURATION_OTHER | 11.6172 |
| copd_meds | 11.0243 |
| Xray | 9.8158 |
| systolic bp_NORMAL | 9.2861 |
| height_NORMAL | 9.2683 |
| hemoglobin in whole blood_NORMAL | 8.029 |
| erythrocyte distribution width (rdw) [ratio]_HIGH | 7.8693 |
| diastolic bp_NORMAL | 7.6605 |
| sodium-serum/plasma-substance concentration-point in time --_NORMAL | 7.2112 |

TABLE 7-continued

Highest scored features using attention mapping from the supervised EHR only model

| Description | score |
|---|---|
| erythrocyte distribution width (rdw) [ratio]_VERY HIGH | 7.1204 |
| hematocrit [volume fraction] of blood by automated count_OTHER | 7.0575 |
| hemoglobin in whole blood_VERY LOW | 7.0416 |
| erythrocyte distribution width (rdw) [ratio]_NORMAL | 6.8226 |
| Q_TINTERVAL_OTHER | 6.5147 |
| body mass index (bmi)_NORMAL | 6.1467 |

TABLE 8

Highest scored features using attention mapping from the self-supervised EHR only model

| Description | score |
|---|---|
| heart failure | 1924.3655 |
| other chronic obstructive pulmonary disease | 1409.8629 |
| atrial fibrillation and flutter | 1345.7885 |
| other pulmonary heart diseases | 1005.8395 |
| complications and ill-defined descriptions of heart disease | 782.8515 |
| atrioventricular and left bundle-branch block | 619.5464 |
| chronic kidney disease (ckd) | 522.976 |
| multiple valve diseases | 491.7289 |
| abnormal results of function studies | 467.7729 |
| electrocardiogram, routine ecg with at least 12 leads; inter | 436.2526 |
| cardiac implantable device nos | 392.5449 |
| chronic ischemic heart disease | 369.466 |
| nonrheumatic mitral valve disorders | 353.1338 |
| cardiac arrest | 344.8259 |
| other interstitial pulmonary diseases | 310.9096 |
| other conduction disorders | 294.7985 |
| cardiomyopathy | 292.8915 |
| rheumatic tricuspid valve diseases | 267.7692 |
| effusion pleural | 264.786 |
| electrocardiogram, routine ecg with at least 12 leads; traci | 262.8833 |
| abnormalities of breathing | 255.3534 |
| ecg routine ecg w/least 12 lds w/i&r | 222.4414 |
| natriuretic peptide | 220.98 |
| Furosemide | 205.8051 |
| essential (primary) hypertension | 205.4059 |

5.2.4 Estimate Prevalence of PH-COPD Among Patients with COPD Across a Variety of Clinical Settings Based on the three best performing models, the sensitivity-corrected prevalence of PH in COPD populations were as follows: 6.870, 5.920 and 6.77, respectively (Table 9).

This adjustment indicates a lower prevalence compared to the raw estimates, reflecting the importance of accounting for diagnostic test characteristics, and aligning more with expert consensus.

TABLE 9

Prevalence estimations of PH in COPD populations in the three best performing models

| Best-performing models | Screening Predicted PH-COPD | Screening Predicted COPD-Only | Percent Positive in Screening Cohort | Numerator (Probable + 3012 PH-COPD) | Denominator | Estimated Prevalence | Sensitivity | Sensitivity - Corrected Prevalence |
|---|---|---|---|---|---|---|---|---|
| ECG Only | 810 | 6264 | 11.45% | 3822 | 53,327 | 7.17% | 0.802 | 6.87% |
| EHR only (Self-supervised) | 2003 | 28963 | 6.47% | 5015 | 76818 | 6.53% | 0.7685 | 5.92% |
| ECG + EHR | 745 | 6329 | 10.53% | 3757 | 53327 | 7.05% | 0.8027 | 6.77% |

The current study focused on the development of machine learning algorithms for detecting PH in patients with COPD. Features may originate directly from clinicians and their experience in treating the condition of interest. The objective was to identify key features that we could incorporate into the feature space for algorithm development. Overall, the physicians reported 6 clinical features with greater than or equal to 50% agreement, which were increased dyspnea on exertion, elevated NT pro-BNP, edema, signs of right heart failure and a high 02 requirement.

The univariate analysis and multivariate logistic regression were both preliminary ways of providing an initial understanding of each feature's potential to discriminate between the COPD only and PH COPD populations..

Using a comprehensive feature space comprising demographics, lab tests, observations, diagnoses, echo parameters and discrete ECG values, EHR only, ECG only and ECG+EHR neural networks were trained. These models have shown promising results, as evidenced by the high AUC values, balanced sensitivities and specificities, and strong positive and negative predictive values observed in the top-performing hypothesis-free EHR only, ECG only and ECG+EHR models. These metrics highlight the reliability and potential clinical utility of the models in early detection and management of PH within this patient population.

The integration of attention mapping for feature identification has demonstrated the robustness and reliability of the self-supervised EHR only algorithm. This approach may not only enhance the interpretability of the model but also provide valuable insights for clinical practice, potentially guiding targeted interventions and management strategies for at-risk patients.

The sensitivity-adjusted prevalence estimations, ranging from 5.9% to 6.87%, may provide a more accurate representation of the true burden of PH in COPD patients. This information may be crucial for healthcare planning and resource allocation, ensuring that appropriate measures are taken to address this significant health issue.

As a method of validating the 'probable-PH' labels generated from the models run on the screening cohort, prospective EHR data from 2020 through 2023 was used. The presence of mPAP≥25 from RHC or TRV>3.4 m/s from echocardiograms may serve as confirmatory indicators of PH diagnosis for a given patient. From the EHR only model, 161 out of 2003 patients had an available RHC or echo between 2020-2023. Out of those patients, 18.6% were correctly identified as positive PH. Similarly, for the ECG only algorithm, 56 out of 810 patients had an available RHC or echo between 2020-2023. Out of those patients, 26.8% of probable-PH labeled patients had positive results. Lastly, for the ECG+EHR model, 48 out of the 745 patients had an available RHC or echo in the future at Mayo and 27.1% of those were found to be positive. However, it is important to note that the evaluation of model accuracy, which may rely on confirmatory diagnosis via RHC or echocardiogram, may introduce a bias. This bias may arise from the fact that true negative cases, who may not require cardiac evaluation, are not screened, and hence are not included in the population, leading to a decreased PPR for PH-negative cases. Additionally, the model was trained on a preceding feature space window of 12 months to identify undiagnosed PH patients. Looking prospectively to understand model performance may frame the model objective in a predictive lens by potentially using features up to 8 years prior to PH diagnosis. Ultimately, these patients could be used as a hold-out test set for independent testing during a follow-up study.

In summary, these findings indicate that the models developed in this study may be reliable and potentially valuable tools for the detection of PH in COPD patients. The robustness of these models, combined with their clinical interpretability and relevance, underscores their potential impact on improving patient outcomes through timely and targeted interventions. Future work should be conducted to optimize model performance including incorporation of pulmonary function tests into the feature space.

6.1 Biases or Limitations 6.1.1 Methods to Minimize Bias

There was the potential for information bias, as data from the Mayo Clinic are generated from real-world clinical settings and are subject to miscoding and errors. Further, it is possible that there were missing data and other data quality and assessment issues pertaining to signs, symptoms, diagnoses, and procedures. Methods to address missingness were discussed in Section 4.2. However, it is unlikely that any of these errors are systemic and did not likely impact the findings.

6.1.2 Limitations

We anticipated the following limitations of the study based on the design proposed:

- Patient's treatment and medical history are limited to data available in the Mayo Clinic EHR. While any medication administered at Mayo should be captured, it may not be possible to establish the full patient history prior to COPD diagnosis.
- Patient outcomes and disease progression may be incomplete for patients who are lost to follow-up since they may continue treatment outside of the Mayo clinic.
- Data will be exclusively from a single, albeit multi-center, academic health system and may not be representative or translatable to community practices or smaller academic centers.

Data longitudinally may vary in both extent and frequency due to the variability in timing for real-world patient care (in contrast with controlled trials with set time points for data collection)

ML Model limitations:
   Logistic regression
      Cannot accommodate non-numerical values (requires feature scaling or transformation)
      Sensitive to outliers
      Can overfit in high-dimensional datasets
   Convolutional neural network
      A lot of training data is needed for the CNN to be effective.
      Computationally expensive
      Non-expressive learning and logics
      Prone to overfitting because they tend to be deployed on massive feature spaces

7. CONCLUSION

These findings indicate that PH-COPD patients have distinct clinical profiles from COPD-only patients and further understanding of this group may help clinicians identify patients who may benefit from PH-COPD screening. The results also show that models can be leveraged in a clinical system to improve detection of PH among COPD patients. This could facilitate PH-COPD patient referrals to PH specialty centers for individualized care in accordance with current guidelines, potentially improving clinical outcomes.

Figure 13:
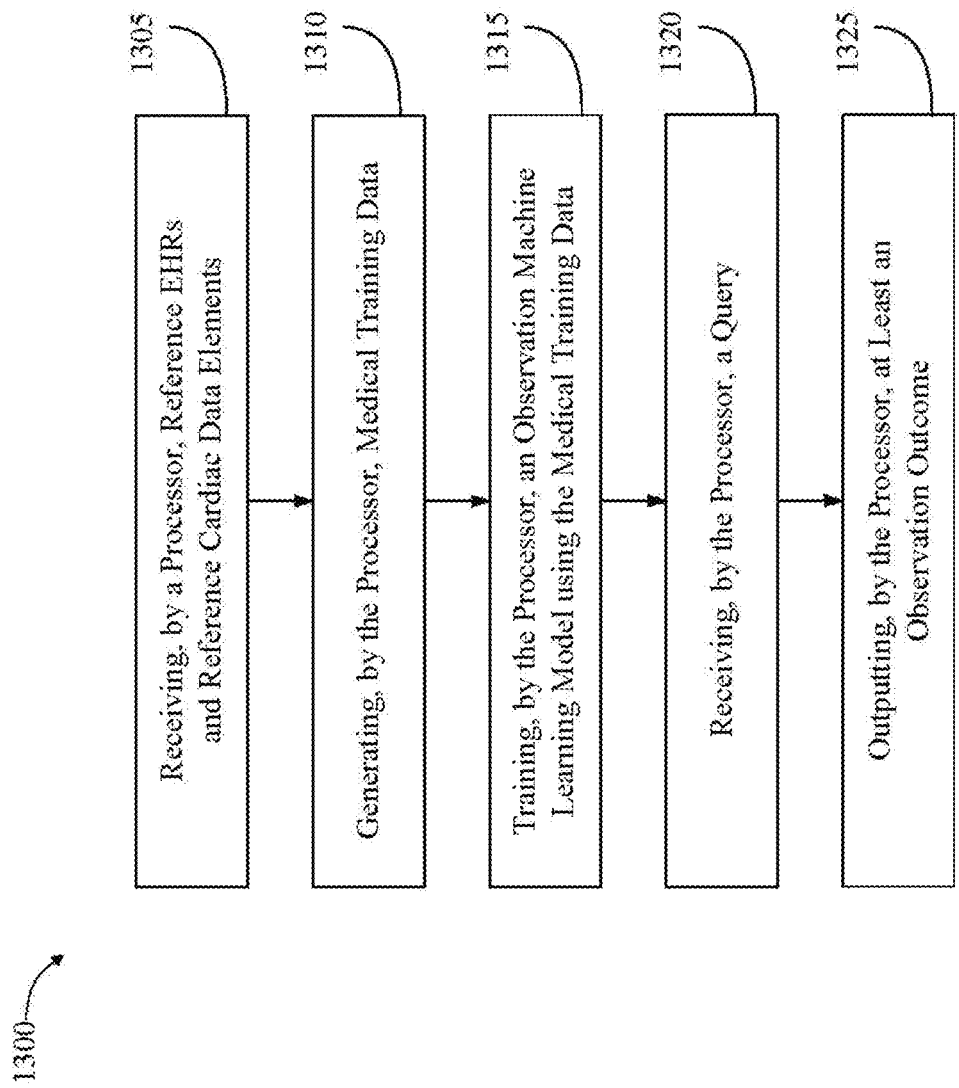
FIG. 13 is an exemplary flow diagram illustrating a method for observing medical conditions.

Referring now to FIG. 13, an exemplary embodiment of a method 1000 for observing medical conditions is described. At step 1305, method 1300 includes receiving, by processor 102 from data repository 106, plurality of reference EHRs and plurality of reference cardiac data elements 112. This step may be implemented with reference to details described above in this disclosure and without limitation.

With continued reference to FIG. 13, at step 1310, method 1300 includes generating, by processor 102, medical training data 116 including plurality of reference features 118 correlated with plurality of reference factors 120, wherein generating the medical training data 116 includes extracting the plurality of reference features 118 from plurality of reference cardiac data elements 112, isolating the plurality of reference factors 120 from plurality of reference EHRs 108, and correlating the plurality of reference features 118 and the plurality of reference factors 120 to generate the medical training data 116. This step may be implemented with reference to details described above in this disclosure and without limitation.

With continued reference to FIG. 10, at step 1315, method 1300 includes training, by processor 102, at least an observation machine learning model 128$a$-$n$ using generated medical training data 116. This step may be implemented with reference to details described above in this disclosure and without limitation.

With continued reference to FIG. 10, at step 1320, method 1300 includes receiving, by processor 102, query 144 pertaining to subject, wherein the query 144 includes at least a query cardiac data element 146 and at least a query EHR 148. This step may be implemented with reference to details described above in this disclosure and without limitation.

With continued reference to FIG. 13, at step 1325, method 1300 includes outputting, by processor 102, at least an observation outcome 152$a$-$n$ as a function of query 144 using at least an observation machine learning model 128$a$-$n$. This step may be implemented with reference to details described above in this disclosure and without limitation.

Figure 14:
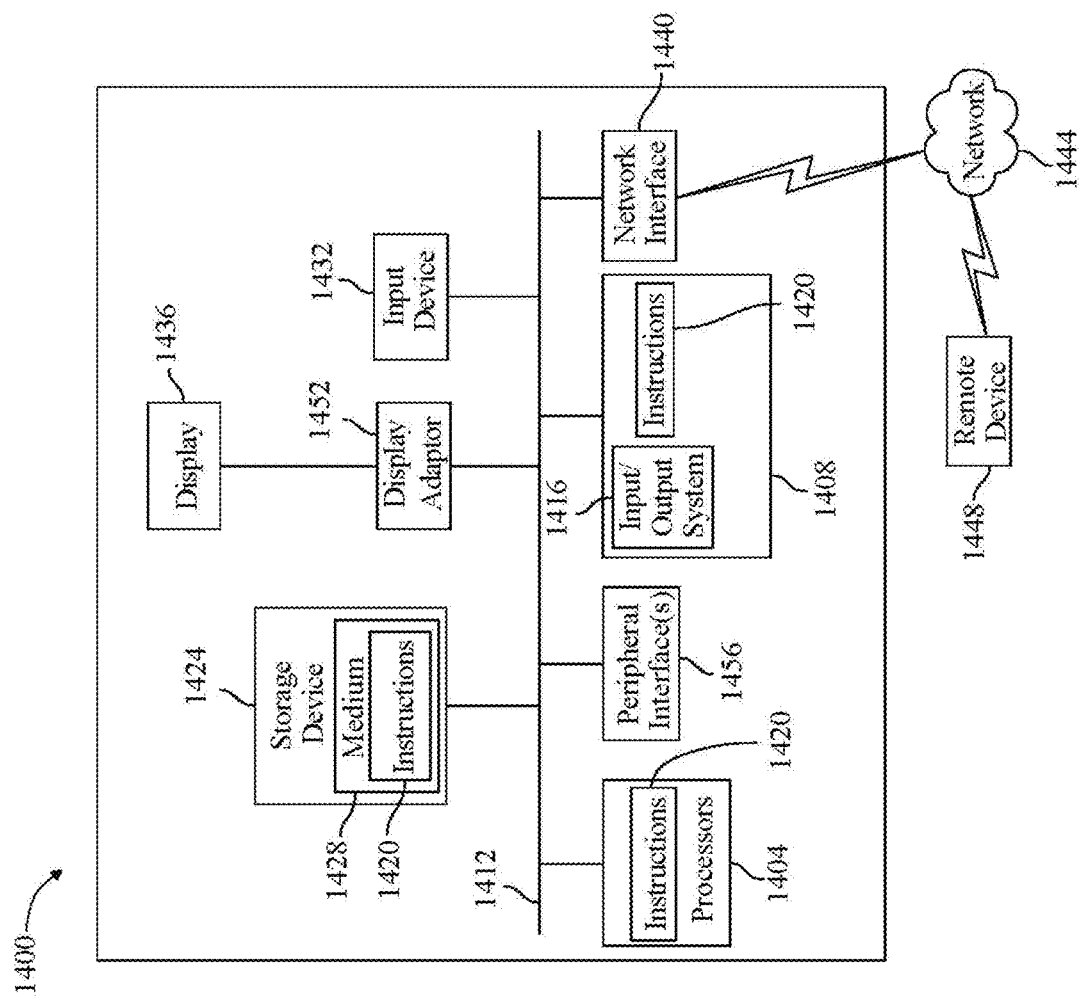
FIG. 14 is a block diagram of an exemplary embodiment of a computing system that can be used to implement any one or more of the methodologies disclosed herein and any one or more portions thereof.

Referring now to FIG. 14, it is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to one of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module. Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission. Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein. Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

With continued reference to FIG. 14, the figure shows a diagrammatic representation of one embodiment of a computing device in the exemplary form of a computing system 1400 within which a set of instructions for causing the computing system 1400 to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computing system 1400 may include a processor 1404 and a memory 1408 that communicate with each other, and with other components, via a bus

1412. Bus 1412 may include any of several types of bus structures including, but not limited to, a memory bus, a memory controller, a peripheral bus, a local bus, and any combinations thereof, using any of a variety of bus architectures. Processor 1404 may include any suitable processor, such as without limitation a processor incorporating logical circuitry for performing arithmetic and logical operations, such as an arithmetic and logic unit, which may be regulated with a state machine and directed by operational inputs from memory and/or sensors; processor 1404 may be organized according to Von Neumann and/or Harvard architecture as a non-limiting example. Processor 1404 may include, incorporate, and/or be incorporated in, without limitation, a microcontroller, microprocessor, digital signal processor, field programmable gate array, complex programmable logic device, graphical processing unit, general-purpose graphical processing unit, tensor processing unit, analog or mixed signal processor, trusted platform module, a floating-point unit, and/or system on a chip.

With continued reference to FIG. 14, memory 1408 may include various components (e.g., machine-readable media) including, but not limited to, a random-access memory component, a read only component, and any combinations thereof. In one example, a basic input/output system 1416, including basic routines that help to transfer information between elements within computing system 1400, such as during start-up, may be stored in memory 1408. Memory 1408 (e.g., stored on one or more machine-readable media) may also include instructions (e.g., software) 1420 embodying any one or more of the aspects and/or methodologies of the present disclosure. In another example, memory 1408 may further include any number of program modules including, but not limited to, an operating system, one or more application programs, other program modules, program data, and any combinations thereof.

With continued reference to FIG. 14, computing system 1400 may also include a storage device 1424. Examples of a storage device (e.g., storage device 1424) include, but are not limited to, a hard disk drive, a magnetic disk drive, an optical disc drive in combination with an optical medium, a solid-state memory device, and any combinations thereof. Storage device 1424 may be connected to bus 1412 by an appropriate interface (not shown). Example interfaces include, but are not limited to, small computer system interface, advanced technology attachment, serial advanced technology attachment, universal serial bus, IEEE 1394 (FIREWIRE), and any combinations thereof. In one example, storage device 1424 (or one or more components thereof) may be removably interfaced with computing system 1400 (e.g., via an external port connector (not shown)). Particularly, storage device 1424 and an associated machine-readable medium 1428 may provide nonvolatile and/or volatile storage of machine-readable instructions, data structures, program modules, and/or other data for computing system 1400. In one example, software 1420 may reside, completely or partially, within machine-readable medium 1428. In another example, software 1420 may reside, completely or partially, within processor 1404.

With continued reference to FIG. 14, computing system 1400 may also include an input device 1432. In one example, a user of computing system 1400 may enter commands and/or other information into computing system 1400 via input device 1432. Examples of input device 1432 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1432 may be interfaced to bus 1412 via any of a variety of interfaces (not shown) including, but not limited to, a serial interface, a parallel interface, a game port, a USB interface, a FIREWIRE interface, a direct interface to bus 1412, and any combinations thereof. Input device 1432 may include a touch screen interface that may be a part of or separate from display device 1436, discussed further below. Input device 1432 may be utilized as a user selection device for selecting one or more graphical representations in a graphical interface as described above.

With continued reference to FIG. 14, user may also input commands and/or other information to computing system 1400 via storage device 1424 (e.g., a removable disk drive, a flash drive, etc.) and/or network interface device 1440. A network interface device, such as network interface device 1440, may be utilized for connecting computing system 1400 to one or more of a variety of networks, such as network 1444, and one or more remote devices 1448 connected thereto. Examples of a network interface device include, but are not limited to, a network interface card (e.g., a mobile network interface card, a LAN card), a modem, and any combination thereof. Examples of a network include, but are not limited to, a wide-area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1444, may employ a wired and/or a wireless mode of communication. In general, any network topology may be used. Information (e.g., data, software 1420, etc.) may be communicated to and/or from computing system 1400 via network interface device 1440.

With continued reference to FIG. 14, computing system 1400 may further include a video display adapter 1452 for communicating a displayable image to a display device, such as display device 1436. Examples of a display device include, but are not limited to, a liquid crystal display (LCD), a cathode ray tube (CRT), a plasma display, a light emitting diode (LED) display, and any combinations thereof. Display adapter 1452 and display device 1436 may be utilized in combination with processor 1404 to provide graphical representations of aspects of the present disclosure. In addition to a display device, computing system 1400 may include one or more other peripheral output devices including, but not limited to, an audio speaker, a printer, and any combinations thereof. Such peripheral output devices may be connected to bus 1412 via a peripheral interface 1456. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for observing medical conditions, the system comprising:
    a processor; and
    a memory communicatively connected to the processor, wherein the memory contains instructions configuring the processor to:
        receive, from a data repository, a plurality of reference electronic health records (EHRs) and a plurality of reference cardiac data elements;
        generate medical training data comprising a plurality of reference features correlated with a plurality of reference factors, wherein generating the medical training data comprises:
            extracting the plurality of reference features from the plurality of reference cardiac data elements;
            isolating the plurality of reference factors from the plurality of reference EHRs; and
            correlating the plurality of reference features and the plurality of reference factors to generate the medical training data;
        train at least an observation machine learning model using the generated medical training data, wherein the at least an observation machine learning model comprises a transformer-based machine learning model that is configured to capture temporal interdependencies within the plurality of reference factors using attention mechanisms, wherein capturing the temporal interdependencies within the plurality of reference factors comprises generating an attention score as a function of at least a reference factor of the plurality of reference factors, wherein the observation machine learning model is further trained by:
            generating a plurality of diagnostic labels as a function of a plurality of correlations between the plurality of reference features and the plurality of reference factors; and
            updating the transformer-based machine learning model as a function of the attention score;
        receive a query pertaining to a subject, wherein the query comprises at least a query cardiac data element and at least a query EHR; and
        output at least an observation outcome as a function of the query using the at least an observation machine learning model, wherein outputting the at least an observation outcome comprises:
            selecting at least a diagnostic label by matching the query against the plurality of diagnostic labels; and
            outputting the at least an observation outcome as a function of at least a matched diagnostic label.

2. The system of claim 1, wherein:
    the at least a reference cardiac data element comprises at least a reference electrocardiogram (ECG); and
    the query cardiac data element comprises at least a query ECG.

3. The system of claim 1, wherein:
    at least a reference EHR of the plurality of reference EHRs comprises time series data;
    the plurality of reference factors comprises a plurality of temporal features; and
    training the at least an observation machine learning model comprises training the at least an observation machine learning model as a function of the time series data by assigning a weight to each temporal feature of the plurality of temporal features.

4. The system of claim 1, wherein generating the medical training data further comprises:
    identifying a medical history timeframe associated with at least a reference EHR of the plurality of reference EHRs; and
    segmenting the at least a reference EHR of the plurality of reference EHRs as a function of the medical history timeframe and an observation time of at least a month.

5. The system of claim 1, wherein outputting the at least an observation outcome comprises:
    calculating at least a distance metric between the at least a query cardiac data element and each reference cardiac data element of the plurality of reference cardiac data elements;
    identifying at least a matching reference EHR as a function of the at least a distance metric; and
    outputting the at least an observation outcome as a function of the at least a matching reference EHR.

6. The system of claim 1, wherein the processor is further configured to train an ensemble machine learning model as a function of the at least an observation machine learning model, wherein training the ensemble machine learning model comprises:
    receiving the at least an observation outcome from each of the at least an observation machine learning model;
    training the ensemble machine learning model as a function of the at least an observation outcome, wherein the ensemble machine learning model is configured to receive the at least an observation outcome from the at least an observation machine learning model as an input and output a weighted observation outcome; and
    generating the weighted observation outcome using the ensemble machine learning model.

7. The system of claim 1, wherein outputting the at least an observation outcome comprises:
    determining at least a likelihood metric using the at least an observation machine learning model;
    assigning the at least a likelihood metric to the at least an observation outcome; and
    ranking the at least an observation outcome as a function of the at least a likelihood metric.

8. The system of claim 7, further comprising a display device, wherein outputting the at least an observation outcome comprises displaying, using the display device, the at least an observation outcome as a function of the rank.

9. The system of claim 1, wherein outputting the at least an observation outcome comprises outputting at least a likelihood of chronic obstructive pulmonary disease (COPD).

10. A method for observing medical conditions, the method comprising:

receiving, by a processor from a data repository, a plurality of reference electronic health records (EHRs) and a plurality of reference cardiac data elements;

generating, by the processor, medical training data comprising a plurality of reference features correlated with a plurality of reference factors, wherein generating the medical training data comprises:
- extracting the plurality of reference features from the plurality of reference cardiac data elements;
- isolating the plurality of reference factors from the plurality of reference EHRs; and
- correlating the plurality of reference features and the plurality of reference factors to generate the medical training data;

training, by the processor, at least an observation machine learning model using the generated medical training data, wherein the at least an observation machine learning model comprises a transformer-based machine learning model that is configured to capture temporal interdependencies within the plurality of reference factors using attention mechanisms, wherein capturing the temporal interdependencies within the plurality of reference factors comprises generating an attention score as a function of at least a reference factor of the plurality of reference factors, wherein the observation machine learning model is further trained by:
- generating a plurality of diagnostic labels as a function of a plurality of correlations between the plurality of reference features and the plurality of reference factors; and
- updating the transformer-based machine learning model as a function of the attention score;

receiving, by the processor, a query pertaining to a subject, wherein the query comprises at least a query cardiac data element and at least a query EHR; and outputting, by the processor, at least an observation outcome as a function of the query using the at least an observation machine learning model, wherein outputting the at least an observation outcome comprises:
- selecting at least a diagnostic label by matching the query against the plurality of diagnostic labels; and
- outputting the at least an observation outcome as a function of at least a matched diagnostic label.

11. The method of claim 10, wherein:
the at least a reference cardiac data element comprises at least a reference electrocardiogram (ECG); and
the query cardiac data element comprises at least a query ECG.

12. The method of claim 10, wherein:
at least a reference EHR of the plurality of reference EHRs comprises time series data;
the plurality of reference factors comprises a plurality of temporal features; and
training the at least an observation machine learning model comprises training the at least an observation machine learning model as a function of the time series data by assigning a weight to each temporal feature of the plurality of temporal features.

13. The method of claim 10, wherein generating the medical training data further comprises:
- identifying a medical history timeframe associated with at least a reference EHR of the plurality of reference EHRs; and
- segmenting the at least a reference EHR of the plurality of reference EHRs as a function of the medical history timeframe and an observation time of at least a month.

14. The method of claim 10, wherein outputting the at least an observation outcome comprises:
- calculating at least a distance metric between the at least a query cardiac data element and each reference cardiac data element of the plurality of reference cardiac data elements;
- identifying at least a matching reference EHR as a function of the at least a distance metric; and
- outputting the at least an observation outcome as a function of the at least a matching reference EHR.

15. The method of claim 10, wherein the processor is further configured to train an ensemble machine learning model as a function of the at least an observation machine learning model, wherein training the ensemble machine learning model comprises:
- receiving the at least an observation outcome from each of the at least an observation machine learning model;
- training the ensemble machine learning model as a function of the at least an observation outcome, wherein the ensemble machine learning model is configured to receive the at least an observation outcome from the at least an observation machine learning model as an input and output a weighted observation outcome; and
- generating the weighted observation outcome using the ensemble machine learning model.

16. The method of claim 10, wherein outputting the at least an observation outcome comprises:
- determining at least a likelihood metric using the at least an observation machine learning model;
- assigning the at least a likelihood metric to the at least an observation outcome; and
- ranking the at least an observation outcome as a function of the at least a likelihood metric.

17. The method of claim 16, wherein outputting the at least an observation outcome comprises displaying, using a display device, the at least an observation outcome as a function of the rank.

18. The method of claim 10, wherein outputting the at least an observation outcome comprises outputting at least a likelihood of chronic obstructive pulmonary disease (COPD).

* * * * *